United States Patent [19]
Platz et al.

[11] Patent Number: 5,418,130
[45] Date of Patent: May 23, 1995

[54] METHOD OF INACTIVATION OF VIRAL AND BACTERIAL BLOOD CONTAMINANTS

[75] Inventors: Matthew S. Platz, Columbus, Ohio; Raymond P. Goodrich, Jr., Pasadena; Nagendar Yerram, South Pasadena, both of Calif.

[73] Assignee: Cryopharm Corporation, Pasadena, Calif.

[21] Appl. No.: 91,674

[22] Filed: Jul. 13, 1993

Related U.S. Application Data

[63] Continuation-in-part of Ser. No. 47,749, Apr. 14, 1993, which is a continuation-in-part of Ser. No. 825,691, Jan. 27, 1992, abandoned, which is a continuation-in-part of Ser. No. 685,931, Apr. 16, 1991, abandoned, which is a continuation-in-part of Ser. No. 656,254, Feb. 15, 1991, abandoned, which is a continuation-in-part of Ser. No. 632,277, Dec. 20, 1990, abandoned, which is a continuation-in-part of Ser. No. 510,234, Apr. 16, 1990, abandoned.

[51] Int. Cl.$^6$ .......................... A01N 1/02; C12N 13/00; C12N 7/06
[52] U.S. Cl. .................... 435/2; 435/173.3; 435/238; 424/529; 424/530; 424/531; 424/532; 424/533; 424/534
[58] Field of Search ................ 435/2, 173.3, 238; 424/529, 530, 531, 532, 533, 534

[56] References Cited

U.S. PATENT DOCUMENTS

| | | | |
|---|---|---|---|
| 2,720,485 | 10/1955 | Brueckner et al. | 167/80 |
| 3,019,168 | 1/1962 | Taylor | 167/78 |
| 3,333,583 | 8/1967 | Bodell | 128/142 |
| 3,399,264 | 8/1968 | Hyman | 424/257 |
| 3,686,395 | 8/1972 | Stephan | 424/101 |
| 3,779,706 | 12/1973 | Nablo | 21/54 R |
| 3,788,319 | 1/1974 | Gillette | 128/214 B |
| 3,802,432 | 4/1974 | Djerassi | 128/214 R |
| 3,857,393 | 12/1974 | Rose | 128/214 R |
| 3,892,236 | 7/1975 | Djerassi | 128/214 R |
| 3,929,130 | 12/1975 | Hargest et al. | 128/214 R |
| 3,940,249 | 2/1976 | McClurg | 23/230 R |
| 3,962,252 | 6/1976 | Wu | 260/279 R |
| 3,963,613 | 6/1976 | Chibata et al. | 210/195 R |
| 3,993,560 | 11/1976 | Halpern | 210/94 |
| 4,008,136 | 2/1977 | Williams | 204/158 R |
| 4,021,551 | 5/1977 | Cullen | 424/246 |
| 4,039,413 | 8/1977 | Kraemer et al. | 204/159.12 |
| 4,071,412 | 1/1978 | Eisenberg et al. | 195/102 |
| 4,103,685 | 8/1978 | Lupien et al. | 128/214 R |
| 4,124,598 | 11/1978 | Hearst et al. | 260/343.21 |
| 4,150,134 | 4/1979 | Schulenberg | 424/257 |
| 4,160,644 | 7/1979 | Ryan | 23/230 B |
| 4,196,281 | 4/1980 | Hearst et al. | 536/28 |
| 4,197,088 | 4/1980 | Meserol et al. | 23/230 B |
| 4,216,770 | 8/1980 | Cullis et al. | 128/214 R |
| 4,235,887 | 11/1980 | Voorhees et al. | 424/180 |
| 4,251,437 | 2/1981 | Rasmussen et al. | 260/112 B |
| 4,268,279 | 5/1981 | Shindo et al. | 55/16 |
| 4,291,034 | 9/1981 | Werbel | 424/250 |
| 4,308,249 | 12/1981 | Frank et al. | 424/1 |

(List continued on next page.)

FOREIGN PATENT DOCUMENTS

| | | |
|---|---|---|
| 27521 | 7/1987 | Australia . |
| 859912 | 4/1978 | Belgium . |
| 1224622 | 7/1987 | Canada . |

(List continued on next page.)

OTHER PUBLICATIONS

CCBC Newsletter Dec. 21/28 1990.
Lown et al., 9. Med. Chem. 32:2368-2375 (1989).
Debart et al, 9. Med. Chem. 32:1074-1083 (1989).
Polak 9 et al, Pharm. Delt, Epistom Ekoosis 1:27-33 (1971).

(List continued on next page.)

Primary Examiner—Marian C. Knode
Assistant Examiner—Sandra Saucier
Attorney, Agent, or Firm—Swanson & Bratschun

[57] ABSTRACT

A method is provided for inactivating viral and/or bacterial contamination in blood cellular matter, such as erythrocytes and platelets, or protein fractions. The cells or protein fractions are mixed with chemical sensitizers and irradiated with, for example, UV, visible, gamma or X-ray radiation. In particular, quaternary ammonium or phosphonium substituted, halo-psoralen compounds are described as being useful.

41 Claims, 22 Drawing Sheets

U.S. PATENT DOCUMENTS

| | | | |
|---|---|---|---|
| 4,314,061 | 2/1982 | Murdock | 544/80 |
| 4,321,918 | 3/1982 | Clark, II | 128/214 R |
| 4,321,919 | 3/1982 | Edelsen | 128/214 R |
| 4,325,715 | 4/1982 | Bowman | 55/158 |
| 4,329,986 | 5/1982 | Babb | 128/214 R |
| 4,350,156 | 9/1982 | Malchesky et al. | 128/214 R |
| 4,370,264 | 1/1983 | Kotitschke et al. | 260/112 B |
| 4,398,031 | 8/1983 | Bender et al. | 549/282 |
| 4,398,906 | 8/1983 | Edelson | 604/6 |
| 4,401,647 | 8/1983 | Krohn et al. | 424/1.5 |
| 4,402,318 | 9/1983 | Swartz | 604/20 |
| 4,409,105 | 11/1983 | Hayashi et al. | 210/679 |
| 4,411,518 | 10/1983 | Meserol et al. | 356/39 |
| 4,428,744 | 1/1984 | Edelson | 604/6 |
| 4,436,821 | 3/1984 | Ryan | 436/10 |
| 4,464,166 | 8/1984 | Edelson | 604/6 |
| 4,472,509 | 9/1984 | Gansow et al. | 435/548 |
| 4,479,798 | 10/1984 | Parks | 604/175 |
| 4,503,039 | 3/1985 | Kotitschke et al. | 421/101 |
| 4,540,573 | 9/1985 | Neurath et al. | 425/85 |
| 4,545,987 | 10/1985 | Giles et al. | 424/89 |
| 4,568,542 | 2/1986 | Kronenberg | 424/90 |
| 4,595,653 | 6/1986 | Kronenberg | 435/5 |
| 4,613,322 | 9/1986 | Edelson | 604/6 |
| 4,613,501 | 9/1986 | Horowitz et al. | 424/89 |
| 4,620,908 | 11/1986 | Van Duzer | 264/157.68 |
| 4,683,120 | 7/1987 | Meserol et al. | 422/72 |
| 4,684,521 | 8/1987 | Edelson | 424/101 |
| 4,693,981 | 9/1987 | Wiesehahn et al. | 435/238 |
| 4,727,027 | 2/1988 | Wiesehahn et al. | 435/173 |
| 4,729,959 | 3/1988 | Ryan | 436/14 |
| 4,748,120 | 5/1988 | Wiesehahn | 435/173 |
| 4,755,684 | 7/1988 | Leiner et al. | 250/461.1 |
| 4,764,369 | 8/1988 | Neunath et al. | 424/89 |
| 4,788,139 | 11/1988 | Ryan | 435/13 |
| 4,791,062 | 12/1988 | Wiesehahn et al. | 435/238 |
| 4,820,805 | 4/1989 | Neurath et al. | 530/410 |
| 4,837,160 | 6/1989 | Meserol et al. | 436/45 |
| 4,841,023 | 6/1989 | Horowitz | 530/351 |
| 4,866,073 | 9/1989 | Bair | 514/297 |
| 4,866,282 | 9/1989 | Miripol et al. | 250/455.1 |
| 4,870,018 | 9/1989 | Lehmann | 435/240.1 |
| 4,874,690 | 10/1989 | Goodrich et al. | 435/2 |
| 4,877,866 | 10/1989 | Rudnick et al. | 530/387 |
| 4,878,891 | 11/1989 | Judy et al. | 604/5 |
| 4,891,319 | 1/1990 | Roser | 435/188 |
| 4,898,891 | 2/1990 | Lavie et al. | 514/732 |
| 4,909,940 | 3/1990 | Horowitz et al. | 210/634 |
| 4,927,502 | 5/1990 | Reading et al. | 204/153.1 |
| 4,946,648 | 8/1990 | Dictelmuller et al. | 422/24 |
| 4,950,665 | 8/1990 | Floyd | 514/222.8 |
| 4,952,812 | 8/1990 | Miripol et al. | 250/455.1 |
| 4,971,760 | 11/1990 | Rubenstein | 422/37 |
| 4,973,327 | 11/1990 | Goodrich et al. | 604/408 |
| 4,992,272 | 2/1991 | Bass et al. | 424/89 |
| 5,000,951 | 3/1991 | Bass et al. | 424/89 |
| 5,004,355 | 4/1991 | Ryan | 374/194 |
| 5,008,201 | 4/1991 | Ryan | 436/10 |
| 5,011,695 | 4/1991 | Dichtelmuller et al. | 424/529 |
| 5,026,566 | 6/1991 | Roser | 426/443 |
| 5,026,840 | 6/1991 | Dahagrupta et al. | 536/27 |
| 5,030,200 | 7/1991 | Judy et al. | 604/5 |
| 5,049,589 | 9/1991 | Lavie et al. | 514/732 |
| 5,053,121 | 10/1991 | Schoendorfer et al. | 210/90 |
| 5,053,423 | 10/1991 | Liu | 514/410 |
| 5,106,619 | 4/1992 | Wiesehahn et al. | 424/89 |
| 5,120,412 | 6/1992 | Mazur et al. | 204/157.87 |
| 5,120,649 | 6/1992 | Horowitz et al. | 435/173 |
| 5,149,653 | 9/1992 | Roser | 435/260 |
| 5,176,921 | 1/1993 | Wiesenhahn et al. | 424/529 |
| 5,182,111 | 1/1993 | Aebischer et al. | 424/424 |
| 5,185,371 | 2/1993 | Rubenstein | 422/28 |
| 5,186,945 | 2/1993 | Shanbrom | 424/529 |
| 5,216,176 | 6/1993 | Heindel et al. | 549/280 |
| 5,263,925 | 11/1993 | Gilmore, Jr. et al. | 604/4 |
| 5,288,605 | 2/1994 | Lin et al. | 435/90.2 |
| 5,292,414 | 3/1994 | Sessler et al. | 204/157.5 |
| 5,356,929 | 10/1994 | Heindel et al. | 514/455 |

FOREIGN PATENT DOCUMENTS

| | | |
|---|---|---|
| 0124363 | 11/1984 | European Pat. Off. |
| 0196515 | 8/1986 | European Pat. Off. |
| 0334679 | 9/1989 | European Pat. Off. |
| 0402637 | 5/1990 | European Pat. Off. |
| 60-16930 | 1/1985 | Japan |
| 61-275228 | 12/1986 | Japan |
| 635346 | 3/1983 | Switzerland |
| 8502628 | 6/1985 | WIPO |
| 8901630 | 2/1989 | WIPO |
| WO9003187 | 9/1989 | WIPO |
| 9001563 | 2/1990 | WIPO |
| WO9012581 | 11/1990 | WIPO |
| 9103933 | 4/1991 | WIPO |
| WO9106665 | 5/1991 | WIPO |
| 9106843 | 5/1991 | WIPO |
| 9102504 | 8/1991 | WIPO |
| 9207957 | 5/1992 | WIPO |
| 9208807 | 5/1992 | WIPO |
| WO94/06424 | 3/1994 | WIPO |
| WO9420090 | 9/1994 | WIPO |

OTHER PUBLICATIONS

Mahnel H. et al, Zbl. Baki., I. Abt. Orig. B 170:57–70 (1980).

Alter, H. J. et al, The Lancet Dec. 24/31:1446–1450 (1988).

Hansen, J. B. et al, J. Med Chem 28:1001–1010 (1985).

Gibbs, Jr. C. et al, Proc. Natl Acad Sci USA 75:6268–6270 (1978).

Potapenko, A. Y., et al., "8-Methoxypsoralen-sensitized Photooxidation of Tocopherols", *Photochem. Photobiophy.*, V. 5, pp. 113–117 (1983).

Artuc, M. et al, "Reversible Binding of 5- and 8- Methoxy-Psoralen to Human Serum Proteins (Albumin) and to Epidermis In Vitro", British J. Dermatol., V. 101, 669–677 (1979).

Ashwood-Smith, M. J. et al., "5-Methoxypsoralen, an Ingredient in Several Suntan Preparations, has Lethal, Mutagenic and Clastogenic Properties", Nature V. 285, pp. 407–409, (1980).

Bahnemann, "Inactivation of Viruses in Serum with Binary Ethyleneimine," J. Clin. Microbiol., V. 3, No. 2, pp. 209–210, (1976).

(List continued on next page.)

OTHER PUBLICATIONS

Chun, C. C. Y., "Kinetics of Psoralen Photoreaction with Deoxyribonucleic Acid", UMI Dissertation Services 1982.

Chabner et al, Cancer: Principles and Practice of Oncology, Chapter 14, pp. 311–312 (1985) V. DeVita editor.

Khan et al., J. Virology 21: 16–23 (1977).

Kalab D., Experentia 23: 181–182 (1967). Goodrich, et al., (1994) *Proc. Natl. Acad. Sci. USA* 91:5552–5556, Selective Inactivation of Viruses in the Presence of Human Platelets: UV Sensitization with Psoralen Derivatives.

Goodrich, et al., (1994) *Proc. Natl. Acad. Sci. USA* 91:5552–5556, Selective Inactivation of Viruses in the Presence of Human Platelets: UV Sensitization with Psoralen Derivatives.

Gasparro, F. P., *Psoralen DNA Photobiology* pp. 37, 39–46 CRC Press, Inc. (1988).

Cimino, G. D., et al., "Psoralens as Photoactive Probes of Nucleic Acid Structure and Function: Organic Chemistry, Photochemistry, and Biochemistry", Ann. Rev. Biochem., V. 54, pp. 1151–1193 (1985).

Colombo, G. et al., "Photosensitization of Mammalian Cells and of Animal Viruses by Furocoumarins", Progr. Biochem. Pharmacol., V. 1, pp. 392–399 (1965).

Dodd, R. Y., et al., "Inactivation of Viruses in Platelet Suspensions that Retain Their in Vitro Characteristics: Comparison of Psoralen–Ultraviolet A and Merocyanine 540–Visible Light Methods", Transfusion, V. 31, No. 6, pp. 483–490 (1991).

Edelson, R. L., "Light–Activated Drugs", Scientific American, pp. 68–75 (Aug. 1988).

Edelson, R., et al., "Treatment of Cutaneous T–Cell Lymphoma by Extracorporeal Photochemotherapy", New England J. of Med., V. 316, No. 6, pp. 297–303 (1987).

El–Hefnawi, H., et al., "Electrophoretic Studies of Serum Proteins in Vitiligenous Patients Treated with Oral Psoralens and Ultra–Violet Irradiation", J. Invest. Dermatol., V. 40, No. 2, pp. 111–119 (1963).

Farid, S., et al., "Photochemical and –Biological Reactions of the Furocoumarins", Radiation Research, pp. 869–886 (1966).

Frederiksen, S. et al., "Binding of 4'–Aminomethyl 4,5'8–Trimethyl Psoralen to DNA, RNA and Protein in HeLa Cells and Drosophila Cells", Biochimica et Biophysica Acta, V. 563, pp. 343–355 (1979).

Fritsch, P. O., et al., "Augmentation of Oral Methoxsalen–Photochemotherapy with an Oral Retinoic Acid Derivative", J. Invest. Dermatol., V. 70, No. 4, pp. 178–182 (1978).

Grossweiner, L. I., "Mechanisms of Photosensitization by Furocoumarins", Paper presented at conference on Photobiologic, Toxicologic, and Pharmacologic Aspects of Psoralens, National Technical Information Service, USDC (Feb. 28, 1985).

Hallick, L. M., et al., "Photochemical Addition of the Cross–Linking Reagent 4,5'8–Trimethylpsoralen (Trioxsalen) to Intracellular and Viral Simian Virus 40 DNA–Histone Complexes", J. Virol., V. 27, No. 1, pp. 127–135 (1978).

(List continued on next page.)

OTHER PUBLICATIONS

Hallick, L. M., et al., "*Photoaddition of Trimethylpsoralen as a Probe for the Intracellular Organization of Escherichia coli DNA*", Nucleic Acids Research, V. 8, No. 3 pp. 611–622 (1980).

Hanson, C. V., "*Inactivation of Viruses for Use as Vaccines and Immunodiagnostic Reagents*", Medical Virolog II, Elsevier Biomedical Press, New York, pp. 45–79 (1982).

Hanson, C. V., et al., "*Photochemical Inactivation of DNA and RNA Viruses by Psoralen Derivatives*", J. Genet. Virol. V. 40, pp. 345–358 (1978).

Hanson, C. V., "*Photochemical Inactivation of Deoxyribonucleic and Ribonucleic Acid Viruses by Chlorpromazine*", Antimicrobial Agents and Chemo, V. 15, No. 3, pp. 461–464 (1979).

Hartman, F. W., et al., "*Four-Year Study Concerning th Inactivation of Viruses in Blood and Plasma*", Amer Assoc. Gastro–Ent., V. 28, No. 2, pp. 244–256 (Feb 1955).

Hartman, F. W., et al., "*Beta–Propiolactone in Sterilization of Vaccines, Tissue Grafts and Plasma*", J. Amer Med. Assoc., V. 164, No. 3, pp. 258–260 (1957).

Hearst, J. E., et al., "*The Photoinactivation of an RNA Animal Virus, Vesicular Stomatitis Virus, with the Aid of Newly Synthesized Psoralen Derivatives*", Nucleic Acid Research V. 4, No. 5, pp. 1339–1347 (1977).

Hearst, J. E., "*Protocols for the Clinical Use of New Psoralens Derived from Physical Properties*", Psoriasis, Proc Int. Symp., 3rd, pp. 143–147 (1982).

Hearst, J. E., "*Psoralen Photochemistry*", Ann. Rev. Biophys. Bioeng., vol. 10, pp. 69–86 (1981).

Hearst, J. E., "*The Reaction of the Psoralens with Deoxyribonucleic Acid*", Q. Rev. Biophys., vol. 17, No. 1, pp. 1–44 (1984).

Hearst, J. E., "*Psoralen Photochemistry and the Structures of Single–Stranded Nucleic Acids*", Stud. Biophys., vol. 94, pp. 25–30 (1983).

Hearst, J. E., "*Photochemistry of Psoralens and Structure of Nucleic Acids*", Bioorganicheskaya Khimiya, V. 8, No. 7, pp. 945–953 (1982).

Hiatt, C. W., "*Methods for Photoinactivation of Viruses*", Concepts in Radiation Cell Biology, A. castellani, ed., Plenum Press, N.Y., pp. 57–89 (1977).

Ikoku, A. S., "*DNA Packaging in Filamentous Single–Stranded DNA Viruses as Probed by Psoralen Photochemical CrossLinking*", UMI Dissertation Services (1980).

Isaacs, S. T., et al., *Synthesis and Characterization of New Psoralen Derivatives with Superior Photoreactivity with DNA and RNA*", Biochemistry vol. 16, No. 6, pp. 1058–1064 (1977).

Isaacs, S. T., et al., "*A Photochemical Characterization of Reactions of Psoralen Derivatives with DNA*", Trends Photobiol. (Phoc. Int. Congr. Photobiol.), 8th, pp. 279–294 (1982).

Johnson, B. H., "*Dynamics of the Psoralen–DNA Photoreaction*", UMI Dissertation Services (1980).

Kanne D., et al., "*Psoralen–Deoxyribonucleic Acid Photoreaction. Characterization of the Monoaddition Products from 8–Methoxypsoralen and 4,5',8–Trimethylpsoralen*", Biochemistry, V. 21, pp. 861–871 (1982).

Kondoleon, S. K., et al., "*Kinetics of Simian Virus 40 and Lambda Inactivation by Photoaddition of Psoralen Derivatives*", Photochem. V. vol. 36, pp. 325–331 (1982).

Kondoleon, S. K., et al., "SV40 Virus Particles Lack a Psoralen–Accessible Origin and Contain an Altered Nucleoprotein Structure", Virology, V. 129, pp. 261–273 (1983).

Kraemer, K. H., et al., "*Psoralen Plus Ultraviolet Radiation–Induced Inhibition of DNA Synthesis and Viability in Human Lymphoid Cells in Vitro*", Photochem. Photobiol. V. 30, pp. 263–270 (1979).

Kruger, J. P., et al., "*Dose–Effects of 8–Methoxypsoralen and UVA in Cultured Human Lymphocytes*", Br. J. Dermatol. V. 98, pp. 141–144 (1978).

Lamola, A. A., "*Photodegradation of Biomembranes*", Research in Photobiol., A Castellani, ed., Plenum Press, N.Y., pp. 53–63 (1977).

Lewin, A. A., et al., *Photodynamic Inactivation of herpes Simplex Virus by Hematoporphyrin Derivative and Light*", Proc. Soc. Exp. Biol. Med., V. 163, pp. 81–90 (1980).

Li, C. P., et al., "Antiviral Activity of 8–Methoxypsoralen", Fed. Proceed., V. 21, No. 1, p 457 (Abstract) (1962).

LoGrippo, G. A., et al., "*Chemical and Combined Methods for Plasma Sterilization*", Int'l. Soc. of Blood Transfusions, pp. 225–230 (1968), Int. Haematology.

LoGrippo, G. A., et al., "*Efficacy of Betaprone with Ultraviolet Irradiation on Hepatits B Antigen In Human Plasma Pools*", Henry Ford Hosp. Med. J., V. 21, No. 4, pp. 181–186 (1973).

LoGrippo, G. A., "*Investigations of the Use of Beta—Propiolactone in Virus Inactivation*", Annals N.Y. Acad. Sci., V. 83, pp. 578–594 (1959).

(List continued on next page.)

OTHER PUBLICATIONS

Lovric, V. A., et al., "*Donor Blood Frozen and Stored Between −20° C. and −24° C. with 35-Day Post-Thaw Shelf Life*", The Lancet, pp.71–73 (1989).

Mannucci, P. M., et al., "*Virucidal Treatment of Clotting Factor Concentrates*", The Lancet, pp. 782–785 (1988).

Margolis-Nunno, H., et al., *Virus Sterilization in Platelet Concentrates with Psoralen and Ultraviolet A Light in the Presence of Quenchers*", Transfusion, V. 32, No. 6, pp. 541–547 (1992).

Matthews, J. L., et al., "*Photodynamic Therapy of Viral Contaminants with Potential for Blood Banking Applications*", Transfusion, V. 28, No. 1, pp. 81–83 (1988).

McKinley, M.P., et al., "*Resistance of the Scraple Agent to Inactivation by Psoralens*", Photochem. Photobiol, V. 37, No. 5, pp. 539–545 (1983).

Melnick, J. L., "*Photodynamic Inactivation of Herpesvirus*", Antiviral mechanisms, Perspectives in Virology IX., M. Pollard (ed), Academic Press, N.Y. pp. 297–314 (1975).

Melski, J. W., et al., "*Oral Methoxsalen Photochemotherapy for the Treatment of Psoriasis: A Cooperative Clinical Trial*", J. Invest Dermat., V. 68, No. 6, pp. 328–335 (1977).

Moore, S. P., et al., "*The Wavelength Dependence of the Effect of 8-Methoxypsoralen Plus Ultraviolet Radiation on the Induction of Latent Simian Virus 40 from a Mammalian Cell*", Photochem. Photobiol., V. 34, pp. 609–615 (1981).

Moroff, G., et al., "*Factors Influencing Virus Inactivation and Retention of Platelet Properties Following Treatment with Aminomethyltrimethylpsoralen and Ultraviolet A Light*", Blood Cells, V. 18, pp. 43–56 (1992).

Murray, R., et al., "*Effect of Ultraviolet Radiation on the Infectivity of Icterogenic Plasma*", J.A.M.A., V. 157, No. 1, pp. 8–14. (1955)

Musajo, L., et al., "*Photosensitizing Furocoumarins: Interaction with DNA and Photo-Inactivation of DNA Containing Viruses*", Experientia V. 21, No. 1, pp. 22–24 (1965).

Musajo, L., et al., "*Photoreactions Between Skin-Photosensitizing Furocoumarins and Nucleic Acids*", Sunlight and Man, University of Tokyo Press, pp. 369–430 (1974).

Nakashima, K., et al., "*Differential Dependence of Reovirus-Associated Enzyme Activities on Genome RNA as Determined by Psoralen Photosensitivity*", J. Biol. Chem. V. 254, No. 16, pp. 8007–8014 (1979).

Nakashima, K., et al., "*Photochemical Cross-Linking of Reovirus Genome RAN in Situ and Inactivation of Viral Transcriptase*", J. Biol. Chem., V. 253, No. 24, pp. 8680–8682 (1978).

Neyndorff, H. C., et al., "*Development of a Model to Demonstrate Photosensitizer-Mediated Viral Inactivation in Blood*", Transfusion, V. 30, No. 6, pp. 485–490 (1990).

Parrish, J. A., et al., "*Photochemotherapy of Psoriasis with Oral Methoxsalen and Longwave Ultraviolet Light*", New England J. Med. V. 291, No. 23, pp. 1207–1211 (1974).

Potapenko, A. Y., et al., "*Inhibition of Erythema of the Skin Photosensitized with 8-Methoxypsoralen by α-Tocopherol*", Bull. Exp. Biol. Med. (U.S.S.R.) pp. 611–615 (1980).

Prince, A. M., et al., "*β-Propiolactone/Ultraviolet Irradiation: A Review of Its Effectiveness for Inactivation of Viruses in Blood Derivatives*", Rev. of Infect. Dis., V. 5, No. 1, pp. 92–107, (1983).

Prince, A. M., et al., "*Evaluation of the Effect of Beta-propiolactone/Ultraviolet Irradiation (BPL/UV) Treatment of Source Plasma on Hepatitis Transmission by Factor IX Complex in Chimpanzees*", Throm. Haemost., V. 44, pp. 138–142 (1980).

Prince, A. M., et al., "*The Development of Virus-Free Labile Blood Derivatives-A Review*", Eur. J. Epidemiol., V. 3, N. 2, pp. 103–118 (1987).

Puglisi, C. V., et al., "*Determination of 8-Methoxypsoralen, a Photoactive Compound, in Blood by High Pressure Liquid Chromatography*", Analyt. Letters, V. 10, No. 1, pp. 39–50 (1977).

Redfield, D. C., et al., "*Psoralen Inactivation of Influenza and Herpes Simplex Viruses and of Virus-Infected Cells*", Infect. and Immun., V. 32, No. 3, pp. 1216–1226 (1981).

Robinson, G. W., et al., "*Mapping the In Vivo Arrangement of Nucleosomes on Simian Virus 40 Chromatin by the Photoaddition of Radioactive Hydroxymethyltrimethylpsoralen*", J. of Virology, V. 41, No. 1, pp. 78–87 (1982).

Salet, C., et al., "*Photodynamic Effects Induced by Furocoumarins on a Membrane System, Comparison with Hematoporphyrin*", Photochem. Photobiol., V. 36, pp. 291–296 (1982).

Scott, B. R., "*Molecular and Genetic Basis of Furocoumarin Reactions*", Mutation Research, V. 39, pp. 29–74 (1976).

(List continued on next page.)

OTHER PUBLICATIONS

Shen, C. J., "*Photochemical Crosslinking of Nucleic Acids with Psoralens as a Probe for the Genome Structure of Prokaryotes and Eukaryotes*" UMI Dissertation Services (1977).

Snipes, W., et al., "*Inactivation of Lipid–Containing Viruses by Hydrophobic Photosensitizers and Near–Ultraviolet Radiation*", Photochem. Photobiol., V. 29, pp. 785–790 (1979).

Song, P. S., "*Photochemistry and Photobiology of Psoralens*", Photochem Photobiol., V. 29, pp. 1177–1197 (1979).

Spikes, J. D., "*Photodynamic Reactions in Photomedicine*", Science of Photomedicine, Plunum Publishing Corp., N.Y., pp.113 144 (1982).

Spikes, J. D., "*Sensitized Photochemical Processes in Biological Systems*", Annual Review of Physical Chem., V. 18, pp. 409–436 (1967).

Stephan, W., "*Hepatitis–Free and Stable Human Serum for Intravenous Therapy*", XXIVth Scientific Meeting of the Blood Research Institute, pp. 442–457. (1971).

Stephan, W., "*Undegraded Human Immunoglobulin for Intravenous Use*", Vox Sang, V. 28, pp. 422–437 (1975).

Stephan, W., et al., "*Effect of Combined Treatment of Serum Containing Hepatitis B Virus and Beta–Propiolactone and Ultraviolet Irradiation*", Vox Sang, V. 41, pp. 134–138 (1981).

Stephan, W., "*Long–Term Tolerance and Recovery of β–Propiolactone/Ultraviolet (βPL/UV) Treated PPSB in Chimpanzees*", Thrombos. Haemostas. (Stuttgart), v. 46, No. 2, pp. 511–514 (1981).

Swanstrom, R., et al., "*Interaction of Psoralen Derivatives with the RNA Genome of Rous Sarcoma Virus*", Virology, V. 113, pp. 613–622 (1981).

Thiers, B. H., "*Unusual Treatments for Herpesvirus Infections*", J. Amer. Acad. Dermatol., V. 7, No. 6, pp. 811–816 (1982).

Thompson, J. F., "*Reaction of Psoralen with RNA; Specificity and Use as a Probe for Secondary–Structure Analysis*", Ph.D. thesis, Lawrence Berkeley Laboratory, University of California, LBL–14991 (Sep. 1982).

Tillotson, J. R., et al., "*Effect of Periodate Oxidation on Hemagglutinating and Antibody–Producing Capacities of Certain Enteroviruses and Reoviruses*", Proc. N.A.S., V. 56, pp. 1143–1150 (1966).

Varga, J. M., et al., "*Dose–Related Effects of Psoralen and Ultraviolet Light on the Cell Cycle of Murine Melanoma Cells*", Cancer Res., V. 42, pp. 2223–2226 (1982).

Veronese, F. M., et al., "*Drug–Protein Interaction: Plasma Protein Binding of Furocoumarins*", Farmaco Ed. Sci., V. 34, No. 8, pp. 716–725 (1979).

Veronese, F. M., et al., "*The Binding of 8–Methoxypsoralen by Human Serum Albumin*", Farmaco Ed. Sci., V. 33 No. 9, pp. 667 675 (1978).

Wagner, S. J., et al., "*Determination of Residual 4'–Aminomethyl–4,5',8–Trimethylpsoralen and Mutagenicity Testing Following Psoralen Plus UVA Treatment of Platelet Suspensions*", Photochem. Photobiol., V. 57, No. 5, pp. 819–824 (1993).

Wallis, C., et al., "*Photodynamic Inactivation of Animal Viruses: A Review*", Photochemistry and Photobiology, V. 4 pp. 159–170 (1965).

Wiesehahn, G., "*Photochemical Decontamination Treatment of Whole Blood or Blood Components*", Application No. 84/03270, date of publication Nov. 28, 1984 (Abstract). Republic of South Africa.

Wiesehahn, G., et al., "*Studies on the Structure of DNA, Alkaline Denaturation, Unwinding Angle of Psoralen Derivatives and Specificity of Trioxsalen Crosslinks in Nuclei*", UMI Dissertation Services (1978).

Wiesehahn, G. P., "*Interactions of Daunomycin and Melanotropin–Daunomycin with DNA*", Nature, V. 292, pp. 467–469 (1981).

Wollenzien, P. L., "*The Structure of Ribosomal–RNA Detected by Psoralen Photochemical Crosslinking*", UMI Dissertation Services (1979).

Young, A. R., "*Photocarcinogenicity of Psoralens Used in PUVA Treatment: Present Status in Mouse and Man*", J. of Photochem. Photobiol., B. Biol., V. 6, pp. 237–247 (1990).

Pathak M. A. et al in Sunlight and Man, Pathak et al editor, U. of Tokyo Press, Tokyo, Japan, Chapter 22 pp. 335–368 (1972).

Scott, J., et al., "Metalloporphyrin in Phototoxicity", J. of Photochemistry and Photobiology, B:Biology, 7, (1990), 149–157.

Pjura, P., et al., "Binding of Hoechst 33258 to the Minor Groove of B–DNA", Mol. Biol., vol. 197, pp. 257–271, (1987).

Kitchen, A. D., et al., "Effect of Gamma Irradiation on the Human Immunodeficiency Virus . . . " Vox Sang, 1989: 56:223–229.

Brown et al., BBRC, 86:1139–1145 (86).

(List continued on next page.)

OTHER PUBLICATIONS

Lantz, C. H., "Plasmodium berghei" *Experimental Parasitology*, vol. 31 pp. 255–261, (1972).

Firth, W., et al., "Azido Analogs of Acidine", Mutation Research, vol. 81, issued 1981, pp. 295–309.

Piszkiewicz, D., et al., "Virus Inactivation by Heat Treatment of Lyprilized Coagulation Factor Concentrates", Curr. Stud Hematol. Blood Transfus. 56:44–54 (1989).

Brasch, R., "Contrast-Enhances NMR Imaging: Animal Studies Using Gadolinium-DPTA Complex" AJR 142:625–630, Mar. 1984.

Rowley, S. D., "Hematopoietic Stem Cell Cryopreservation: A review of current techniques" J. of Hematotherapy, 1:233–250 (1992).

Lin, L., et al., *Blood*, 74:517–525, (1989).

Bigbee P. et al., J. Forensic Sci 34:1303–1310 (1989).

Myhrvold, V. "Cryopreservation of Sheep Red Blood Cells" *Acta Vet Scand vol. 20, issued 1979, pp. 531–536*.

Grant and Hackh's Chemical Dictionary, p. 320, 1989.

Ganshirt, K., et al., "A five-bag System for Washing Fresh and Frozen Erythrocytes and their preservation", *Vox Sang.*, vol. 26, issued 1974, pp. 66–73.

Pribor, D., "Studies with Dextran 40 in Cryopreservation of Blood" Cryobiology, vol. 10, issued 1973, pp. 93–103.

Sun, I., et al., J. Clin. Microbiology, 8:604–611 (1978).

Espersen, G., et al., "Irradiated Blood Platelet Concentrat Stored for Five Days" *Vox Sang.*, vol. 55, issued 1988, pp. 218–221.

Sigma Chemical Company Catalog, p. 868 (1990).

Phillips, T. L., "Radiation Sensitizers and Protectors", Newer Methods of Cancer Treatment, DeVita, Section 3, pp. 2256–2271.

Dougherty, T., et al., "Photodynamic Sensitizers", Newer Methods Cancer Treatment, DeVita, Section 4, pp. 2272–2279.

METHOD OF INACTIVATION OF VIRAL AND BACTERIAL BLOOD CONTAMINANTS

This is a continuation-in-part of 08/047,749, filed Apr. 14, 1993, which is a continuation in part of Ser. No. 07/825,691, filed Jan. 27, 1992, now abandoned, which is a continuation-in-part of Ser. No. 07/685,931, filed Apr. 16, 1991, now abandoned, which is a continuation-in-part of Ser. No. 07/656,254, filed Feb. 15, 1991, now abandoned, which is a continuation-in-part of Ser. No. 07/632,277, filed Dec. 20, 1990, now abandoned, which is a continuation-in-part of Ser. No. 07/510,234, filed Apr. 16, 1990, now abandoned.

FIELD OF THE INVENTION

This invention relates to the general field of biochemistry and medical sciences, and particularly to inactivation of vital contamination of compositions comprising peripheral blood cells (red blood cells, platelets, etc.), plasma protein fractions (albumin, clotting factors, etc.) from collected whole blood, the blood of virally infected persons, ex vivo, media used in the preparation of anti-viral vaccines, and cell culture media such as fetal bovine serum, bovine serum or products derived from these sources. The invention is also applicable to a method for the selective inactivation of cancerous cells.

BACKGROUND OF THE INVENTION

A major concern in the transfusion of donated, stored whole human blood or the various blood cells or protein fractions isolated from whole blood is the possibility of viral contamination. Of particular concern are the blood-borne viruses that causes hepatitis and acquired immune deficiency syndrome (AIDS). While any number of cell washing protocols may reduce the viral contamination load for samples of blood cells, by physical solution of the much smaller virus particles, such washing alone is insufficient to reduce viral contamination to safe levels. In fact, some viruses are believed to be cell-associated, and unlikely to be removed by extensive washing and centrifugal pelleting of the cells. Current theory suggests that safe levels will ultimately require at least a 6 log (6 orders of magnitude) demonstrated reduction in infectious viral titer for cellular blood components. This 6 log threshold may be greater for plasma protein components, especially the clotting factors (Factor VIII, Factor IX) that are administered throughout the life of some hemophilia patients.

Viral inactivation by stringent sterilization is not acceptable since this could also destroy the functional components of the blood, particularly the erythrocytes (red blood cells) and thrombocytes (platelets) and the labils plasma proteins. Viable RBC's can be characterized by one or more of the following: capability of synthesizing ATP; cell morphology; $P_{50}$ values; oxyhemoglobin, methemoglobin and hemichrome values; MCV, MCH, and MCHC values; cell enzyme activity; and in vivo survival. Thus, if lyophilized then reconstituted and virally inactivated cells are damaged to the extent that the cells are not capable of metabolizing or synthesizing ATP, or the cell circulation is compromised, then their utility in transfusion medicine is compromised.

Viral inactivation by stringent steam sterilization is not acceptable since this also destroys the functional components of the blood, particularly the blood cells and plasma proteins. Dry heat sterilization, like wet steam, is harmful to blood cells and blood proteins at the levels needed to reduce viral infectivity. Use of stabilizing agents such as carbohydrates does not provide sufficient protection to the delicate blood cells and proteins from the general effects of exposure to high temperature and pressure.

Methods that are currently employed with purified plasma protein fractions, often followed by lyophilization of the protein preparation, include treatment with organic solvents and heat or extraction with detergents to disrupt the lipid coat of membrane enveloped viruses. Lyophilization (freeze-drying) alone has not proven sufficient to inactivate viruses, or to render blood proteins sufficiently stable to the effects of heat sterilization. The organic solvent or detergent method employed with purified blood proteins cannot be used with blood cells as these chemicals destroy the lipid membrane that surrounds the cells.

Another viral inactivation approach for plasma proteins first demonstrated in 1958 has involved the use of a chemical compound, beta-propiolactone, with ultraviolet (U.V.) irradiation. This method has not found acceptance in the United States due to concern over the toxicity of beta-propiolactone in the amounts used to achieve some demonstrable viral inactivation and also due to unacceptable levels of damage to the proteins caused by the chemical agents. Concern has also been raised over the explosive potential for beta-propriolactone as well.

It is therefore a desideratum to devise an effective viral inactivation treatment for human blood components, which will not damage the valuable blood cells or proteins. The treatment must be nontoxic and selective for viruses, while allowing the intermingled blood cells or proteins to survive unharmed.

There is an immediate need to develop protocols for the deactivation of viruses that can be present in the human red blood cell supply. For example, only recently has a test been developed for Non A, Non B hepatitis, but such screening methods, while reducing the incidence of viral transmission, do not make the blood supply completely safe or virus free. Current statistics indicate that the transfusion risk per unit of transfused blood is as high as 1:100 for Non A, Non B hepatitis, and ranges from 1:40,000 to 1:1,000,000 for HIV, depending on geographic location. Clearly, it is desirable to develop a method which inactivates or removes virus indiscriminately from the blood.

Contamination problems also exist for blood plasma protein fractions, such as plasma fractions containing immune globulins and clotting factors. For example, new cases of non A, non B hepatitis have occurred in hemophilia patients receiving protein fractions containing Factor VIII which have been treated for vital inactivation according to approved methods. Therefore, there is a need for improved viral inactivation treatment of blood protein fractions.

The present invention thus provides a method for the inactivation of viral and bacterial contaminants present in blood and blood protein fractions.

The present invention also provides a method for viral or bacterial decontamination of frozen or lyophilized cells, recombinant protein preparations, blood components including red cells, platelets and leukocytes, stem cells, protein solutions or other frozen or lyophilized compositions intended for subsequent in-vivo use such as plasma derived factors. The present invention involves utilization of sensitizers which bind selectively to a viral nucleic acid, coat protein or membrane envelope. The sensitizer is also moiety which can be activated upon exposure to radiation, which may be in the form of ultra-violet radiation or ionizing radiation, such as X-rays, which can penetrate the sample containing the contamination. Damage to cells in lyophilized preparations by hydroxy radicals is minimal due to the absence of water molecules. However, while not intending to be limited to a particular theory, in frozen cell or protein containing compositions, some of the water is present in the form of ice but there is also unfrozen water trapped in a highly viscous glassy state. Water with molecules which are present in these glassy states have low mobility and may possibly form hydroxy radicals which can randomly damage cells. However, due to the low mobility in the glassy state, damage to cells from these hydroxy radicals is reduced. Therefore, by irradiating a frozen suspension of cells containing the sensitizers, random damage of the cells due to the hydroxy radicals may be avoided due to the inability of the sensitizer to migrate in the frozen suspension and the inability of the hydroxy radicals to form and migrate through the frozen suspension. In this manner, damage is localized on the targeted viral or bacterial particle.

The present invention is also applicable to inactivation of blood-borne bacterial contaminants, and to blood-borne parasitic contaminants, since such infectious organisms rely on nucleic acids for their growth and propagation. Since purified blood plasma protein factions are substantially free of human nucleic acids, and mature human peripheral blood cells, particularly red blood cells and platelets lack their own genomic DNA/RNA, the use of nucleic acid-binding sensitizers is especially useful for the problem of treating blood contaminants.

SUMMARY OF THE INVENTION

The present invention provides a method for viral/bacterial inactivation of dried (lyophilized or evaporatively dried), frozen, liquid or reconstituted cells (erythrocytes, platelets, hemosomes and other cellular or cell-like components) or blood protein fractions, which allows for the cells or protein fractions to be useful in a transfusable state, while still maintaining relatively high cell viability, ATP synthesis and oxygen transport, in the case of cellular components, and therapeutic efficacy, in the case of protein fractions.

The present invention provides a method for reducing viral, bacterial and other parasited contamination in a composition comprising blood, a blood component, cell culture or a component of cell culture comprising the steps of mixing the composition containing or suspected of containing contamination in a liquid state with a chemical radiation sensitizer capable of binding to the viral, bacterial or parasitic contaminants, wherein the sensitizer comprises a lipophilic moiety, a hydrophilic moiety and a photoreactive moiety wherein the sensitizer is capable of being activated by electromagnetic radiation under conditions of sufficient wavelength, intensity and period of exposure to inactivate the contamination and wherein the conditions are also insufficient to produce reactive oxygen species at levels which substantially impair the physiological activity of the composition; then irradiating the composition and sensitizer mixture whereby substantially all of the contamination is inactivated and the physiological activity of the composition is substantially unimpaired. Preferably the lipophilic moiety comprises a linear or ring system of pi-conjugated bonds, the hydrophilic moiety comprises an ammonium or phosphonium group and the photoreactive moiety comprises a halogen. An advantageous feature of these sensitizers is that they preferably bind to DNA or RNA of the contaminants, such as virus, and not to the cells per se. These sensitizers are particularly useful, therefore, for the decontamination of red blood cells and platelets which do not contain any nuclear DNA. For use of such physiological systems, the sensitizers must be water, soluble or at least water miscible. Not intending to be bound by any theory, it is believed that the presence of the hydrophilic moiety as a relatively flat (pi-system) lipophilic part on the sensitizer improves its ability to pass the sensitizer through the membrane of cells of the contaminating organisms.

The lyophilization and reconstitution media according to the present invention may be utilized to lyophilize and reconstitute proteins, particularly, blood plasma protein fractions. The protein fraction may be virally/bacterially deactivated by mixing with a chemical sensitizer, lyophilized (freeze-dried) or frozen, then irradiated. If the lyophilization media of the invention is used, it is contemplated that the constituents of the media also serve to provide some degree of protection of the dry proteins during irradiation.

The present invention utilizes a class of compounds based on 3-carboethoxy psoralens, psoralens, angelicins, khellins and coumarins which contain a halogen substituent and a water solubilization moiety, such as, quaternary ammonium ion or phosphonium ion. It is believed that the substitution of halogen atoms, particularly bromine atoms, on psoralen molecules increases the binding constant of the sensitizer to DNA due to the hydrophobic nature of bromine. It is further advantageous in that only one photon of light is required to activate the brominated sensitizer, whereas two photons are required in sequential order of nonbrominated psoralens to complete classical photoadduct DNA cross linking. Furthermore, bromine is preferred since brominated psoralens are effective in every intercalated site in double stranded DNA, compared to a nonbrominated compound which is effective only at intercalation sites containing uracil or thymine on different strands. Furthermore, it is believed that brominated psoralens are effective against both DNA and RNA viruses, unlike non-brominated psoralen counterparts which are selective to either DNA or RNA viruses.

These materials comprise a relatively low toxicity class of compounds, which can selectively bind to the nucleic acid (single-stranded DNA, double-stranded DNA, or RNA) that comprise the genetic material of viruses. The bound compound can be activated by exposure to radiation, such as ultraviolet radiation (U.V. light of a defined wavelength), or ionizing radiation such as x-rays, after which the activated compound damages the bound viral nucleic acid or viral membranes rendering the virus sterile and non-infectious. Activation of the selectively bound chemical sensitizer focuses the photochemistry and radiation chemistry to the viral nucleic acid or viral membranes and limits exposure to nearby cellular components or plasma proteins.

According to the present invention, a radiation sensitizing chemical compound is added to a liquid suspension of infectious viruses, and the mixture is exposed to U.V. light or ionizing radiation. Assays of viral infectivity demonstrate the effectiveness of the compounds in inactivating the viruses, compared to radiation treatment alone. The present invention is also applicable to frozen or lyophilized and rehydrated blood components, in particular red blood cells, platelets, and plasma protein fractions.

An effective radiation sensitizer must bind specifically to nucleic acids and must not accumulate in significant amounts in lipid bilayers, which are common to viruses, erythrocytes, and platelets. Although there is evidence that psoralens bind to nucleic acids by intercalation, neutral psoralens such as 8-MOP are uncharged and thus also have a high affinity for the interior of lipid bilayers and cell membranes. The present invention thus provides an additional advantage in that the sensitizers do not bind to membranes.

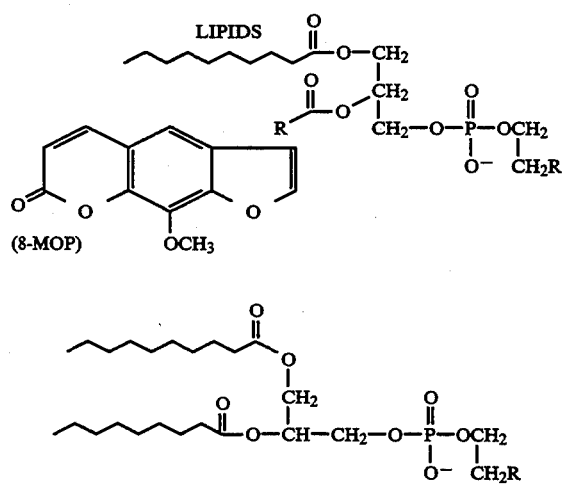

The binding of 8-MOP (8-methoxypsoralen) to cell membranes, shown above, would be acceptable if the psoralen bound to lipid was photochemically inert. However, Midden (W. R. Midden, Psoralen DNA photobiology, Vol II (edi. F. P. Gaspalloco) CRC press, pp. 1. (1988) has presented evidence that psoralens photoreact with unsaturated lipids and photoreact with molecular oxygen to produce active oxygen species such as superoxide and singlet oxygen that cause lethal damage to membranes. Thus, we believe that 8-MOP is an unacceptable sensitizer because it sensitizes indiscriminate damage to both cells and viruses.

Positively charged psoralens such as AMT (4'-aminomethyl-4,5',8-trimethylpsoralen) will not bind to the interior of phospholipid bilayers (membranes) because of the presence of the charge. However, AMT contains an acidic hydrogen which can bind to the phospholipid head group by hydrogen bonding, shown below.

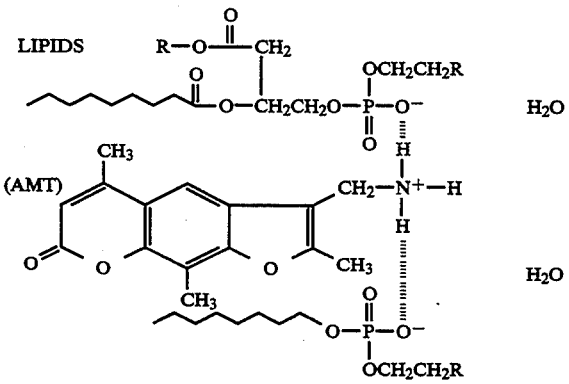

Thus AMT is believed to be an unacceptable sensitizer because it will indiscriminately sensitize damage to viral membranes and to the membranes of erythrocytes and platelets.

The quaternary ammonium or phosphonium substituted halo-psoralens described herein do not accumulate in the interior of lipid bilayers (membranes) because of the presence of the charge, nor will they bind to the phospholipid head groups of the membrane because they lack acidic hydrogen for hydrogen bonding.

In a preferred embodiment, the sensitizer will bear a charge, preferably a positively charged ammonium or phosphonium group, which can impart water solubility to the sensitizer molecule. The positive charge is preferably shielded, however, by substituents on the N or P atom which replace the acidic hydrogen atoms and which sterically shield the charge to disallow electrostatic binding to negatively charged species, such as cell membranes and proteins, to which binding of the sensitizer is undesirable. Thus, since the sensitizer will be bound primarily to target DNA/RNA, and not to cells or proteins, the likelihood of destruction of cells or proteins by the sensitizer upon irradiation is minimized.

The psoralens (such as 8-MOP and AMT) must often be used in combination with a quencher (e.g. mannitol, vitamin E, etc.) to protect, repair or otherwise offset the deleterious effects of the sensitizer and light on cell membranes. The psoralen sensitizers herein do not accumulate in viral membranes and as a consequence do not require the presence of a quencher additive to the blood product.

In solid samples (frozen or lyophilized), a feature of the invention is that radical and radical ions are generated preferably by X-ray activation for advantageous selective viral destruction. The exposure of water and organic molecules to ionizing radiation produces hydroxyl radicals, hydrogen atoms, solvated electrons and organic radicals and radical ions. These are short lived species which react at nearly diffusion controlled rates with proteins and cell membranes. Ultimately these reactions result in cell death or protein denaturation, but according to the invention these chemical reactions are harnessed for viral inactivation.

$$H_2O + X\text{-ray} \rightarrow H_2O+^* + {}^-e^{**} \quad (1)$$

$$^-e^{**} + H_2O \rightarrow H_2O+^* + 2\,{}^-e^* \quad (2)$$

$$^-e^* + H_2O \rightarrow H_2O^* + 2\,{}^-e \quad (3)$$

$$^-e^* + H_2O \rightarrow {}^-e(H_2O) \quad (4)$$

$$H_2O^{+\bullet} + H_2O \rightarrow H_3O^+ + HO^\bullet \quad (5)$$

$$^-e(H_2O) + H_3O^+ \rightarrow H\bullet + H_2O \quad (6)$$

$$^-e(H_2O) + HO^\bullet \rightarrow HO^- \quad (7)$$

When a composition containing red cells, water, and virus is exposed to X-ray radiation, water absorbs essentially all of the incident X-rays due to its presence in large molar excess. X-rays of energy less than about 50 Kev interact with molecules primarily by the photoelectric effect. A water molecule is ionized by an X-ray photon to produce a radical cation and a photoelectron of high energy. The primary photoelectron has enough excess energy to ionize nearby water molecules to produce additional water radical cations and secondary electrons. The secondary photoelectrons have less energy than the primary photoelectrons, but still contain enough energy to ionize nearby water molecules and produce tertiary photoelectrons. The cycle of ionization continues until the energy of the photoelectrons is degraded below the ionization threshold of water. The thermalized photoelectrons are then solvated by water. Water radical cations react with water to form hydroxy radical and hydronium ion (Equation 5).

Solvated electrons react with hydronium ions to form hydrogen atoms (Equation 6). This leads to the creation of hydroxyl radicals (see equation above) and solvated electrons randomly dispersed throughout the sample. These reactive intermediates are then free to diffuse throughout the sample and react indiscriminately with cells and virus. This protocol produces non-selective damage to the virus and cells that are suspended in the solution.

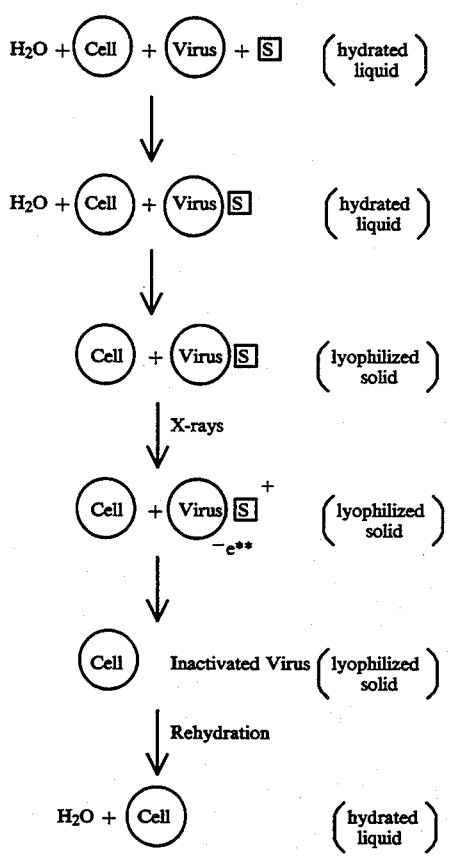

There are several strategic advantages which result from exposure of lyophilized or frozen solid samples to X-rays relative to the exposure of hydrated liquid samples to X-rays. As water is present in molar excess in liquid samples it will absorb the incident X-rays. This results in a random and unselective distribution of reactive intermediates in the sample. The water content in lyophilized samples is greatly reduced and thus the X-ray radiation can now be absorbed by a molecule other than water, in particular, a radiation sensitizer, which is in proximity to the virus and efficiently absorbs X-ray radiation, then the reactive intermediates will be generated in a cluster close to the virus. As there is little diffusion in a lyophilized sample, the reactive intermediates cannot migrate and must undergo reactions in the immediate vicinity in which they are generated. The only reactions possible in the solid state involve the movement of small, light hydrogen atoms and electrons, most likely by quantum mechanical tunneling (QMT). This scheme works equally well in the frozen state. In this case, the water molecules are restricted in their mobility. The most likely pathway for reaction for them involves the recombination of the radicals generated to form the neutral parent molecule. In the frozen system as well, the diffusion of reactive species is limited.

All atoms have a cross section for the absorption of X-rays. In general the larger the atomic number (Z) of the atom, the larger the cross section of the atom to high energy radiation. Secondly, the higher the energy of the X-ray photon, the smaller the cross section of the atom to radiation. Thus, a bromine atom absorbs X-rays more strongly than carbon, nitrogen, or oxygen atoms. X-rays of very high energy (>100 Kev) penetrate samples deeply because they have a small probability of absorption by a particular type of atom. For this reason high energy, deeply penetrating X-rays, are less selectively absorbed by a heavy atom such as bromine relative to a light atom such as carbon, nitrogen, or oxygen. Soft X-rays (<35 Kev) penetrate samples less deeply than hard X-rays (>100 Kev) but are more selectively absorbed by heavy atoms relative to light atoms.

The cross section (Mass Attenuation Coefficient) ratios of platinum to carbon, bromine to carbon, and iodine to carbon as a function of the X-ray source atom are shown in FIG. 1. These values suggest that Mo, Rb, Pd, and Ag X-ray target tubes could produce suitable wavelength radiation to provide a dramatic selectivity in X-ray cross section for bromine or platinum compared to carbon. The selective absorption of X-ray radiation for bromine and platinum peaks with a molybdenum source as opposed to the widely used tungsten source available in most industrial or medical X-ray units.

In view of the mechanism believed to be operative for the sensitizers according to the present invention connection with DNA or RNA, the sensitizer according to the present invention may be activated at wavelengths and intensities which should reduce the production of singlet oxygen or other highly reactive oxygen species. Thus, it is a particular advantage of the present invention to be able to eliminate the use of additives such as ascorbate, sodium thionite, and the like, which scavenge for singlet oxygen or other highly reactive oxygen species which would otherwise substantially impair the physiological activity of the cells, platelets or other desirable components of the composition which is being treated. Furthermore, in some embodiments of the present invention the treated composition may be directly reintroduced into the living subject, thus, the addition of another chemical species, i.e., an oxygen-scavaging species, could have adverse effects on the recipient subject.

The preferred source of radiation for viral inactivation is the combination of the soft X-rays produced from a molybdenum X-ray tube with a polybrominated radiation sensitizer. The bromine atom K-shell absorption edge matches the energy of the characteristic X-ray emission spikes of the molybdenum tube thereby allowing selective deposition of the X-ray energy into the sensitizer. When the sensitizer is bound to the virus or in close proximity to it, this will lead to selective viral inactivation.

Exemplary molecules which meet these criteria include brominated psoralen derivatives as described in the appendix I and positively charged porphyrin compounds, appendix II.

Other compounds such as fluorescein derivatives, merocyanine 540, hematoporphyrin, benzoporphyrin, and phthalocyanines may be utilized for this binding capacity upon derivatization to contain halogens or platinum or both (appendix III). These may be activated by UV, as well visible light or X-rays. This feature will permit their use in the solid state where the side reactions (such as generation of singlet oxygen) which hampers their use in the liquid state can be avoided or suppressed.

A preferred class of sensitizers are compounds of the formula:

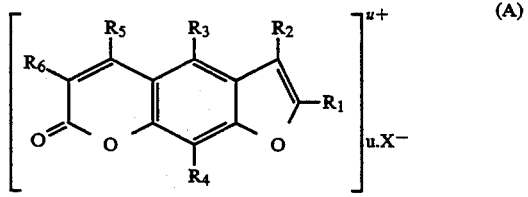
(A)

wherein u is an integer from 1 to 6; X is an anionic counterion; $R_1$, $R_2$, $R_3$, $R_4$, $R_5$, and $R_6$ are independently halo; H; linear or branched alkyl of 1–10 carbon atoms; linear or branched alkoxy of 1–10 carbon atoms;

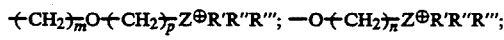

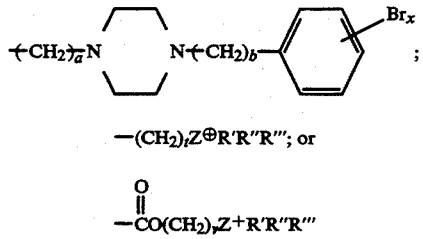

wherein a, b, n, m, p, t and v are independently integers from 1 to 10, X is an integer from 1 to 5 and R', R" and R''' are independently H or linear or branched alkyl of 1 to 10 carbon atoms,

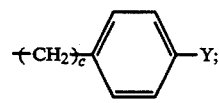

wherein Y is Br, I, F or Cl;

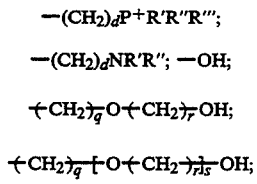

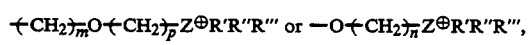

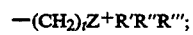

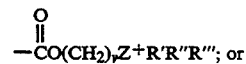

wherein each c, d, q, r and s is independently an integer from 1–10, with the proviso that on each Z atom, not more than one of R', R" or R''' may be H; and at least one of $R_1$, $R_2$, $R_3$, $R_4$, $R_5$, or $R_6$ is

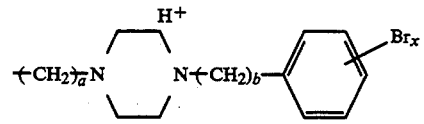

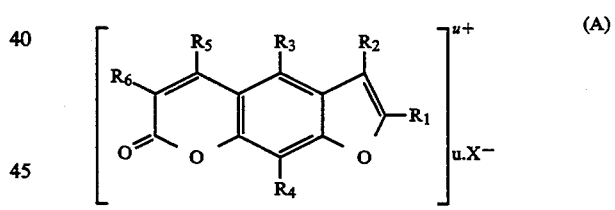

and Z is N or P.

A preferred subclass of sensitizers is selected from the group consisting of compounds of the formula (A):

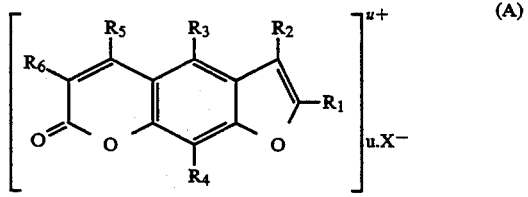
(A)

wherein u is an integer from 1 to 6; X is an anionic counterion; Z is N or P; $R_1$, $R_2$, $R_3$, $R_4$, $R_5$, and $R_6$ are independently halo; H; linear or branched alkyl of 1–10 carbon atoms; linear or branched alkoxy of 1–10 carbon atoms; —(CH$_2$)$_m$O—(CH$_2$)$_p$Z$^\oplus$R'R"R''' or —O—(CH$_2$)$_n$Z$^\oplus$R'R"R''' wherein n, m and p are independently integers from 1 to 10 and R', R" and R''' are independently H or linear or branched alkyl of 1 to 10 carbon atoms with the proviso that on each Z atom, not more than one of R', R" or R''' may be H; and at least one of $R_1$, $R_2$, $R_3$, $R_4$, $R_5$, or $R_6$ is —(CH$_2$)$_m$O—(CH$_2$)$_p$N$^\oplus$R'R"R''' or —O—(CH$_2$)$_n$N$^\oplus$R'R"R'''. Particularly preferred are compounds wherein $R_4$ is —O—(CH$_2$)$_n$N$^\oplus$R'R"R''', especially wherein R', R" and R''' are ethyl and n=3. Preferably, $R_6$, $R_5$, $R_2$ and $R^1$ are hydrogen and $R_3$ is H or halo, preferably bromo.

Particularly preferred compounds are those wherein $R_4$ is —O—(CH$_2$—)$_n$N$^+$R'R"R''', in particular wherein R', R", and R''' ethyl, and n=3.

Another preferred compound is that in which R', R", and R''' are in n-propyl.

Preferably $R_1$, $R_2$, $R_5$ and $R_6$ are hydrogen and $R_3$ is halo, preferably bromine.

Other preferred sensitizers are compounds of the formula:

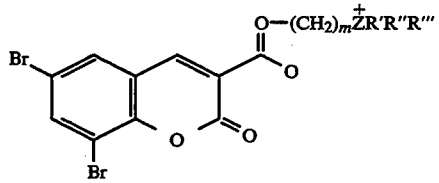

wherein Z is N or P, m is an integer from 1 to 10; and R', R" and R''' are independently H or linear or branched alkyl of 1 to 10 carbon atoms,

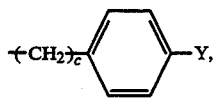

wherein Y is Br, I, F or Cl;

$-(CH_2)_d NR'R''$, $-OH$;

$+CH_2\!\!+_q\!\!O\!\!+\!CH_2\!\!+_r\!OH$;

$+CH_2\!\!+_q\!\!+\!O\!\!+\!CH_2\!\!+_r\!\!+_s\!OH$;

wherein each c,d,q,r and s is independently an integer from 1-10.

Another class of sensitizers comprises compounds of the formula:

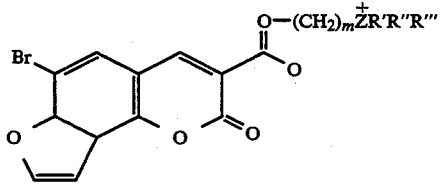

wherein Z is N or P, m is an integer from 1 to 10 and R', R" and R''' are independently H or linear or branched alkyl of 1 to 10 carbon atoms,

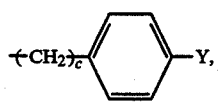

wherein Y is Br, I, F or Cl;

$-(CH_2)_d NR'R''$, $-OH$;

$+CH_2\!\!+_q\!\!O\!\!+\!CH_2\!\!+_r\!OH$;

$+CH_2\!\!+_q\!\!+\!O\!\!+\!CH_2\!\!+_r\!\!+_s\!OH$;

wherein each c,d,q,r and s is independently an integer from 1-10.

Another subclass of psoralen sensitizers comprises compounds of the formula:

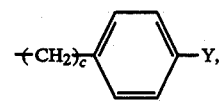

where Z is N or P, m is an integer from 1 to 10 and R', R" and R''' are independently H or linear or branched alkyl of 1 to 10 carbon atoms,

wherein Y is Br, I, F or Cl;

$-(CH_2)_d NR'R''$, $-OH$;

$+CH_2\!\!+_q\!\!O\!\!+\!CH_2\!\!+_r\!OH$;

$+CH_2\!\!+_q\!\!+\!O\!\!+\!CH_2\!\!+_r\!\!+_s\!OH$;

wherein each c,d,q,r and s is independently an integer from 1-10.

Sensitizers also include compounds of the formula:

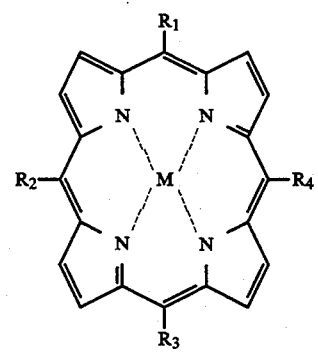

wherein M is H, Pt and $R_1$, $R_2$, $R_3$ and $R_4$ are independently selected from a group consisting of

wherein X = Br, I, Cl, F;

wherein n, m, p are integers from 1 to 10;

and

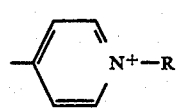

wherein R = alkyl 1 to 6 carbon atoms.

Other sensitizers are compounds of the formula:

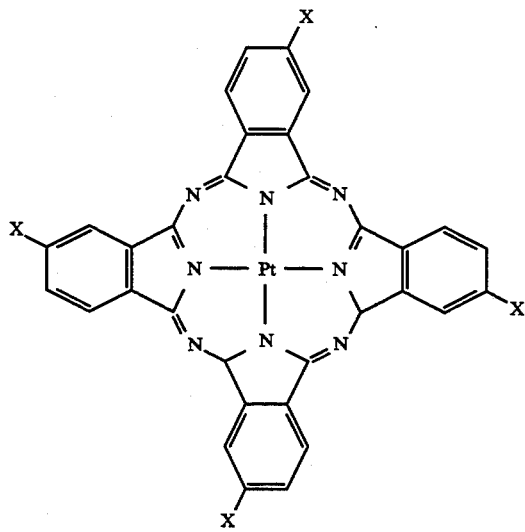
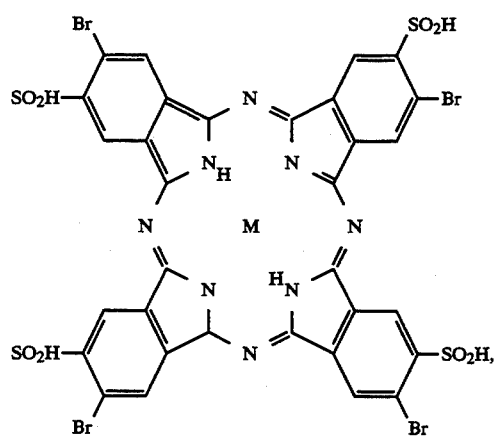
or
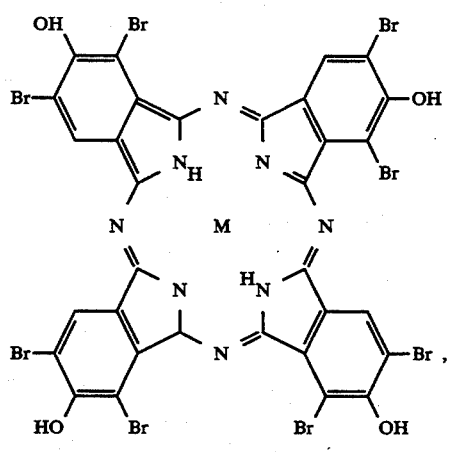
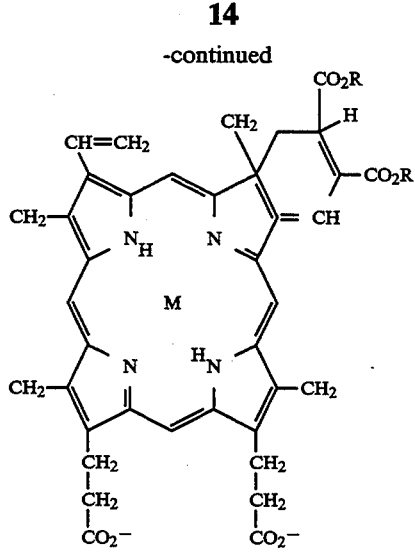
wherein M is H or Pt and R is
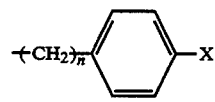
wherein n is an integer from 1 to 10, and X is Br, Cl, I or F.
The sensitizer may also be a compound of the formula:
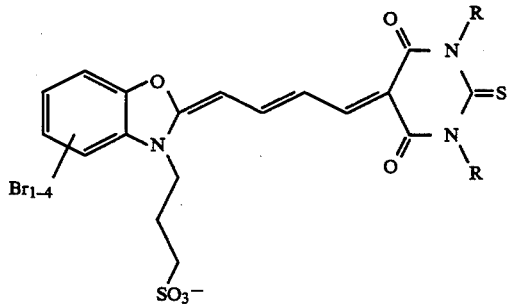
wherein R is alkyl of 1 to 6 carbon atoms,
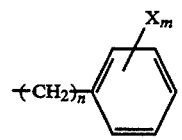
wherein X is H, Br, I, F, or Cl, n is an integer from to 6, m is an integer from 1 to 5; or a compound of the formula:
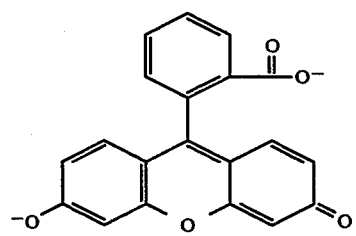

15
-continued

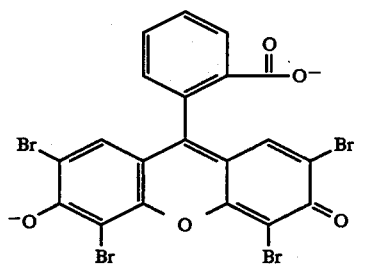

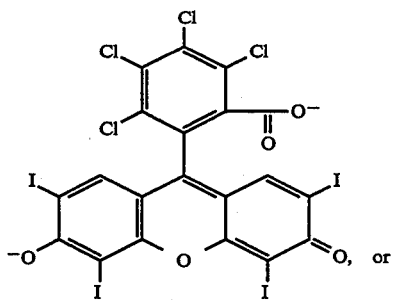

a compound of the formula

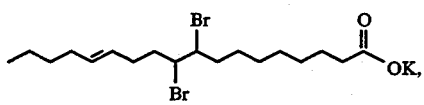

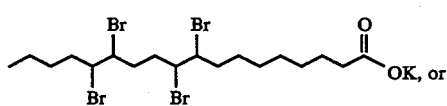

16 a compound of the formula

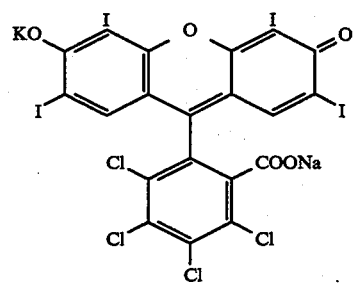

or

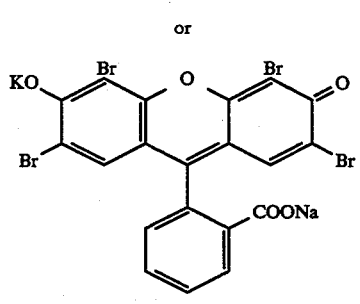

In general, the above compounds may be made by halogenating psoralens and isolating the appropriately substituted isomers. For compounds wherein the ring substituent is a quaternary ammonium alkoxy or phosphonium alkoxy group, that group may be made from the corresponding hydroxy-substituted psoralen, as exemplified by the following scheme.

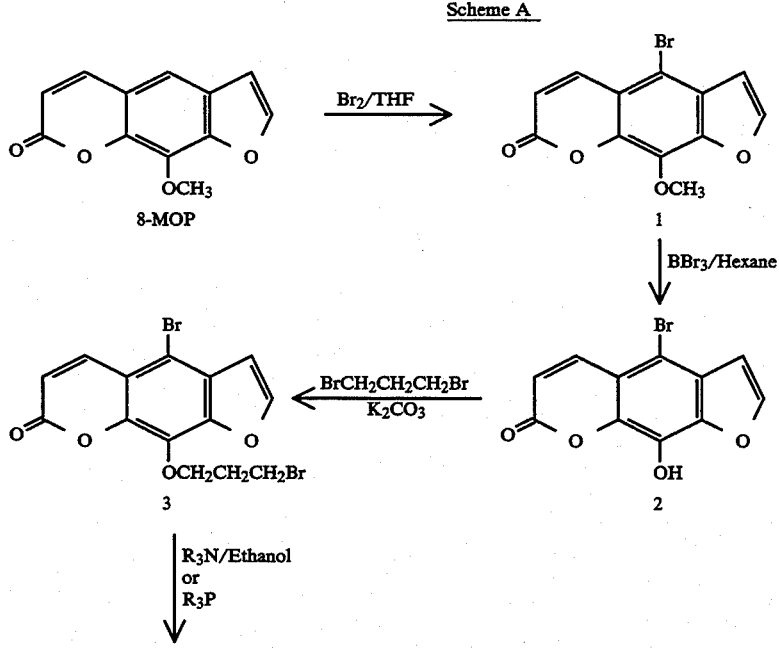

-continued
Scheme A

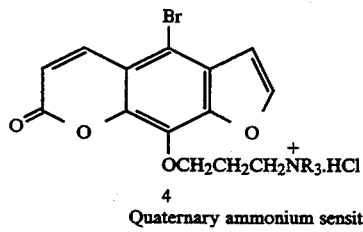

4
Quaternary ammonium sensitizers

Sensitizer 8B  R = —C₂H₅
Sensitizer 8QA  —CH₃

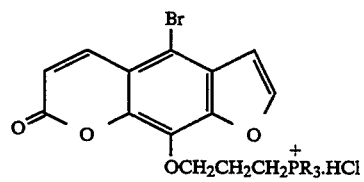

Phosphonium sensitizers

In general, derivatives possessing more than one free hydrogen atoms on the preferred ammonium group show viral inactivation but unacceptable levels of cell damage. This is particularly the case for 4'-aminomethyl-4,5',8-trimethylpsoralen (AMT) which is an experimentally utilized psoralen derivative.

Therefore, according to the invention, sensitizing compounds for viral inactivation preferably do not contain substituents which possess free hydrogen groups capable of exhibiting hydrogen bonding to the cell membrane.

In general methods of preparing substituted psoralen compounds are known, as are methods of preparing derivatives of phthalocyanines, merocyanines and fatty acids. The tetracyclic biological dyes may be made by condensation methods, known to those in the dye art.

In one embodiment, the present invention is applicable to lyophilized cells. The term lyophilization is broadly defined as freezing a substance and then reducing the concentration of the solvent, namely water, by sublimation and desorption, to levels which will no longer support biological or chemical reactions. Usually, the drying step is accomplished in a high vacuum. However, with respect to the storage of cells and particularly erythrocytes, the extent of drying (the amount of residual moisture) is of critical importance in the ability of cells to withstand long-term storage at room temperature. Using the procedure described herein, cells may be lyophilized to a residual water content of less than 10 weight %, preferably less than 3%, and still be reconstituted to transfusable, therapeutically useful cells. Cells with about 3 weight % water content using this procedure may be stored for up to two weeks at room temperature, and at 4° C. for longer than eight months, without decomposition. This far exceeds the current A.A.B.B. standard for refrigerated storage of red blood cells of six weeks at 4° C. or less than one day at room temperature without decomposition. These dried cells may be deactivated using a chemical sensitizer described herein.

According to the embodiment of the present invention for treating dried or lyophilized cells, the washed, packed cells are mixed with a chemical sensitizer, then washed to remove excess sensitizer not bound to viral or bacterial nucleic acid, and the treated cells are then dried or lyophilized. The dry cell and sensitizer mixture will then be irradiated, typically with gamma radiation, at an intensity of about 3K–50K rads, for a period of time sufficient to destroy viruses (in particular, the single-stranded or double-stranded RNA/DNA viruses), without any substantial adverse effect on the recovery and usefulness of the cells. Other wavelengths of electromagnetic radiation such as visible light or X-rays, may be used.

In another embodiment, the chemical sensitizers may be added to liquid protein preparations, then lyophilized and irradiated. Particularly preferred are blood protein preparations, including but not limited to, plasma proteins, blood protein extracts, clotting factors (such as Factors VIII and IX), immune globulins and serum albumin.

Dry or lyophilized cells or protein fractions may be directly mixed with the chemical sensitizer, then irradiated.

From the foregoing description, it will be realized that the invention can be used to selectively bind a chemical sensitizer to blood-transmitted viruses, bacteria, or parasites. Also monoclonal or polyclonal antibodies directed against specific viral antigens (either coat proteins or envelope proteins) may be covalently coupled with a sensitizer compound.

Since cell compositions also comprise a variety of proteins, the method of decontamination of cells described herein is also applicable to protein fractions, particularly blood plasma protein fractions, including, but not limited to, fractions containing clotting factors (such as Factor VIII and Factor IX), serum albumin and/or immune globulins. The viral and bacterial inactivation may be accomplished by treating a protein fraction with a sensitizer as described herein.

Although described in connection with viruses, it will be understood that the methods of the present invention are generally also useful to inactivate any biological contaminant found in stored blood or blood products, including bacteria and blood-transmitted parasites.

FIGS. 18 through 21 are graphs of platelet characteristics as a function of irradiation time according to the procedure of EXAMPLE 12.

FIGS. 22 through 25 are graphs of platelet characteristics of platelet concentrates seeded with phi 6, irradiated in presence of senstizers 8B and 8C, according to EXAMPLE 12.

Figure 26:
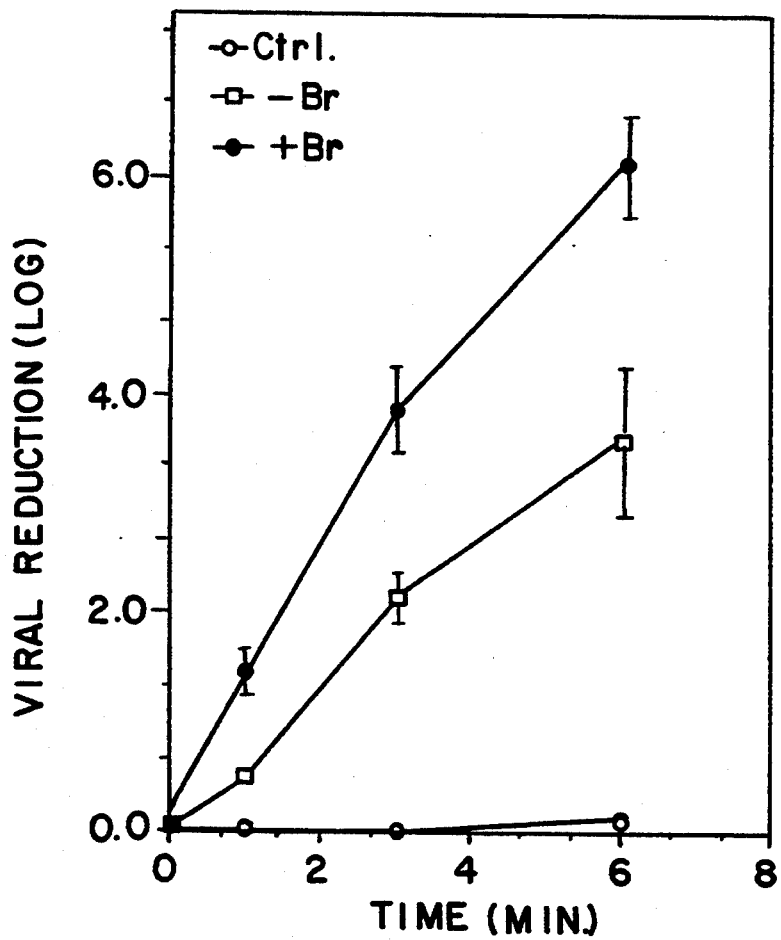

FIG. 26 shows the viral reduction results of the test described in Example 13.

Figure 27:
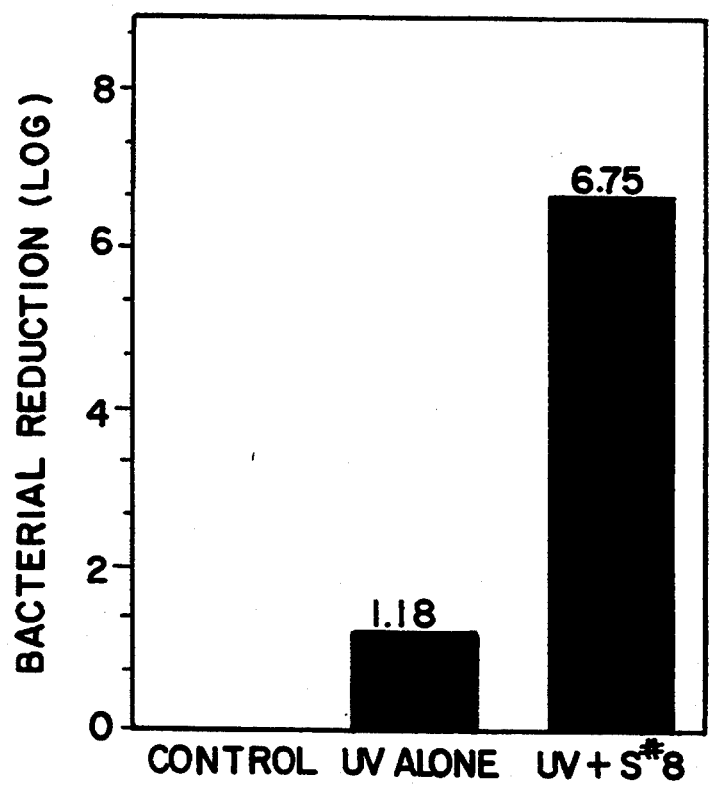

FIG. 27 shows the results of bacterial reduction described in Example 19.

Figure 28:
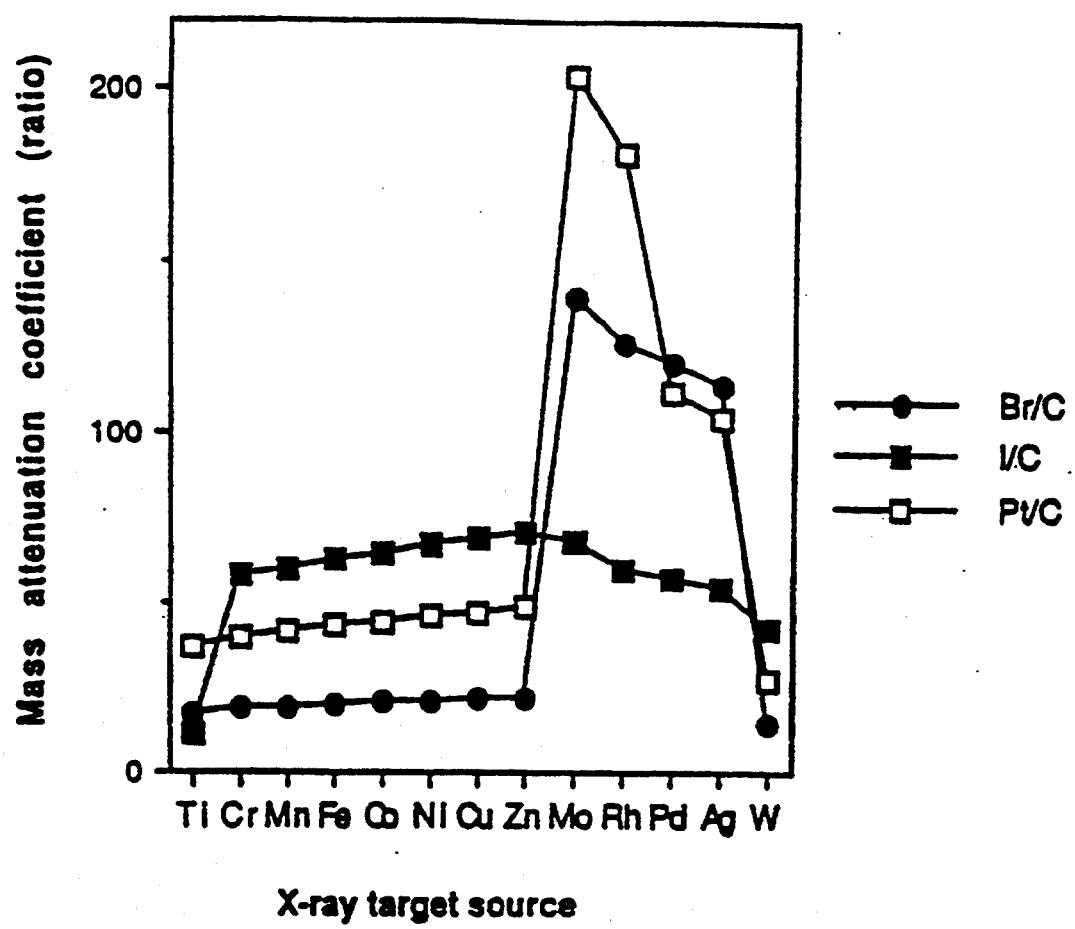

FIG. 28 shows the attenuation coefficients described in Example 21.

Figure 29:
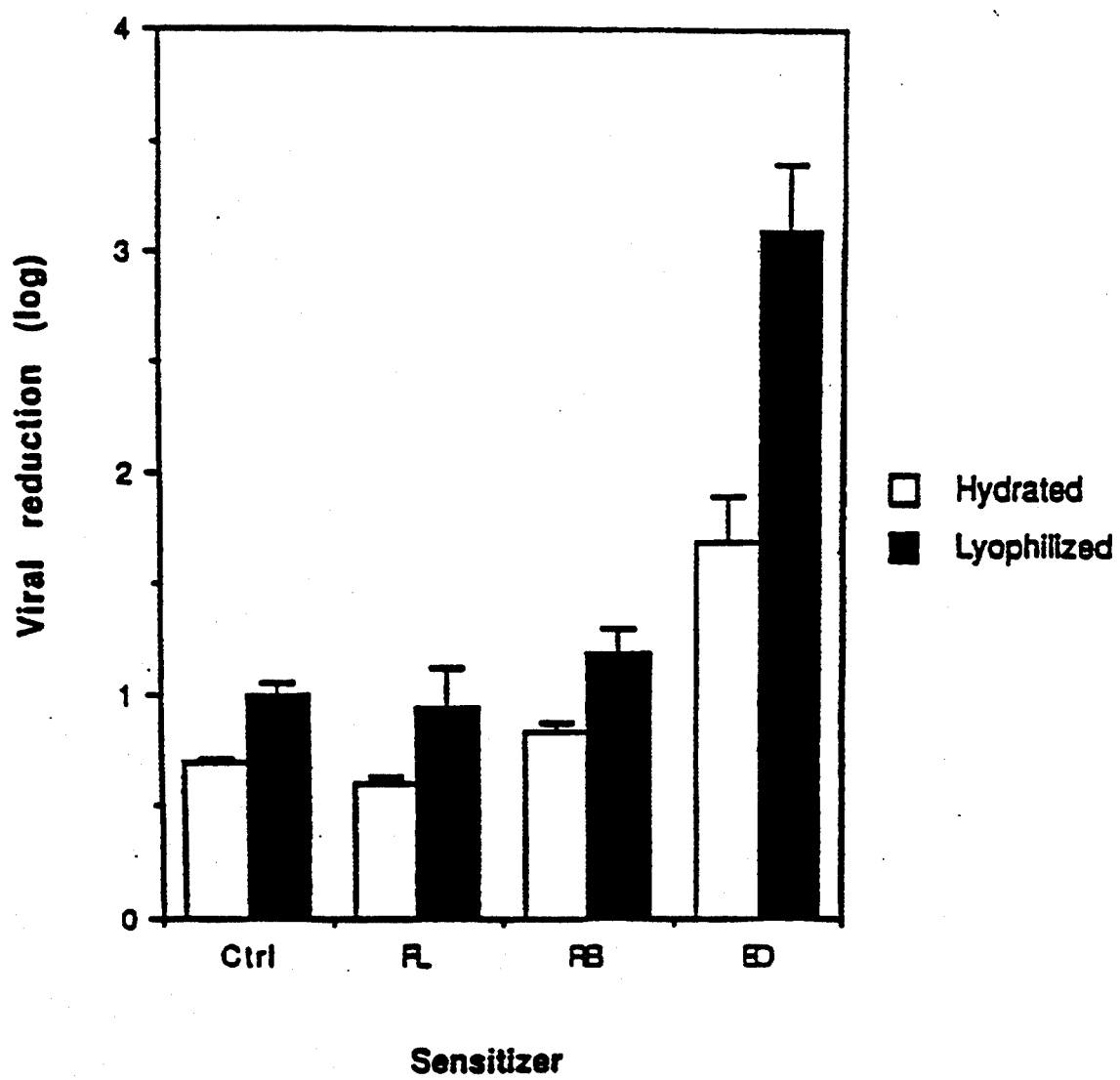

FIG. 29 shows results of the test described in Example 22.

DETAILED DESCRIPTION OF THE INVENTION

The present invention is directed to methods for reducing viral, bacterial and other parasitic contamination in blood, blood components, cell cultures or cell culture components by irradiation in the presence of a chemical sensitizer. Sensitizers are disclosed which are particularly useful to decontaminate liquid compositions, such as blood, blood components, reconstituted lyophilized cells, and the like, using UV irradiation. Other sensitizers are disclosed which are particularly useful to decontaminate solid compositions, such as frozen, dried or lyophilized cells or proteins.

LYOPHILIZED OR DRIED CELLS OR PROTEINS

One embodiment involves lyophilized cells (or proteins).

The cells are preferably prepared by immersing a plurality of erythrocytes, platelets and/or hemosomes, etc. in a physiologic buffered aqueous solution containing a carbohydrate, and one or more biologically compatible polymers, preferably having amphipathic properties. By the term amphipathic it is meant there are hydrophobic and hydrophilic portions on a single molecule. This immersion is followed by freezing the solution, and drying the frozen solution to yield novel freeze-dried erythrocytes containing less than 10%, and preferably about 3% or less by weight of moisture, which, when reconstituted, produce a significant percentage of viable, transfusably useful red blood cells, platelets or hemosomes. Preferred methods of reconstitution of the lyophilized composition are described below. Although described in connection with red blood cells, it will be understood that the methods are generally also useful to lyophilize platelets, hemosomes, and blood protein fractions.

The carbohydrate utilized to prepare erythrocyte, platelet and/or hemosome compositions according to the invention is biologically compatible with the erythrocytes, platelets or hemosomes, that is, non-disruptive to the cells or hemosome membrane, and one which permeates, or is capable of permeating, the membrane of the erythrocytes, platelets or hemosomes. It is also advantageous to stabilize proteins, especially labile blood proteins, with the carbohydrates during lyophilization and irradiation according to the invention. The carbohydrate may be selected from the group consisting of monosaccharides, since disaccharides do not appear to permeate the membrane to any significant extent. Monosaccharide pentoses and hexoses are preferred as is a final concentration of from about 7.0 to 37.5 weight % in phosphate buffered saline (PBS) or a phosphate buffered solution, preferably about 26%. Xylose, glucose, ribose, mannose and fructose are employed to particular advantage.

It will be understood that the cells may be lyophilized using other protocols and irradiated as described below. Although viral inactivation will be attained, the advantage of retaining a significant percentage of viable useful red blood cells is lost if the described lyophilization procedure is not followed.

The following description is written in connection with erythrocytes (RBC's) but it will be understood it is also applicable to platelets, hemosomes or other blood cell types or biological cells, as well as protein fractions, particularly plasma protein fractions.

The erythrocytes will preferably be prepared from whole blood centrifugation, removal of the plasma supernatant and resuspending the cells in PBS or a phosphate buffered solution or a commercial dextrosesaline solution. This wash cycle may be repeated 2-3 times preferably using a commercial dextrose-saline solution, then the packed cells are diluted with the lyophilization buffer described above so that the final diluted concentration of carbohydrate and polymer are maintained in the necessary ranges.

Alternatively, commercially available packed blood cells may be used, which typically are prepared in CPDA (commercial solution containing citrate, phosphate, dextrose and adenine).

Preferably, but not necessarily, the cells will have been previously lyophilized using a lyophilization solution buffered in the range of pH of 7.0 to 7.4 preferably by a phosphate-buffered solution. A typical phosphate-buffered lyophilization solution will comprise mono- and di-basic potassium and sodium phosphate (usually in the range of 1-10 mM each) and 5-10 mM adenine. This solution maintains the pH at around 7.2.

A preferred phosphate-buffered solution to be used as the lyophilization buffer will comprise nicotinic acid, reduced glutathione, glutamine, inosine, adenine, monopotassium phosphate, magnesium chloride disodium phosphate all of which will serve as a basic salt buffer at a pH of about 7.2. In addition this lyophilization buffer will contain a final concentration of about 26% weight by volume of a monosaccharide, preferably 1.7 M glucose, and a final concentration of about 3.0% weight by volume of polyvinylpyrrolidone (average molecular weight of 360K), and a final concentration of about 15% weight by volume of hydroxyethyl starch (average molecular weight of 500K).

Upon lyophilization to a moisture content of less than 10%, and preferably less than 3%, the lyophilized cells may be maintained under vacuum in vacuum-tight containers, or under nitrogen or other inert gas, at room temperatures for extended periods of time in absence of or without significant degradation of their desirable properties when reconstituted for use as transfusable cells. In using the preferred lyophilization method disclosed herein, a particular advantage of the present invention is that the lyophilized cells may be stored at room temperature for extended periods of time, thus obviating the need for low temperature refrigeration which is required for storing liquid CPDA preserved red blood cells prepared by methods of the prior art. The present invention also obviates the need for very low temperature (−80° C.) frozen storage of red blood cells in glycerol.

By using the preferred reconstitution method disclosed herein it is a further advantage that the lyophilized red blood cells may be reconstituted at normal temperatures, i.e. greater than about 4° C. up to about 37° C., which corresponds to normal human body temperature, and preferably at room temperature (about 22° C.). The reconstitution medium is preferably a solution comprising a polymer or mixture of polymers having a molecular weight of from about 2.5K to 360K, preferably 5K to about 360K, present in a concentration in the range of about 12 to 30% weight by volume. This polymer may be the same polymer utilized to lyophilize the red blood cells as described above. Hence the polymers polyvinylpyrrolidone, hydroxyethyl starch, and dextran are particularly preferred and most preferred is polyvinylpyrrolidone (preferably molecular weight about 10K) present in a concentration of about 19% weight by volume in the reconstitution solution. The reconstitution solution will be buffered again typically by phosphate-buffered solution comprising monopotassium phosphate and disodium phosphate as described hereinabove to maintain a pH within the range of about 7.0 to 7.4. The most particularly preferred polymer is polyvinylpyrrolidone of an average molecular weight of about 10K. The most preferred reconstitution buffer will also contain adenosine triphosphate (ATP) in a final concentration of about 5 mM.

The polymers may be present in the various solutions from a final concentration of about 3.6K weight % up to saturation, and have a molecular weight in the range of from about 2.5K to about 360K. Preferably, the polymers have molecular weights in the range of from about 2.5K to about 500K, most preferably from about 2.5K to 50K, and are present in a concentration of from about 3.6 weight % up to the limit of solubility of the polymer in the solution. Polymers selected from the group consisting of polyvinylpyrrolidone (PVP) and polyvinylpyrrolidone derivatives, and dextran and dextran derivatives provide significant advantages. Most preferred is the use of polyvinylpyrrolidone (an amphipathic polymer) of average molecular weight in the range of 2.5–360K in an amount in the range of 3–20% weight by volume in the solution prior to lyophilization. Amino acid based polymers (i.e., proteins), dextrans or hydroxyethyl starch may also be employed. In the lyophilization buffer hydroxyethyl starch (M-HES) with an average molecular weight of about 500K is employed in a 15% weight by volume final concentration. Other amphipathic polymers may be used, such as poloxamers in any of their various forms. The use of the carbohydrate-polymer solution in the lyophilization of red blood cells allows for the recovery of intact cells, a significant percentage of which contain biologically-active hemoglobin.

The most preferred reconstitution buffer will be a solution comprising monopotassium phosphate, disodium phosphate and ATP, all of which form a basic salt buffer at a pH of about 7.2, which also contains about 19% weight by volume of polyvinylpyrrolidone (average molecular weight about 10K).

The reconstitution solution may also optionally contain a monosaccharide, preferably present in the concentration range of about 7.0 to 37.5% weight by volume. The preferred monosaccharides are xylose, glucose, ribose, mannose and fructose.

In the most preferred embodiment, the lyophilized erythrocytes can be reconstituted by mixing with an equal volume of the reconstitution buffer at a temperature of about 37° C. and mixed. By "equal" it is meant that the volume is the same as the starting volume prior to lyophilization. After initial reconstitution, the solution is preferably diluted 1:1 with 1–4 additional volumes of the reconstitution buffer at a temperature of about 37° C. with added mixing until fully hydrated.

Then, it is preferred that the rehydrated cells be washed according to the following procedure. It is realized, however, that once the cells are reconstituted with reconstitution buffer they are in a hydrated and useful form, but the combination of washings described hereinafter are preferred, specifically for clinical purposes.

After separating the cells from the reconstitution buffer by centrifugation, the resulting packed cells are preferably resuspended at room temperature in (approximately the volume used in the initial reconstitution) a wash buffer comprising nicotinic acid, inosine, adenine, glutamine, and magnesium chloride, all present at about 0.4–10 mM further comprising sodium chloride and potassium chloride each at about 30 mM, buffered by 10 mM disodium phosphate to pH 7.2. This wash buffer further comprises a monosaccharide, preferably glucose at a concentration of about 20 mM, and a polymer, preferably polyvinylpyrrolidone, of a molecular weight 40K and present at a concentration of about 16% weight by volume. Separation by centrifugation completes the first post-rehydration step, a washing step.

After the washing step the rehydrated cells may be suspended in a dextrose-saline transfusion buffer, if transfusion is the intended use of the cells, at room temperature which preferably contains polyvinylpyrrolidone at a 10% weight by volume final concentration, with an average 2.5K molecular weight. The cells can be used as is or be returned to autologous plasma. Additional wash steps in a phosphate-buffered diluent buffer can further remove viruses, but this step is optional for preparation of rehydrated, transfusible cells.

The reconstitution and washings described above will in most instances achieve about 4 log reduction of any viral and bacterial contamination, where 1 log reduction is achieved by drying and 3 log reduction is achieved by washing. Of course, different viruses may respond differently, potentially resulting in more than 4 log reduction of contamination.

The reconstituted cells have characteristics which render them transfusable and useful for therapeutic purposes in that their properties are similar to that of fresh (i.e. not previously lyophilized) red blood cells. Typically reconstituted red blood cells according to the present invention have an oxyhemoglobin content greater than about 90% of that in normal red blood cells. Hemoglobin recovery prior to any washing step is typically in the range of 80 to 85%. The overall cellular hemoglobin recovery including the post-hydration washing steps is about 20 to 30%. The morphology of the reconstituted cells according to the present invention (by scanning electron microscope) typically shows no holes or gaps, and primarily discocytic with some stomatocytic morphology. The oxygen carrying capacity of fresh red blood cells (as measured by $P_{50}$, the oxygen partial pressure at which 50% of the oxygen molecules are bound) was measured to be in the range of about 26 to 28 (average 26.7); with an average Hill coefficient (a measure of the cooperative binding of oxygen molecules to native hemoglobin) of 1.95. The typical $P_{50}$ for erythrocytes lyophilized and reconstituted according to the present invention is about 27.5 (average) with an average Hill coefficient of 2.08. Assays of ATP in the reconstituted cells indicate ATP levels suggesting normal ATP to ADP metabolism. Normal hemagglutination by readily available blood typing antisera of red blood cells made according to the present invention is also typically found.

This lyophilization and reconstitution procedure advantageously and significantly diminishes vital/bacterial contamination in cell-like material (such as hemosomes), and protein fractions. The contamination can be further reduced by the radiation sensitizing and treatment, particularly while the cells or protein fractions are in the dry state.

The starting packed red blood cells or proteins (which may initially be in a liquid or lyophilized state) are mixed with a sufficient amount (based on total wet weight of cells) of a chemical sensitizer. Preferably, in a composition of packed red blood cells (about 10% hematocrit) about 0.1 to 1 mg of the chemical sensitizer will be used per ml of packed cells. Preferably, the mixture will be irradiated with gamma radiation in the range of 3K-50K rads, typically about 3K rads. Preferred exposure is from 1-10 minutes, if using gamma radiation. Alternatively, UV light (320 nm) may be used, particularly for protein fractions. Preferred exposure is from 1-10 minutes, preferably 3 minutes, if using UV radiation. By this irradiation in presence of a sensitizer, there will be about a 6 log reduction of viral and bacterial contamination, based on contamination present prior to washing and irradiation.

The present invention provides a selective method of generating free radicals derived from chemical sensitizers only in the vicinity of viral RNA or DNA. Indiscriminate radiolysis of blood containing virus in a hydrated state produces hydroxyl radical. However, the hydroxyl radical will damage both the red blood cells and associated proteins as well as the viral target. Thus, vital inactivation would be achieved at the sacrifice of red cell viability. Therefore, sensitizers which bind to DNA, RNA, viral coat proteins, and/or viral membranes and which can be selected to generate radicals upon irradiation, are required. Since the radiolysis can be performed in the dry state (preferably less than 10% residual moisture), generation of hydroxyl radicals from water is greatly reduced. In this manner indiscriminate radical damage is further prevented. Exemplary compounds include:

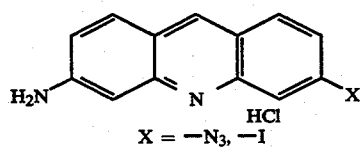
(I)

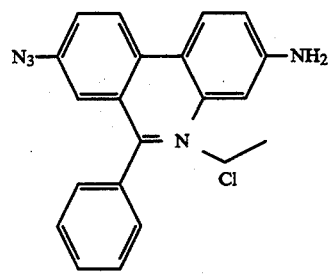
(II)

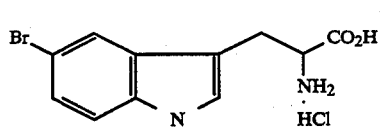
(III)

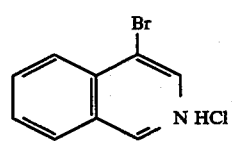
(IV)

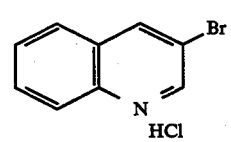
(V)

The preparations of these compounds are known. See Martin, R. F. and Kelly, D. P., Aust. J. Chem., 32, 2637–46 (1979); Firth, W., and Yielding, L. W., J. Org. Chem., 47, 3002 (1982). Other radical-generating reagents which generate radicals upon irradiation are disclosed by Platz et al., Proc. SPIE-Int. Soc. Opt. Eng. 847, 57–60 (1988) and Kanakarajan et al., JACS 110 6536–41 (1988).

The radiation-sensitizing compound (which may also be modified to bear a metal atom substituent) may also be selected from the class consisting of DNA-binding drugs, including, but not limited to, netropsin, BD peptide (a consensus peptide from HMG-1), S2 peptide, and the like. These and other DNA-binding drugs are disclosed in Pjura, P. E., Grzeskowiak, K. and Dickerson, R. E. (1987), J. Mol. Biol. 197, 267–271; and Tengi, M., Usman, N., Frederick, C. A. and Wang, A. H. J. (1988), Nucleic Acids Res. 16, 2671–2690.

The radiation sensitizing compound (which may also bear a metal atom) can also comprise a class of DNA-binding proteins and/or polypeptides and/or peptides. Examples of this class of DNA-binding proteins and/or polypeptides and/or peptides are disclosed in Churchill, M. E. A. and Travers, A. A. (1991) Trends in Biochemical Sciences 16, 92–97. Specific examples of DNA-binding peptides include the SE peptide and BD peptide disclosed in the reference herein.

Another class of sensitizers comprises the positively charged porphorins and pthalocyanates, which bind DNA and RNA. These sensitizers can be activated by irradiation with visible light (500–700 nm).

The DNA-binding specificity can be achieved by covalently coupling the radiation sensitizing compound and/or metal atom to either a DNA-binding drug or to a DNA-binding protein or polypeptide or peptide.

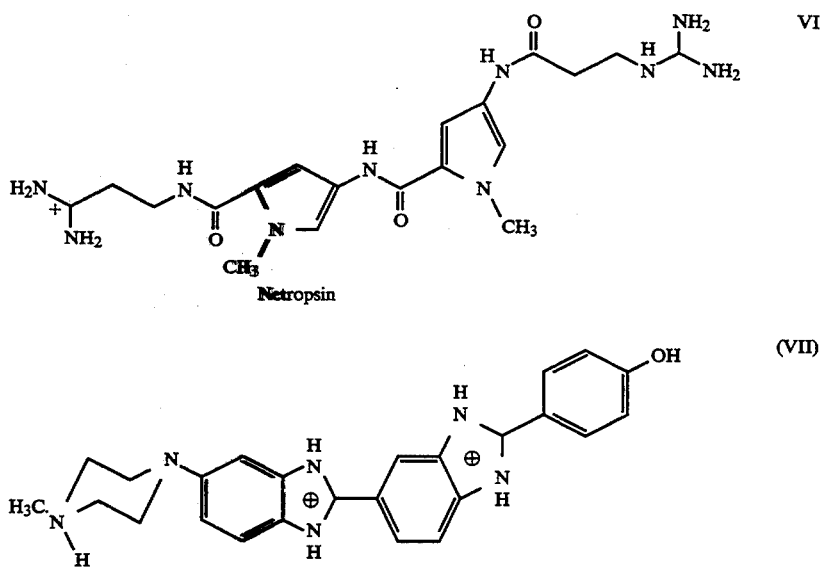

Netropsin (VII)

Other sensitizers include specially designed molecules which form triplex DNA, such as those disclosed by Youngquist and Dervan PNAS 82 2565 (1985); Van Dyke and Dervan, Science 225 1122 (1984); Van Dyke and Dervan, Nuc. Acids Res. 11 5555 (1983); Barton and Raphael, PNAS 82 6460 (1985); Barton et al., JACS 106 2172 (1984); and Barton, PNAS 81 1961 (1984). These molecules bind to DNA and RNA, site specifically, if desired, and carry reactive moieties which can generate free radicals in the proximity of the DNA or RNA.

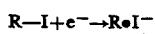

While not intending to be bound by a theory, it is believed that the ejected electron will be captured by that site with the most favorable electron affinity, which is most likely a second molecule of sensitizer elsewhere in the sample. Electron capture by R—I (or R—Br) leads to dissociation of RX with the formation of a radical. The radical so generated will abstract a C—H hydrogen atom from a sugar moiety of a nearby nucleic acid which in turn will lead to DNA or RNA cleavage and viral inactivation.

The radical cation of the sensitizer (R—X+•) will eventually abstract an electron from that component of the sample with the most favorable oxidation potential. This is most likely guanine. The electron transfer reaction forms guanine radical cation. This substance will react with $O_2$ upon reconstitution with aerated $H_2O$. This process also leads to DNA cleavage and viral inactivation. Unreacted material and reaction by-products will be removed during the washing steps involved in the reconstitution of the lyophilized cells. This process will also further remove any virus not inactivated by the treatment described above.

Compounds (1) and (2) bind tightly to DNA and RNA by either intercalation and/or by electrostatic interactions between positively charged ammonium ion groups and the negatively charged phosphate groups of the nucleic acid target. Red blood cells do not contain nucleic acids and accordingly will not bind to such compounds by intercalation.

Dried or lyophilized solid formulations are preferably exposed to 10,000 rads of x-ray or gamma radiation. It is known that the red cells will survive these doses of radiation in the absence of a sensitizer. Lyophilized blood can withstand higher dosage levels of radiation than hydrated blood.

The gamma radiation or x-ray will be absorbed primarily by the heavy atom of the sensitizer, which will be bound to viral DNA or RNA. The radiation will ionize the sensitizer as follows:

In some instances, particularly if the sensitizer and red blood cells are allowed to stand together for more than several minutes, sensitizers may diffuse into the red blood cells prior to lyophilization. Antioxidants such as glutathione (an excellent hydrogen atom donor) may be added to the preparation to augment the red cell defenses against free radical initiated damage. It will be understood that incorporation of the sensitizer into cells will also allow inactivation of intracellular viruses, especially viruses thought to reside inside white blood cells (most packed red blood cell units contain residual white cells), or intracellular blood parasites, such as malaria parasite which infects red blood cells.

The sensitizers are removed from the reconstituted blood serum or protein fraction by the washing protocol described above for lyophilized cells.

It is preferred that gamma or X-ray radiolysis take place in a dried lyophilized blood (or protein), virus, and sensitizer formulation rather than in a wet, fluid material for several reasons. Firstly, the dry material is less sensitive to radiation and can be exposed to larger doses of γ-rays or other penetrating radiation without damage to red blood cells (Table 1). This increases the extent of radiolysis of the sensitizer. Secondly, sensitizer radicals bound to DNA or RNA in the dry state can not dissociate from the virus due to the lack of diffusion in the solid material. This will force the sensitizer radical to react with viral RNA or DNA. Thirdly, the solid state conditions will enhance hydrogen atom transfer reactions of the sensitizer radical with the vital nucleic acid, perhaps by quantum mechanical tunneling.

Fourthly, the reconstitution and washing protocol used with lyophilized blood or protein fraction serves as a means to remove unreacted material or reaction by-products, and further removes any virus not affected by the treatment (Table 2).

Other types of radiation may be used including ionizing radiation in general, such as X-ray radiation. In one embodiment a metal and/or halogen atom may be a substituent on a chemical radiation sensitizer molecule which binds to nucleic acids, thereby targeting the embodiments such as bacteria, parasites and viruses. Metal and halogen atom substituents of chemical sensitizers for this purpose include Pt, Br, I, Zn, Cl, Ca and F. The X-ray source is preferably a tunable source, so that the radiation may be confined to a narrow wavelength and energy band, if so desired. The tunable feature allows for optimization of energy absorption by the metal atoms, thereby directing the absorbed penetrating radiation energy to the production of radicals by a chemical sensitizer bound to nucleic acid.

A preferred metal to be used as the radiation sensitizer is platinum. Another preferred group comprises the halogens, bromine, iodine, chlorine and fluorine. Based on their increasing ability to interact with impinging X-rays, the order of enhancement of radiation sensitizing is expected to be platinum, which is much greater than bromine, which is much greater than iodine, chlorine and fluorine, all of which are much greater than hydrogen.

Compounds containing these atoms, when exposed to X-rays or other forms of ionizing radiation, are capable of forming a reactive species which can interact with the viral nucleic acid, coat protein or lipid envelope, thus destroying it and rendering it non-infectious. This process may be most effective in a dry state where quenching and side reactions due to the presence of water are avoided.

TREATMENT OF LIQUID COMPOSITIONS CONTAINING CELLS OR PROTEINS

If the composition suspected of being contaminated is to be treated in liquid form, i.e., as a suspension of cells or protein solution, it is preferred that the sensitizer be UV-activated. The most preferred sensitizers for this purpose are halogenated psoralens.

Psoralens are naturally occurring compounds which have been used therapeutically for millenia in Asia and Africa. The action of psoralens and light has been used to treat vitiligo and psoriasis (PUVA therapy; Psoralen Ultra Violet A) and more recently various forms of lymphoma.

Psoralen will bind to nucleic acid double helices by intercalation between base pairs; adenine, guanine, cytosine and thymine (DNA) or uracil (RNA). Upon absorption of a UVA photon the psoralen excited state will react with a thymine or uracil double bond and covalently attach to one nucleic acid helix.

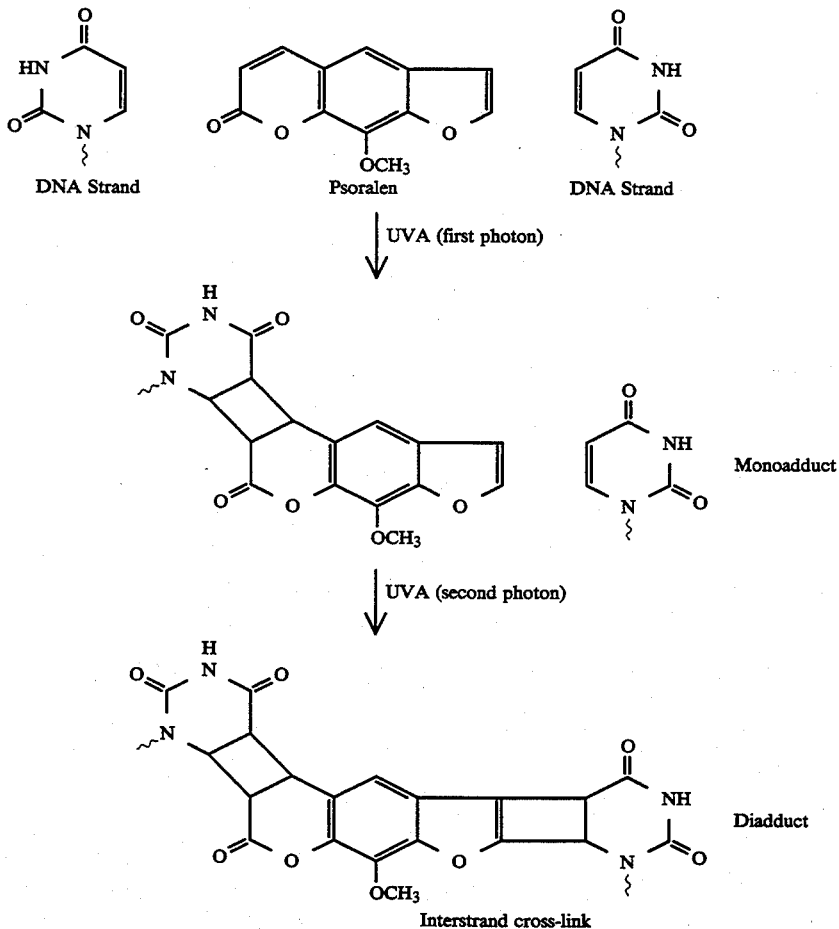

The reaction is specific for a thymine (DNA) or uracil (RNA) base and will proceed only if the psoralen is intercalated in a site containing thymine or uracil. The initial photoadduct can absorb a second UVA photon and react with a second thymine or uracil on the opposing strand of the double helix to crosslink the two strands of the double helix.

Lethal damage to a cell or virus occurs when a psoralen intercalated into a nucleic acid duplex in sites containing two thymines (or uracils) on opposing strands sequentially absorb 2 UVA photons. This is an inefficient process because two low probability events are required, the localization of the psoralen into sites with two thymines (or uracils) present and its sequential absorption of 2 UVA photons.

The halogenated psoralens according to the present invention are improved and more efficient sensitizers because they require only a single UVA photon for activation and the presence of a single guanine base is the only requirement for the site of intercalation. As shown in Scheme 1 absorption of a UVA photon by a bromopsoralen in the presence of guanine leads to electron transfer and the formation of free radicals and ultimately nucleic acid cleavage and viral or cell death.

a quaternary ammonium or phosphonium side chain will reduce the effects of this problem if the maintenance of integrity of the DNA in the cells is desired.

The structures of exemplary chemical sensitizers utilized in accordance with the present invention are listed in Appendix I. The synthesis of the parent heterocycles to these sensitizers are well known.

The best mode for using the invention on liquid samples is to add a UV-sensitive sensitizer to potentially contaminated blood suspensions, and to expose to UV radiation. Fluid solutions of blood are preferably exposed to 3000 rads.

In another embodiment of the present invention the sensitizers will be utilized in conjunction with solvent detergent systems. Such detergents are known to decrease the viral titre of plasma or separated plasma fractions, presumably by dissolution of the viruses. Such detergents include, Tween ®, sodium cholate, sodium deoxycholate, Triton ® and common organic solvents such as ether. Reduction of viral titre by use of these solvent detergents is described for example by

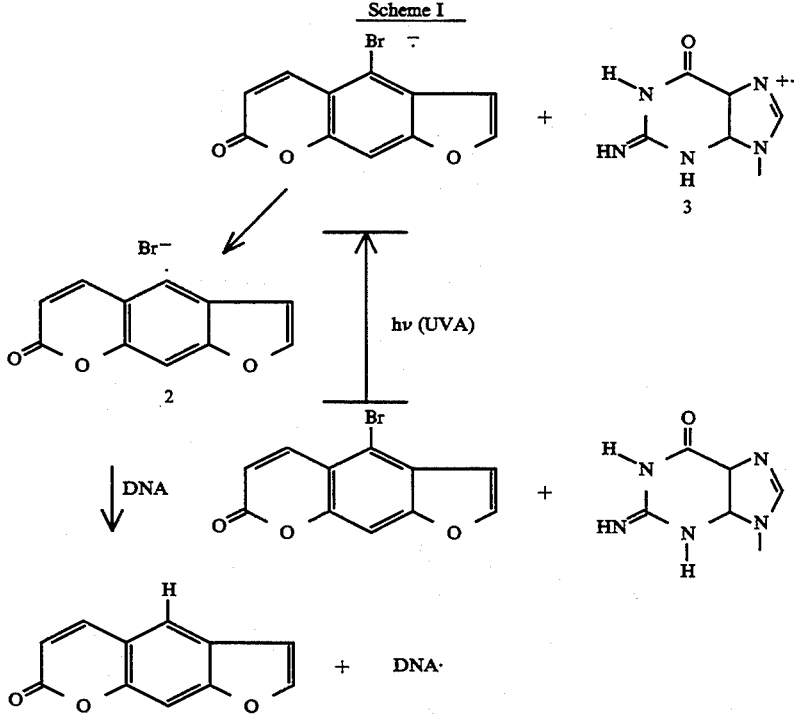

The psoralen radical 2 can inflict damage on the nucleic acid double helix to which it is bonded by abstraction of a ribose (RNA) or deoxyribose (DNA) sugar carbon hydrogen bond. This can lead to DNA cleavage by known mechanisms. The guanine radical cation is also known to react with molecular oxygen, initiating a series of reactions which cleave DNA. The byproduct of the photochemistry is debrominated psoralen 4, which can sensitize DNA cross links as described above.

A disadvantage of PUVA therapy is that it increases the chances of DNA damage (cross linking of the double helix) to normal cells, if normal DNA-containing cells are present in the treated composition. The angelicins, khellins, and coumarins can not cross link DNA because they lack a second double bond or this bond, is located in a position unsuitable for crosslinking. Thus halogenated angelicins, khellins and coumarins bearing Horowitz, et al., Transfusion., 25, (6), 516-522 (1985), and 25, (6), 523-527 (1985); and U.S. Pat. No. 4,946,648. The level of reduction by such solvent detergents may vary as reported in literature to a reduction of one log to greater than five logs of viral titre for such viruses as VSV, Sindbis, and Sandai. The present invention may enhance the reduction of vital titre by these solvent detergents when used in conjunction with the sensitizers and exposure to radiation as set forth herein. While not intending to be bound by a theory, it is believed that the solvent detergents act on the viral proteins or lipid membranes to denature or alter them in a manner which makes them more susceptible to the actions of the sensitizers through the changes induced by the detergents.

A particularly preferred class of sensitizers comprise DNA intercalators, such as hydroxyl, amino methyl, or methyl substituted psoralens, which may be added to plasma or plasma fractions followed by UV radiation to reduce the viral contamination therein. The substituted psoralens are described in U.S. Pat. No. 4,727,027 wherein a reduction of about 4 to 7 logs of viral contamination was obtained with extended exposure to ultraviolet radiation. The proposed mechanism of action is to form a photoadduct between the sensitizer and the DNA or RNA of viral origin, which results in loss of infectivity of the virus. According to the present invention, the reduction of viral contamination can be unexpectedly reduced by utilizing brominated psoralens or other halogenated psoralens. For example, it was observed that the bromopsoralens are about 200,000 times more effective in reducing viral activity when compared to use of their non-brominated counterparts. While not intending to be bound by any theory, it is believed that the mechanism of action of the brominated psoralens may be a free radical generation in the proximity of the DNA or RNA resulting in damage of vital nucleic acids of viruses.

The brominated psoralens are in an improvement over the known psoralens and other substituted psoralens when used as sensitizers because the brominated psoralens are an improvement because only one photon of light is required to activate the brominated sensitizer whereas two photons are required to activate a non-brominated sensitizer. Secondly, a brominated psoralen is effective in virtually every intercalative site, whereas a non-brominated sensitizer is effective only in intercalation sites containing a uracil or thymine on different strands of the DNA or RNA. Thirdly, the brominated psoralens may be activated by X-rays as well as UV light.

The use of the brominated or halogenated psoralens is particularly useful in activation in hydrated systems such as plasma, immune sera, tissue culture media containing animal serum or serum components (such as fetal calf serum), or recombinant products isolated from tissue culture media.

Other types of intercalators may be utilized besides the psoralens and substituted psoralens such as those listed below. These intercalators may be used to target viruses or other blood contaminants, or cancer cells. Thus, halogenated or metal atom-substituted derivatives of the following compounds may be utilized as sensitizers:

dihematoporphyrin esters
hematoporphyrin derivatives
benzoporphyrin derivatives
hydrodibenzoporphyrin dimaleimade
hydrodibenzoporhyrin
dicyano disulfone
tetracarbethoxy hydrodibenzoporhyrin
tetracarbethoxy hydrodibenzoporhyrin dipropionamide The above compounds in their non-halogenated or non-metal atom substituted forms are disclosed in U.S. Pat. Nos. 4,649,151, 4,866,168, 4,883,790, 5,053,423 and 5,059,619, incorporated by reference herein. When modified with halogen atoms or metal atoms, the above-identified classes of compounds may be sensitized with electromagnetic radiation, including visible light.

The present invention may be applied to treatment of liquid blood in ex vivo irradiation, such as by methods and apparatus described in U.S. Pat. Nos. 4,889,129 and 4,878,891.

The above compounds are included in a class named lipophilic dyes which include dyes such as merocyanine 540 and phthalocyanine derivatives. Merocyanine 540 has been disclosed as useful for the treatment of cancer and viral inactivation of blood cells and plasma proteins (Sieber, et al., Photo Chem. and Photo Biology, 46 707–711 (1987)). Phthalocyanine derivatives and other lipophilic dyes are known to bind to the membranes of cancer cells or enveloped viruses. When these compounds are activated with suitable wavelength of electromagnetic radiation, they produce singlet molecular oxygen (Kalyanaraman, et al., PNAS, 84 2999–3003 (1987)), which damages the membrane resulting in the killing of the cancer cells or in viral inactivation. With the addition of radiation sensitizer atoms (metal atoms or halogens) according to the present invention, use of these compounds in combination with suitable radiation produces free radicals in the proximity of the DNA/RNA/viral membranes, when then results in destruction of the viral membranes or nucleic acid to inactivate the virus.

Halogenated or metal atom substituted fatty acids also may be utilized according to the present invention as radiation sensitizers. Fatty acids per se have been used in viral inactivation by Horowitz, et al. as disclosed in U.S. Pat. No. 4,841,023. According to the present invention, these fatty acids may be utilized with sensitizer atoms to target viral membranes in plasma protein solutions, for example, and by subsequent activation with suitable radiation the free radicals are produced to inactivate the viral membrane.

Treatment of biological compositions with detergents are disclosed in U.S. Pat. Nos. 4,820,805 and 4,764,369. The clinical application of psoralens in conjunction with photodynamic treatment is discussed by Adelson, *Scientific American* 50–57 (August 1988).

The following compounds are illustrative of sensitizers which contain or which may be modified to contain metal substituents or halogen substituents in accordance with the present invention:

1. DNA or RNA Target Sensitizers

Psoralen Sensitizers:

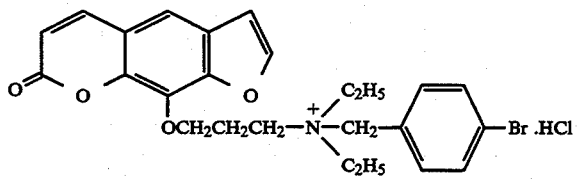

Compound #1

-continued
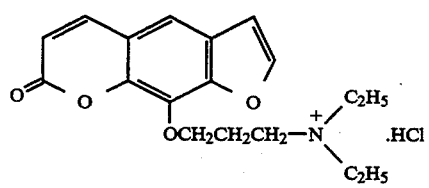
Compound #2
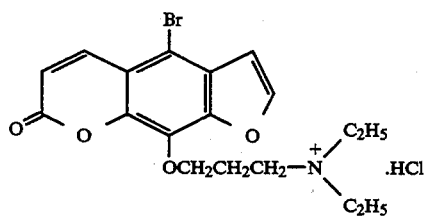
Compound #3
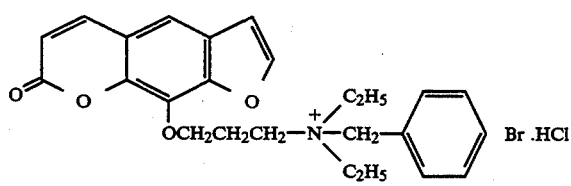
Compound #4
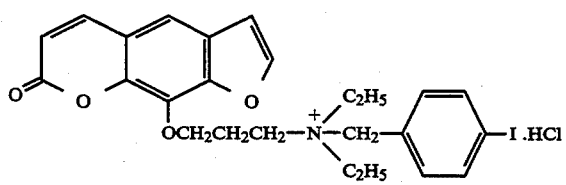
Compound #5
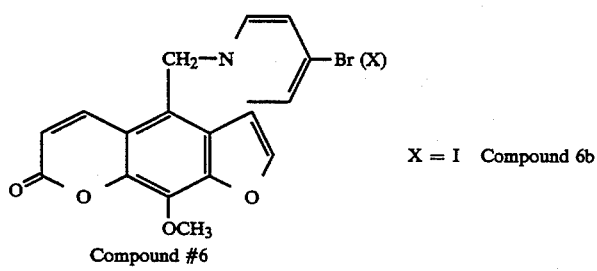
X = I   Compound 6b
Compound #6
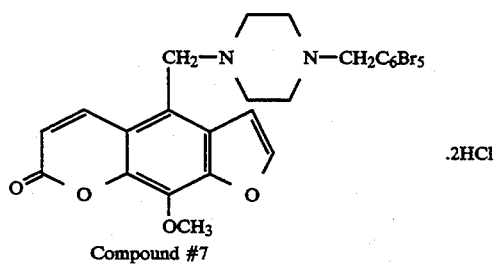
Compound #7
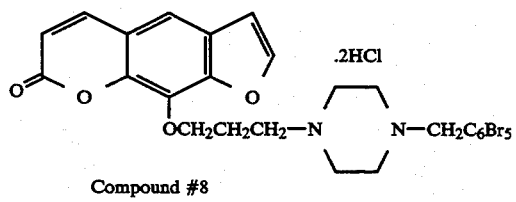
Compound #8

-continued
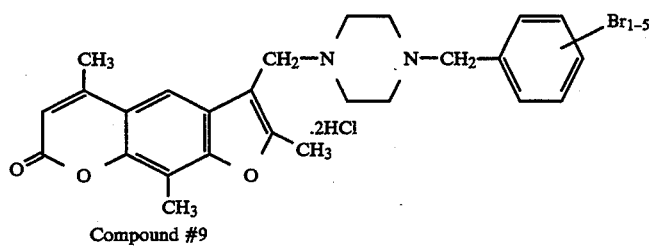
Compound #9
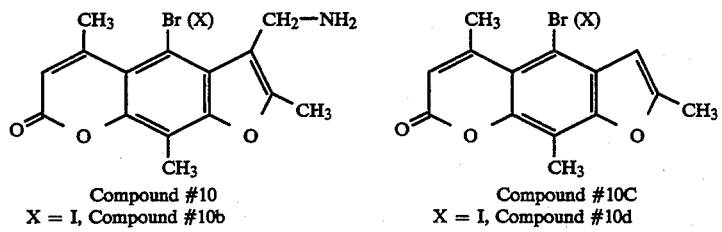
Compound #10
X = I, Compound #10b
Compound #10C
X = I, Compound #10d
2. Membrane Target Sensitizers
Phthalocyanine Sensitizers:
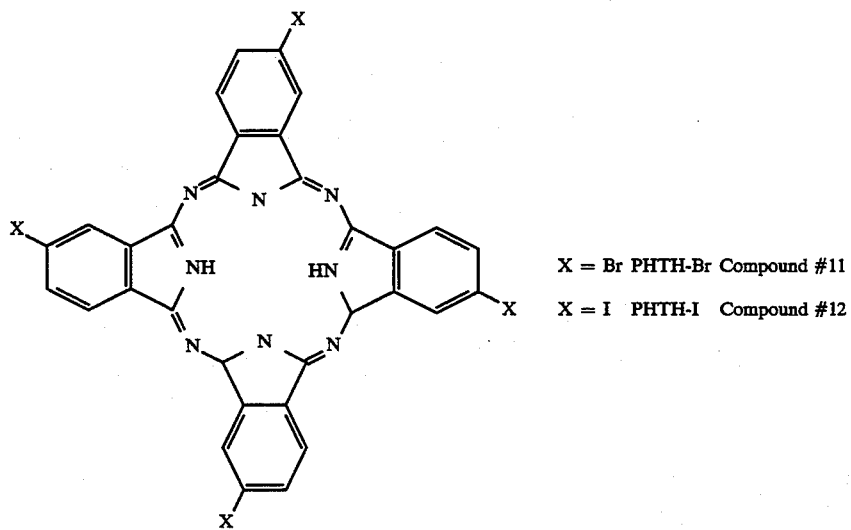
X = Br  PHTH-Br  Compound #11
X = I   PHTH-I   Compound #12
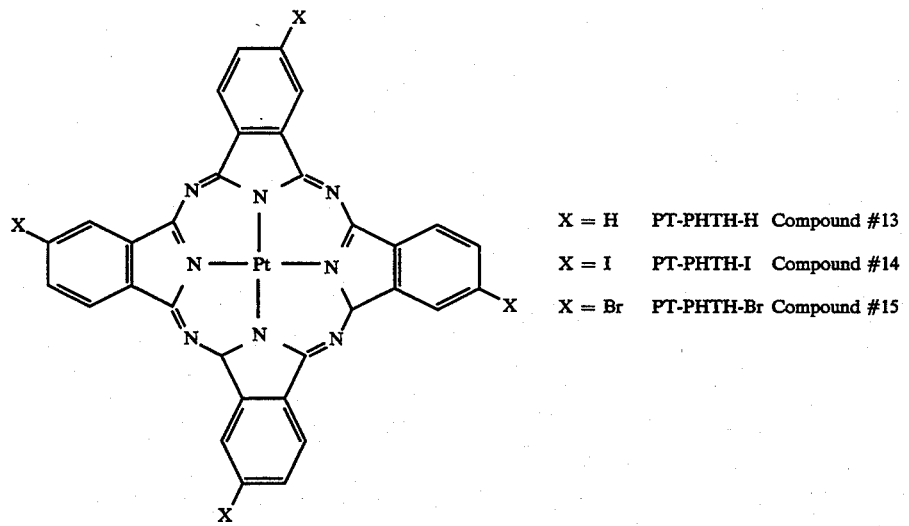
X = H   PT-PHTH-H   Compound #13
X = I   PT-PHTH-I   Compound #14
X = Br  PT-PHTH-Br  Compound #15
Merocyanine Sensitizers:

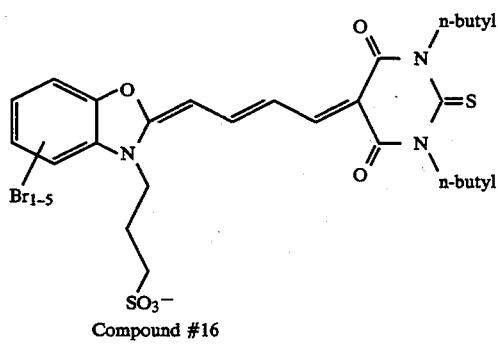
Compound #16

Fatty acid Sensitizers:

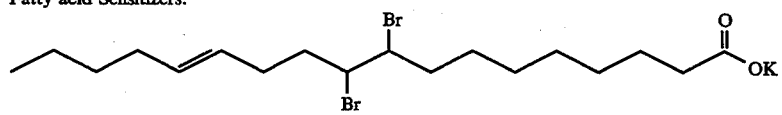
Compound #17

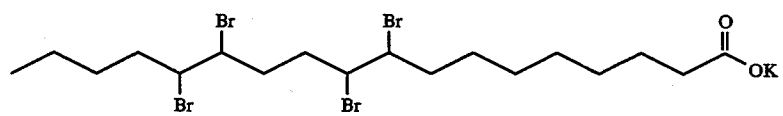
Compound #18

Biological Dyes:

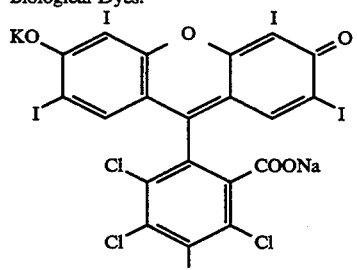
Compound #19

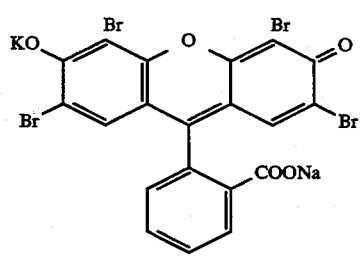
Compound #20

Other sensitizers include compounds such as doxorubicin and daunomycin, which may be modified with halogens or metal atoms in accordance with the present invention, which are known in chemotherapy to attack dividing cells.

The sensitizers also may be utilized in vivo and delivered in liposomes (artificial cells) or drug-loaded natural cells. After introduction of the liposome or drug-loaded cell, the patient may be treated by radiation to activate the sensitizer.

The present invention is applicable to contaminants which comprise single or double-stranded nucleic acid chains, including RNA and DNA, and viruses, bacteria or other parasites comprising RNA and/or DNA.

To illustrate the invention in lyophilized cells, red blood cells were lyophilized as described above, irradiated, and tested for erythrocyte characteristics measured. The results are shown in Table 1. The same procedure was then used, except that the bacteriophage T4 (in dextrose saline) was mixed with the cells and then washed successively with four different wash buffers. The results are shown in Table 2.

TABLE 1

Influence of irradiation on lyophilized reconstituted red blood cells. Doses as high as 20,000–50,000 rads do not affect cells in the dry state according to the parameters assayed after reconstitution and listed below.
Exposure of Lyophilized Cells to Gamma Irradiation

| | *Percentage of Control | |
|---|---|---|
| Dosage Level | 20,000 rads | 50,000 rads |
| Hb Recovery | 100 | 99 |
| Oxy Hb | No Change from | No Change from |

TABLE 1-continued

Influence of irradiation on lyophilized reconstituted red blood cells. Doses as high as 20,000–50,000 rads do not affect cells in the dry state according to the parameters assayed after reconstitution and listed below.
Exposure of Lyophilized Cells to Gamma Irradiation

| Dosage Level | *Percentage of Control | |
|---|---|---|
| | 20,000 rads | 50,000 rads |
| | starting value | starting value |
| Cell Indices | | |
| MCV | 99 | 98 |
| MCH | 100 | 100 |
| MCHC | 100 | 100 |
| Metabolism | | |
| ATP ($\mu$mol/g Hb) | 79 | 79 |
| Lactate ($\mu$mol/g Hb/Hr) | 86 | 79 |

*Control cells were non-irradiated, lyophilized reconstituted cells.

TABLE 2

Reduction in viral titre as a function of washing of the red cells. The procedure used in reconstituting the lyophilized cells involves several washing steps which also reduce the viral titre. The extent of reduction with each wash decreases until a practical limit is attained. This represents an approximate 4 log reduction in viral titre.
Washing Protocol Reduction of Viral Load in Blood

| Buffer Wash Step | Total Amount of Virus | Log Reduction |
|---|---|---|
| Experiment 1 (non-lyophilized cells) | | |
| Reconstitution | $7.30 \times 10^7$ | 0 |
| Wash | $4.80 \times 10^4$ | 3.2 |
| Diluent | $2.08 \times 10^4$ | 3.5 |
| Transfusion | $3.50 \times 10^4$ | 3.3 |
| Experiment 2 (lyophilized cells) | | |
| Lyophilization | $3.68 \times 10^8$ | 0 |
| Reconstitution | $2.11 \times 10^7$ | 1.2** |
| Wash | $2.38 \times 10^4$ | 4.2 |
| Diluent | $2.00 \times 10^4$ | 4.3 |
| Transfusion | $4.06 \times 10^4$ | 4.0 |

In Experiment 1, the effects of lyophilization on viral reduction are not included. In Experiment 2, these effects are included. The marker virus used in these cases was bacteriophage T4. The extent of reduction was determined using the plaque assay.
**This shows an additional about 1 log reduction of contamination due to the drying step.

EXAMPLE 1

Packed human red blood cells purified from donated whole blood are washed free of the anticoagulant storage solution (commercially available CPDA, containing citrate/phosphate/dextrose/adenine), and suspended in dextrose-saline at a 10% hematocrit. Approximately 10 ml of washed packed red cells is placed in a quartz chamber and exposed to U.V. light, preferably at 320 nm, for 2 minute time intervals, up to a 10 minute total exposure. At each 2 minute interval the suspension is mixed and a small sample of red cells (10 microliters) is removed and diluted into 2 ml of water for spectrophotometric assay of hemoglobin. At each step the temperature of the irradiated red cell suspension is measured, to ensure that the suspension did not overheat. At no point did the suspension exceed 26 degrees C. (normal body temperature is 37 degrees C.). Untreated red cells contain a high proportion of functional oxyhemoglobin (oxyHb), usually in the range of 96% or higher.

Oxidation damage can form a semi-stable methemoglobin species (metHb), which can normally be reduced back to oxyhemoglobin by a cellular repair enzyme. Hemichrome represents a more severely damaged form, and can be irreversible. Normal red cells can tolerate a moderate level of methemoglobin. Hemichrome degradation can produce free heme, the iron-porphyrin component of native hemoglobin, which is damaging to cell membranes. Thus it is desirable to minimize hemichrome levels. Each hemoglobin species can be detected at a specific wavelength, using a standard spectrophotometer.

The following data show the sensitivity of the hemoglobin to damage by the increased U.V. exposure.

An exposure of 3 minutes was judged to be usable for viral inactivation using a radiation sensitizer, without inflicting excessive damage to red blood cells.

| EXPOSURE (Minutes) | % OXYHB | % METHB | % HEMI |
|---|---|---|---|
| 0 | 96.6 | 3.4 | 0 |
| 2 | 90.2 | 7.5 | 2.3 |
| 4 | 84.5 | 13.4 | 2.1 |
| 6 | 76.7 | 22.5 | 0.9 |
| 8 | 72.6 | 27.4 | 0 |
| 10 | 66.4 | 33.6 | 0 |

EXAMPLE 2

A suspension (0.1 ml) of bacteriophage lambda or bacteriophage phi-X174, of at least 10EV PFU/ml, is separately added to 4 ml of dextrose-saline containing 1 mg/ml of compounds I or II or III. Each suspension of bacteriophage with a radiation sensitizing compound is then exposed to U.V. radiation of the preferred wavelength (320 nm) in a quartz chamber for the preferred time (3 minutes). A control sample of each bacteriophage suspension, containing a sensitizer, is not exposed to U.V. light. Serial dilutions are performed to quantitate the level of infectious titer, and aliquots of the various bacteriophage samples are then mixed with host bacteria and spread on nutrient agar. Following a normal growth period, the plates are assayed for plaques. Other bacteriophage suspensions are separately irradiated as above, but without added sensitizer, to demonstrate the effect of this dose of U.V. alone.

| COMPOUND | Log10 Reduction of Virus Titer | |
|---|---|---|
| | phi-X174 | Lambda |
| I (X = $N_3$) | >6.0 | >6.0 |
| I (X = I) | 4.0 | >6.0 |
| II | 1.7 | >6.0 |
| No compound | 2–3 | 2–3 |

From these data it can be seen that all three tested compounds significantly increase the sensitivity of double-stranded DNA virus (lambda) to U.V. of the preferred exposure. Compound I is also effective against a single-stranded DNA virus, phi-X174. Compound I is most preferred, showing a high (at least 6 log reduction) inactivation efficacy against both single-strand and double-strand DNA viruses.

EXAMPLES 3

SELECTION OF X-RAY TARGET SOURCE

Figure 1:
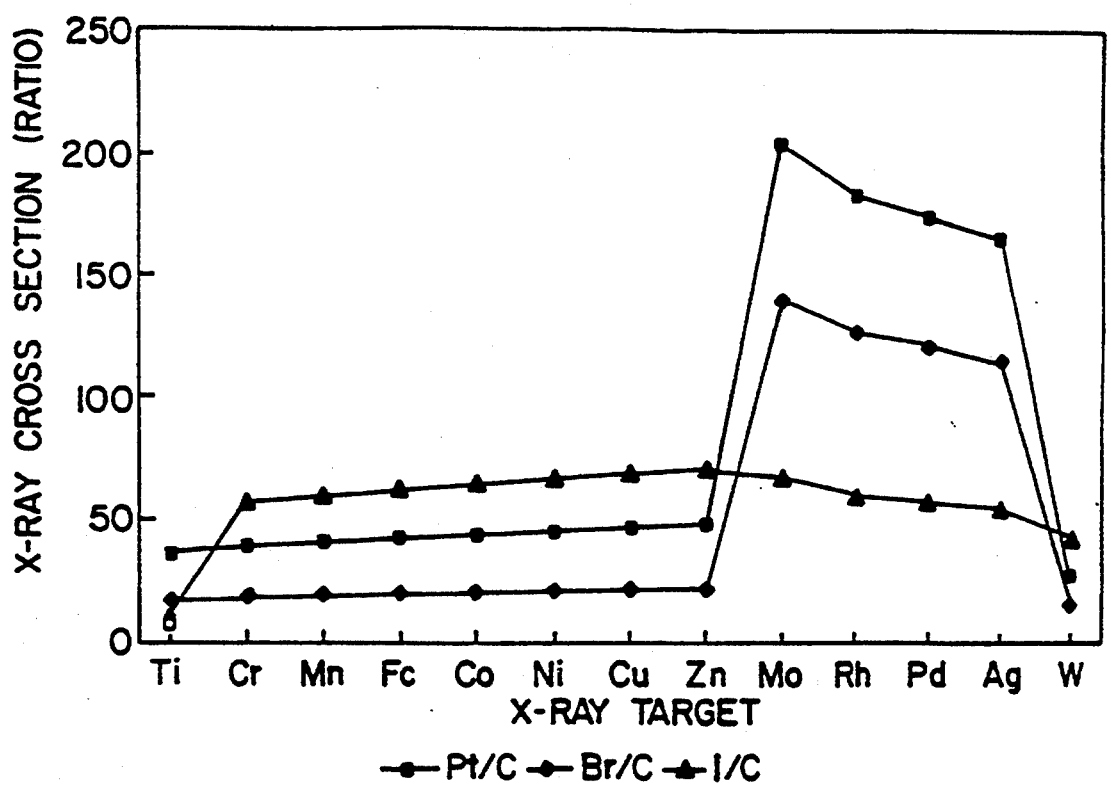
FIG. 1 is a plot of X-ray cross section for various sensitizers described in Example 3.

Referring to FIG. 1, the X-ray cross-section ratios of bromine to carbon, iodine to carbon and platinum to carbon were calculated for their cross-sections in $CM^2/G$ for various X-ray target tubes. Reference: W. H. McMaster, et al. UCRL-50174 Section II, Section III, Section IV, and CRC Handbook of Chemistry and Physics, pp. E147, 1979. The data suggest that Mo, Rh, Pd and Ag X-ray target tubes will produce suitable wave length radiation and selectivity in X-ray cross-sections for sensitizer atoms over the carbon element.

EXAMPLE 4

COMPARISON OF CALCULATED RATIOS OF X-RAY CROSS-SECTIONS

Figure 2:
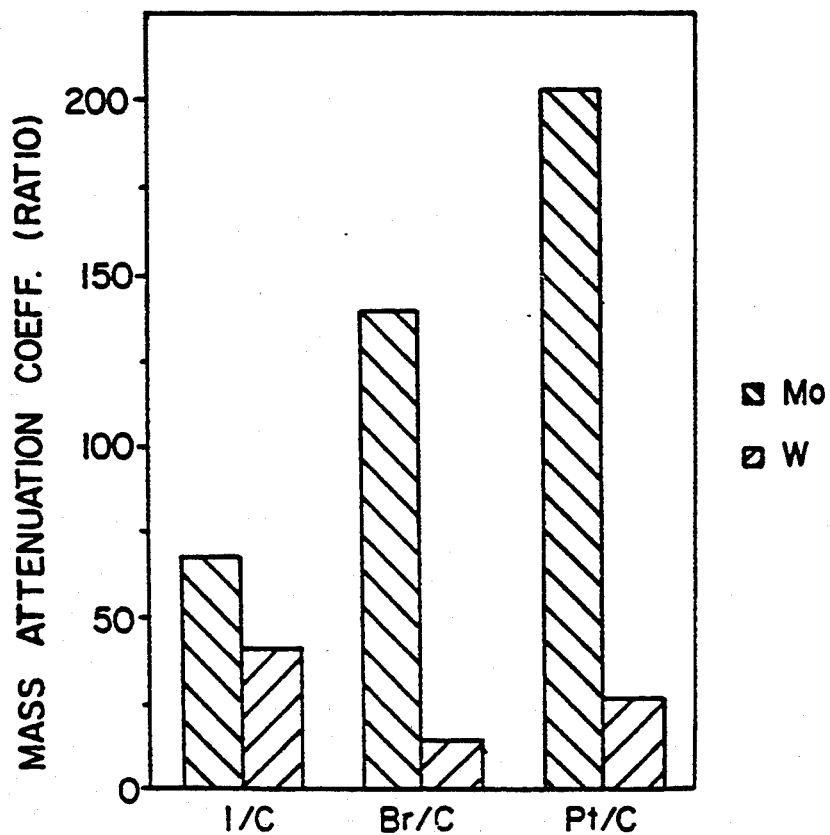
FIG. 2 is a plot of efficiency of sensitizers with Mo and W targets.
Figure 3:
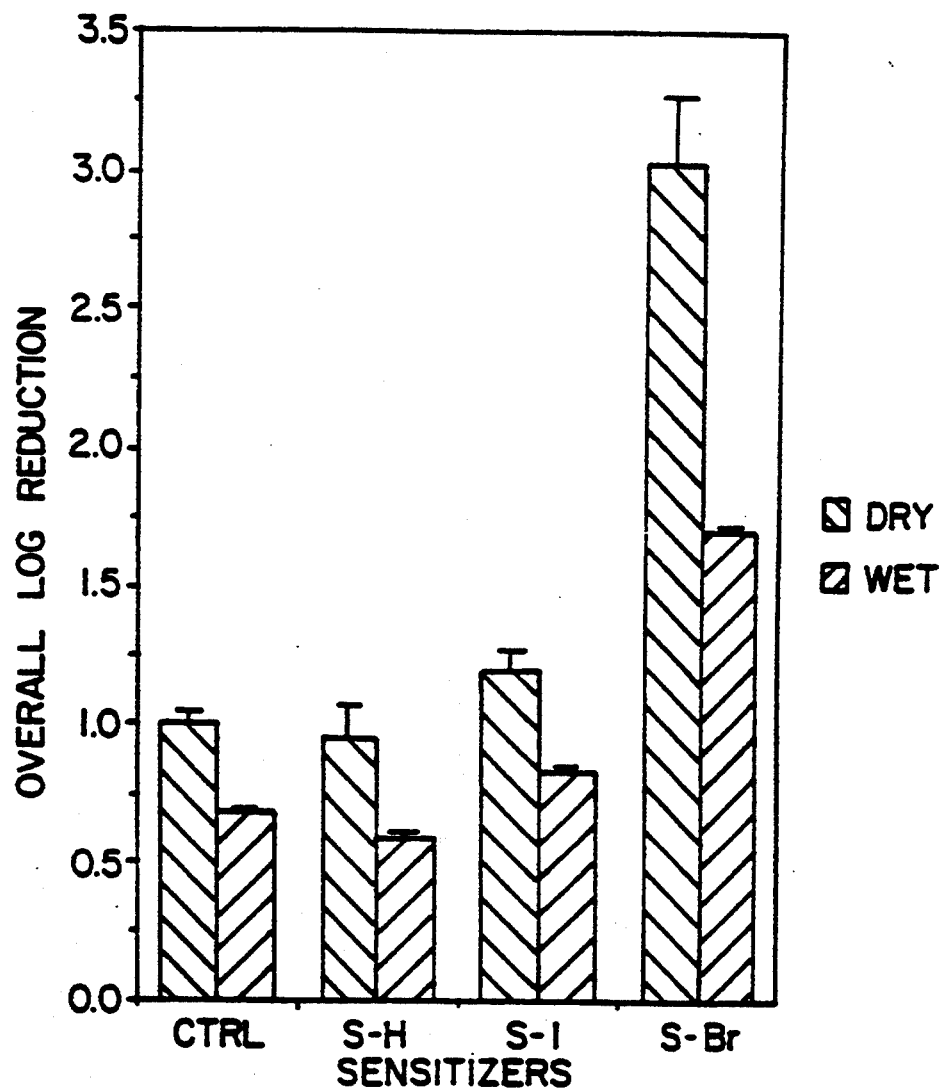
FIG. 3 is a plot of Phi 6 with inactivation according to the procedure of Example 5.

FIG. 2 shows the calculated mass attenuation coefficients (X-ray cross-section) of molybdenum and tungsten X-ray targets for cross-sections for iodine, bromine and platinum sensitizer compounds. The graph indicates that platinum and bromine sensitizer atoms absorb 100 to 175 times more radiation energy than carbon for low atomic number elements using a molybdenum target. However, the selectivity is reduced with a tungsten target. This suggests that the combination of platinum and bromine sensitizer atoms and a molybdenum target tube will allow activation of these sensitizers in the presence of a large excess of cellular and protein material. The viral inactivation obtained with molybdenum X-ray radiation and sensitizers with different heavy atoms are illustrated in FIG. 3.

EXAMPLE 5

VIRUS INACTIVATION IN DRY/WET PLASMA

Stock solution of $\phi 6$ phage was added to plasma to obtain the final virus concentrate of $1.2 \times 10^7$ PFU/ml. Compounds 19 and 20 (formulas given above) and fluorescein were added to the mixture to give the sensitizer concentration of 0.5 mg/ml. After addition of the sensitizer, the solution was mixed on a mechanical shaker for 1 hour at room temperature. The sample was transferred to a plastic Petri dish ($35 \times 10$ mm) and irradiated in a Pantak HP 160 X-ray unit equipped with a Mo target tube operating at 28 ma and 40 kv settings. Approximate radiation dose delivered was 353 kr. After irradiation the residual viral titre was measured by the plaque method. A phage containing irradiated sample was mixed with suitable phage host bacteria and 3 ml of melted soft agar. The mixture was poured over hard nutrient agar plate. After one day of incubation the lysed area stood out as plaque against the dense background. The plaques were counted with a colony counter. All samples were treated with X-ray radiation unless otherwise stated. For dry lyophilized state irradiation, the samples were prepared as described above and transferred to 50 ml round bottom flasks, lyophilized on a bench freeze dryer for 16 hours. The dry powder was placed in Petri dishes and X-ray irradiated to 353 kr. The residual viral titre was determined in reconstituted plasma by the plaque method as described above. The results are consistent with the hypothetical calculated selectivities shown in FIG. 2.

EXAMPLE 6

VIRAL INACTIVATION IN HYDRATED PLASMA

The initial titre of $\phi 6$ virus $1.2 \times 10^7$ PFU/ml in compound 20 (structure given above) and 0.5 mg/ml were used in hydrated plasma. The sample preparation and irradiation conditions were as described in FIG. 3. For R-17 virus the starting viral titre of $4.2 \times 10^8$ PFU/ml in compound No. 20 at 0.5 mg/ml were used. The results indicate that enhanced viral reduction is obtained with the use of sensitizers in combination with the X-ray radiation treatment.

EXAMPLE 7

VIRAL INACTIVATION WITH MOLYBDENUM X-RAY RADIATION IN LYOPHILIZED PLASMA WITH VARIOUS RESIDUAL MOISTURE CONTENTS

Figure 5:
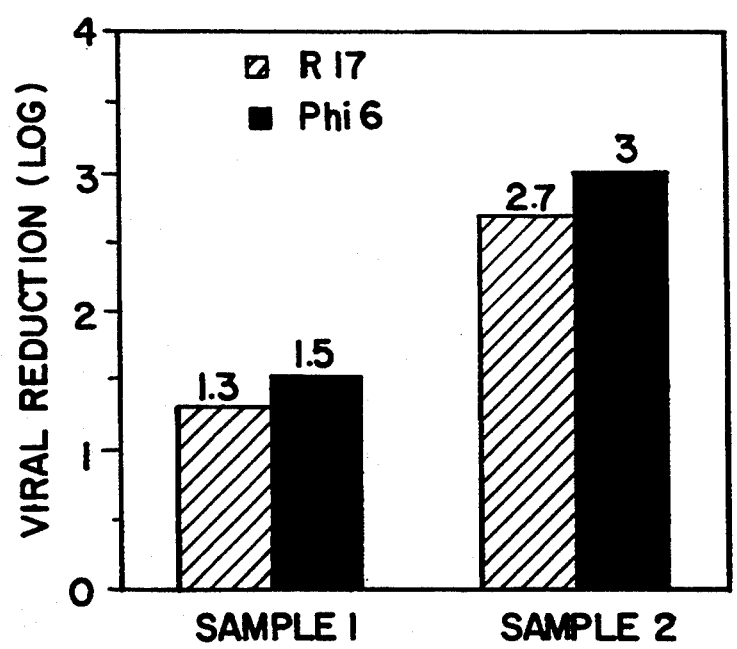
FIG. 5 is a plot of viral reduction in samples described in Example 7.

FIG. 5 shows the inactivation of enveloped and non-enveloped viruses obtained with molybdenum X-ray radiation treatment in lyophilized plasma preparations. The residual moisture content of Sample 1 was about 7.7% and of Sample 2 was about 2.4% as determined by a Karl/Fisher titrater. The starting concentrations of the viruses in the samples were $\phi 6$ ($2.0 \times 10^7$ PFU/ml and R-17, $4.4 \times 10^8$ PFU/ml). Sample 1 and Sample 2 were lyophilized in a Petri dish and round bottom flask respectively. All samples were treated with 353 kr dose and the final virus concentration was determined by the plaque method. The results indicate that the amount of the residual moisture in lyophilized samples significantly influences the degree of inactivation obtained with X-ray radiation treatment in the presence of and absence of a sensitizer.

EXAMPLE 8

VIRAL INACTIVATION IN LYOPHILIZED PLASMA IN THE PRESENCE AND ABSENCE OF A SENSITIZER WITH MOLYBDENUM X-RAY RADIATION

Figure 6:
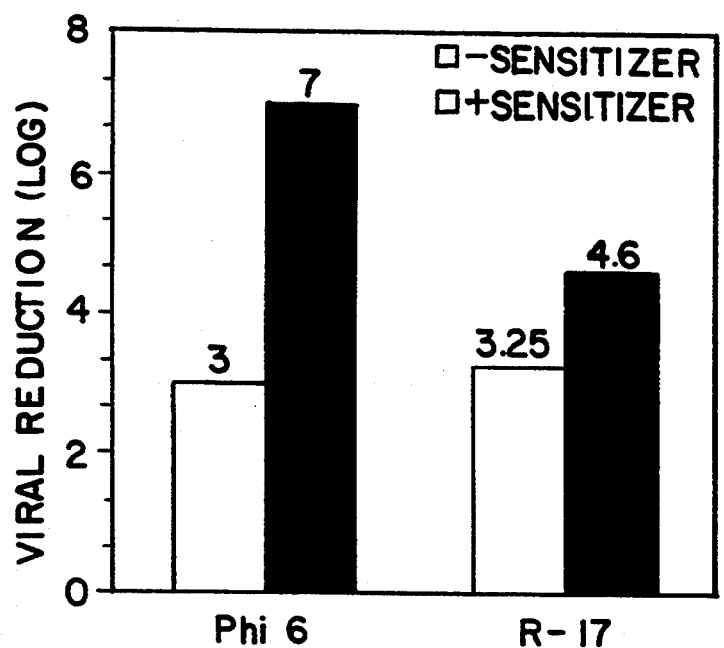
FIG. 6 is a plot of viral reduction in samples described in Example 8.
Figure 7:
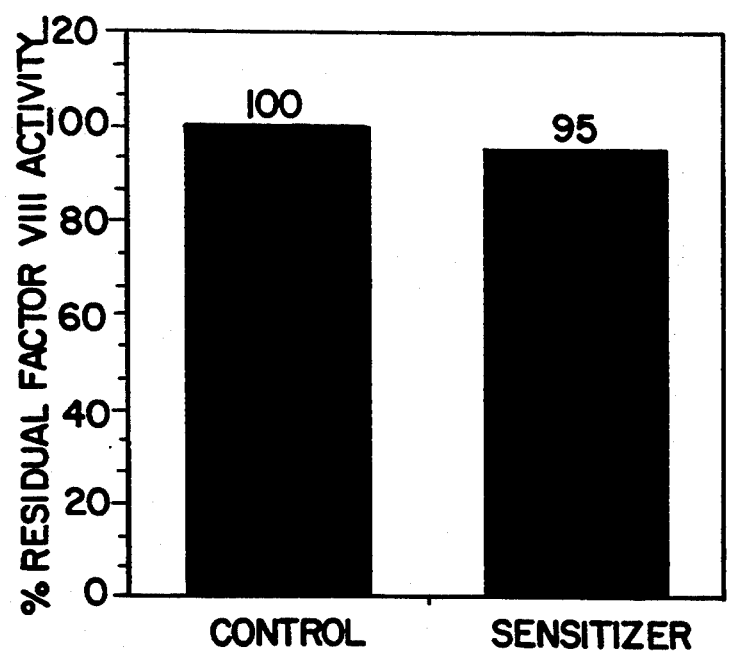
FIG. 7 is a plot of residual Factor VII in X-ray irradiated lyophilized plasma.

Samples have starting $\phi 6$ virus titre of $8.1 \times 10^8$ PFU/ml and compound No. 20 (structure given above) at 0.5 mg/ml were used in lyophilized plasma. The radiation dose employed was 420 kr. For the R-17 virus the conditions were: initial titre $3.7 \times 10^8$ PFU/ml and compound No. 7 (structure given above) at 0.2 mg/ml, 353 kr radiation dose. Samples not irradiated with X-ray radiation showed very small or no change in starting viral titre value. The results are shown in FIG. 6 where there is shown a 7 log reduction in viral titre of $\phi 6$ and a 4.6 log reduction in viral titre of R-17 using a sensitizer. FIG. 7 shows the residual factor H activity X-ray irradiated lyophilized plasma (AHF concentrate) from the same samples. The damage factor to Factor VIII activity in lyophilized plasma during viral inactivation treatment is negligible. Greater than 95% recovery of Factor VIII recovery is shown using the sensitizer.

EXAMPLE 9

VIRAL INACTIVATION IN HYDRATED PLASMA USING UV IRRADIATION TREATMENT

Figure 8:
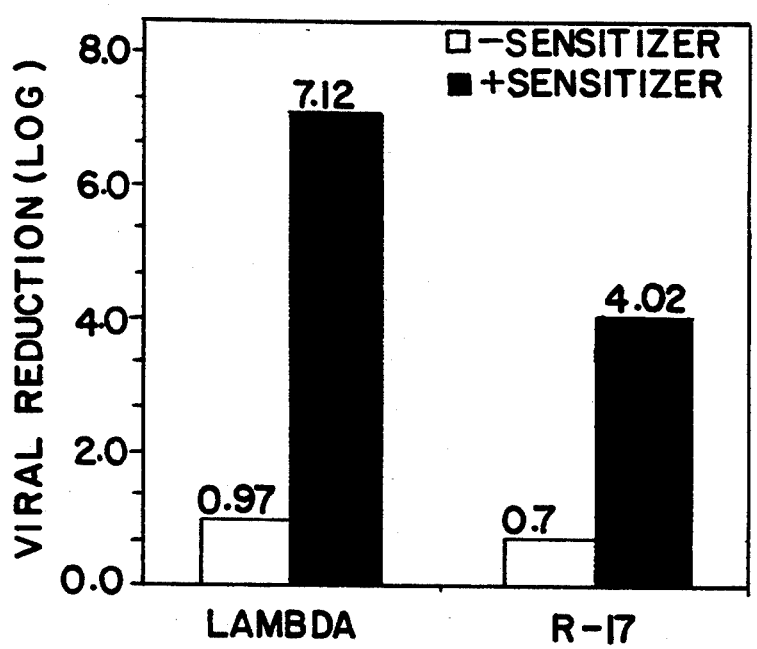
FIG. 8 is a plot of viral reduction of samples described in Example 9.
Figure 9:
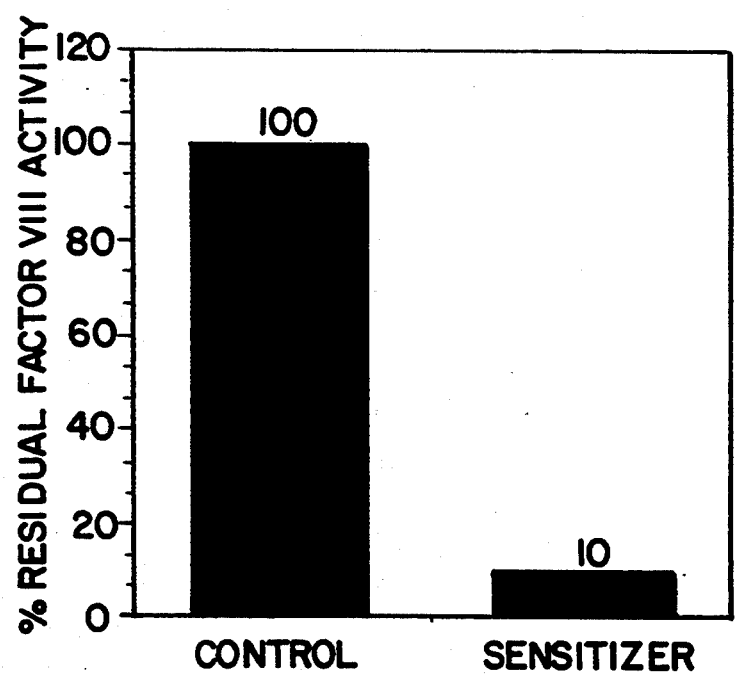
FIG. 9 is a plot of residual Factor VIII activity in UV irradiated plasma.

A stock solution of bacterial phage $\lambda$ is added to plasma to obtain final titre of $1.2 \times 10^8$ PFU/ml and compound No. 3 (structure given above) at 0.1 mg/ml concentration. The mixture was transferred to Pyrex glass photolysis cells and exposed to UV (300-360 nm blue lamp) for 5 minutes. After UV irradiation treatment the final viral titre and Factor VIII activity were measured as described earlier. FIG. 8 shows viral reductions obtained. About 3-6 logs of increased viral inactivation was obtained with protein coated viruses using a sensitizer. The recovery of Factor VIII in these samples after inactivation treatments is shown in FIG. 9. Only 10% of Factor VIII activity was recovered after viral inactivation treatment. However, addition of antioxidants, such as vitamin E, increase Factor VIII recovery under UV irradiation.

EXAMPLE 10

VIRAL INACTIVATION IN HYDRATED AND LYOPHILIZED PLASMA IN PRESENCE AND ABSENCE OF ORGANIC SOLVENTS

Figure 10:
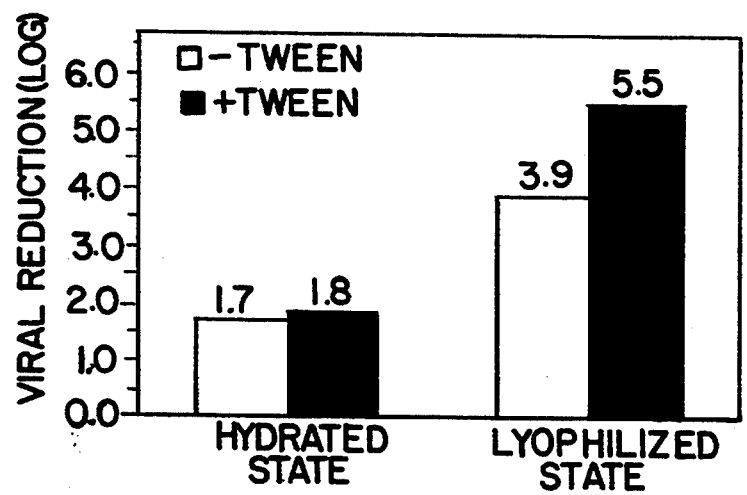
FIGS. 10, 11 and 12 are plots of viral reduction in samples described in Example 10.
Figure 11:
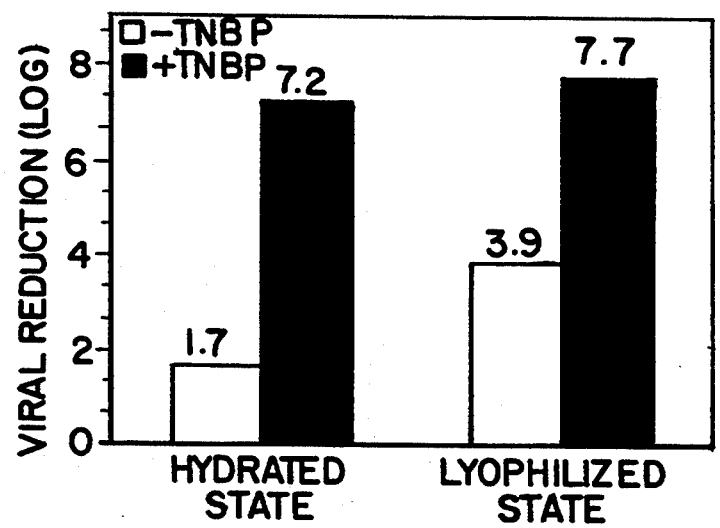
Figure 12:
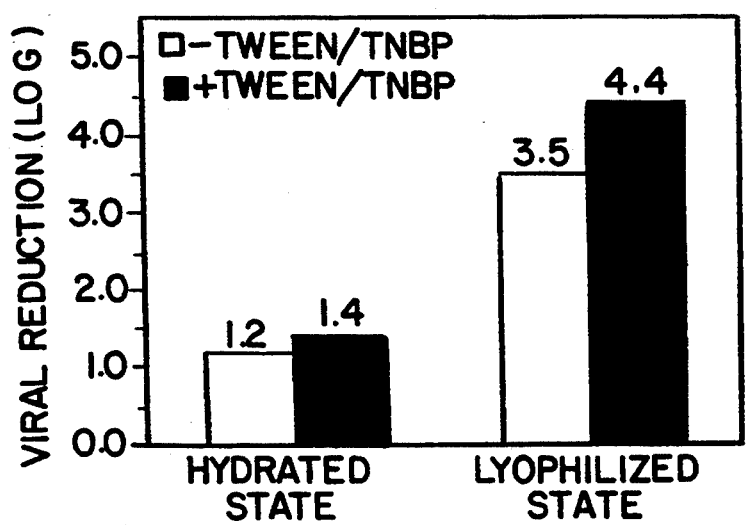

The starting titre of $\phi 6$ virus was $2.5 \times 10^8$ PFU/ml in these samples. The plasma mixture was mixed with either 1% Tween 80 detergent or 1% tri-(n-butyl)phosphate (TNBP) for 2 hours at room temperature. The samples were treated with 353 kr radiation dose in hydrated and lyophilized states as described above. The results are shown in FIGS. 10 and 11. The data indicates that the viral inactivation obtained with molybdenum X-ray radiation in hydrated and lyophilized plasma is substantially enhanced by addition of either organic solvent (TNBP) or detergent (Tween 80) individually or in combination. FIG. 12 shows the results using a stock solution of R-17 virus added to plasma to give a starting titre of $6.2 \times 10^8$ PFU/ml and 1% Tween 80 with 1% TNBP for two hours at room temperature. The hydrated and lyophilized samples were treated with 353 kr radiation dose and the final viral titre was determined as described above.

EXAMPLE 11

VIRAL INACTIVATION IN PLATELETS (FROZEN/LIQUID)

Figure 13:
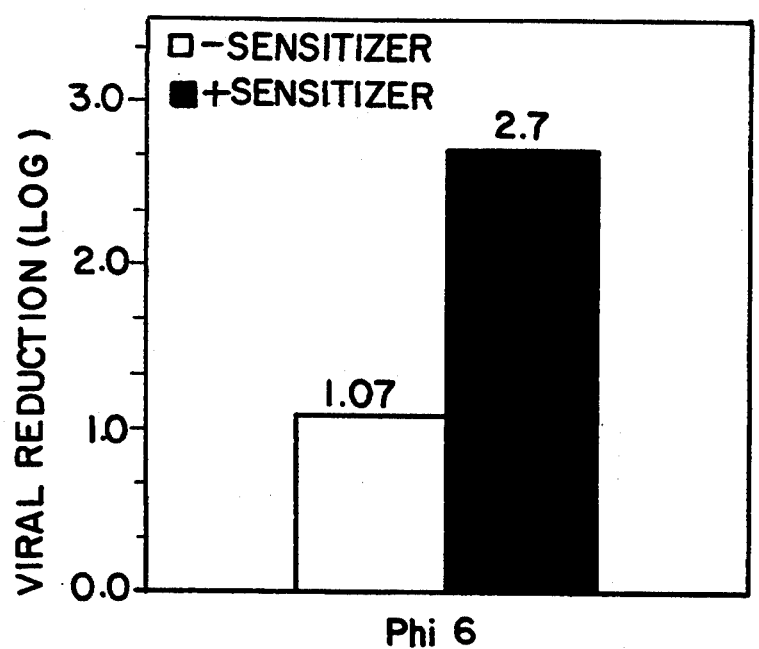
FIGS. 13, 14, 15 and 16 are plots of viral reduction in samples described in Example 11.
Figure 14:
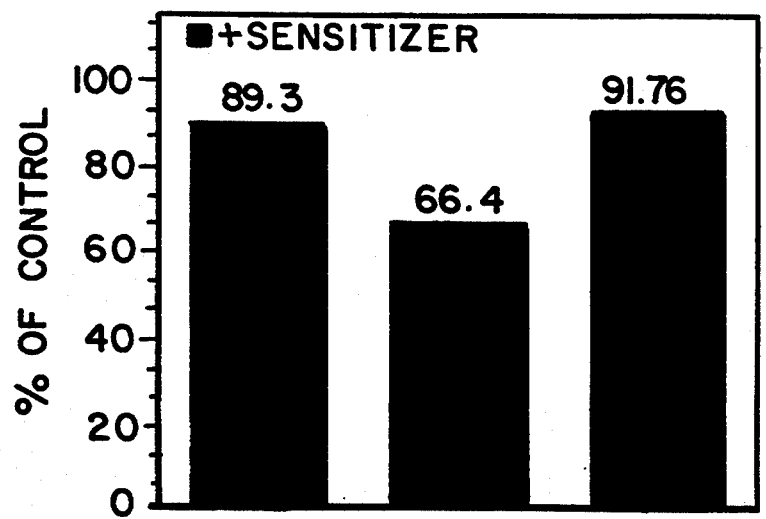

Fresh platelets (24 hours old) were spun to remove residual red cells. The platelets were diluted with plasma to obtain approximately $500 \times 10^6$ cells ml. The starting titre of $\phi 6$ virus in liquid platelet preparation was $2.0 \times 10^5$ PFU/ml. After addition of compound 20, 0.3 mg/ml of the sample was transferred to a polyolifin bag (2 inches by 2 inches dimensions) and irradiated to deliver approximately a radiation dose of 195.4 kr. Subsequently the sample was analyzed for morphological evaluation under microscope, cell recovery calculations were made, and aggregation response to collagen (200 μg/ml) was determined by an aggregometer. The final virus titre was determined by the plaque method. The liquid state results were shown in FIGS. 13 and 14. For the frozen samples, fresh platelets $500 \times 10^6$ cells/ml were diluted with 10% DMSO in PBS buffer (1:1, v/v).

Figure 15:
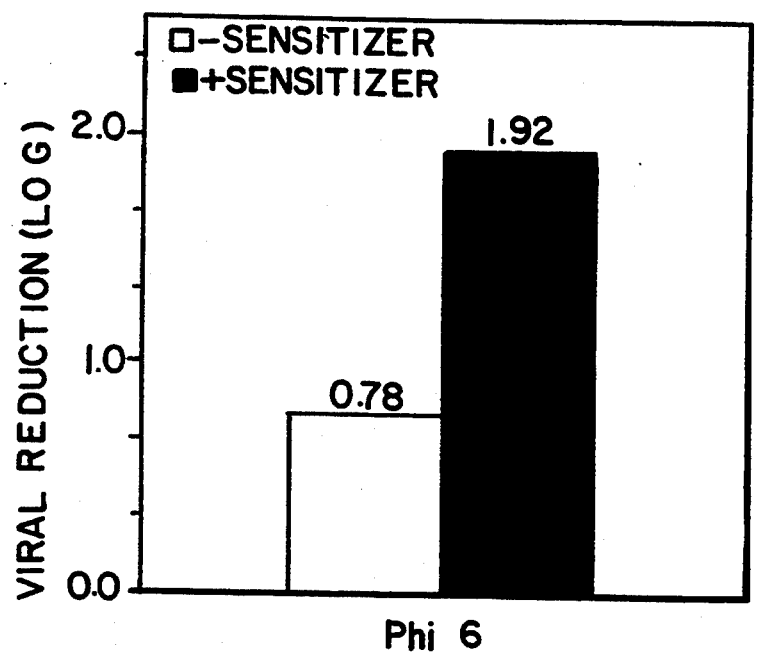
Figure 16:
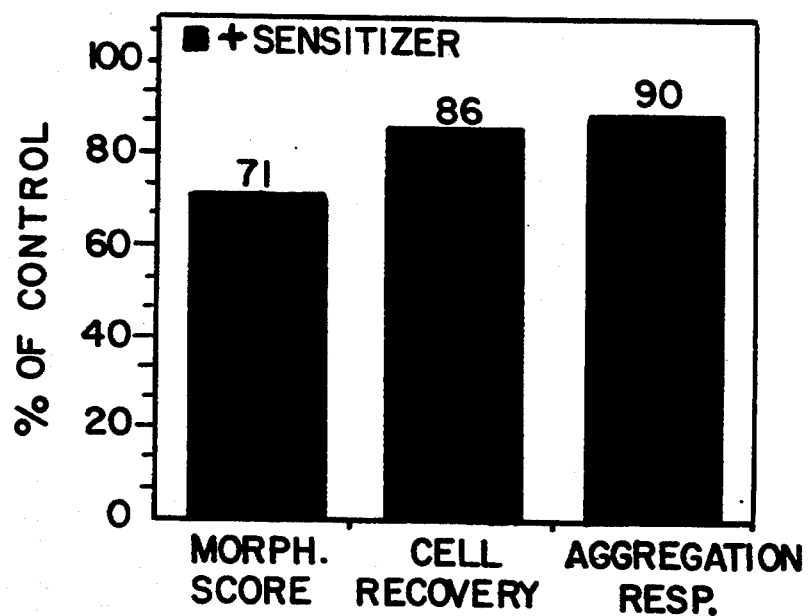
Figure 17:
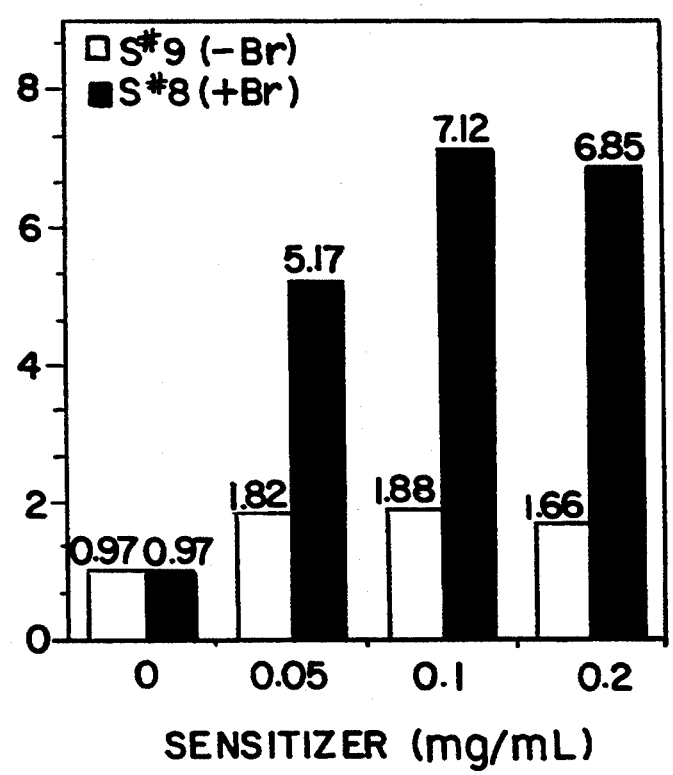
FIG. 17 is a plot of lambda virus reduction with psoralen sensitizer (with and without bromine) in hydrated plasma in sensitizer concentrations of 0.05, 0.1 and 0.2 mg/ml. The sensitizers are psoralen (S#9) and Br-psoralen (S#8), activated with UV.
Figure 18:
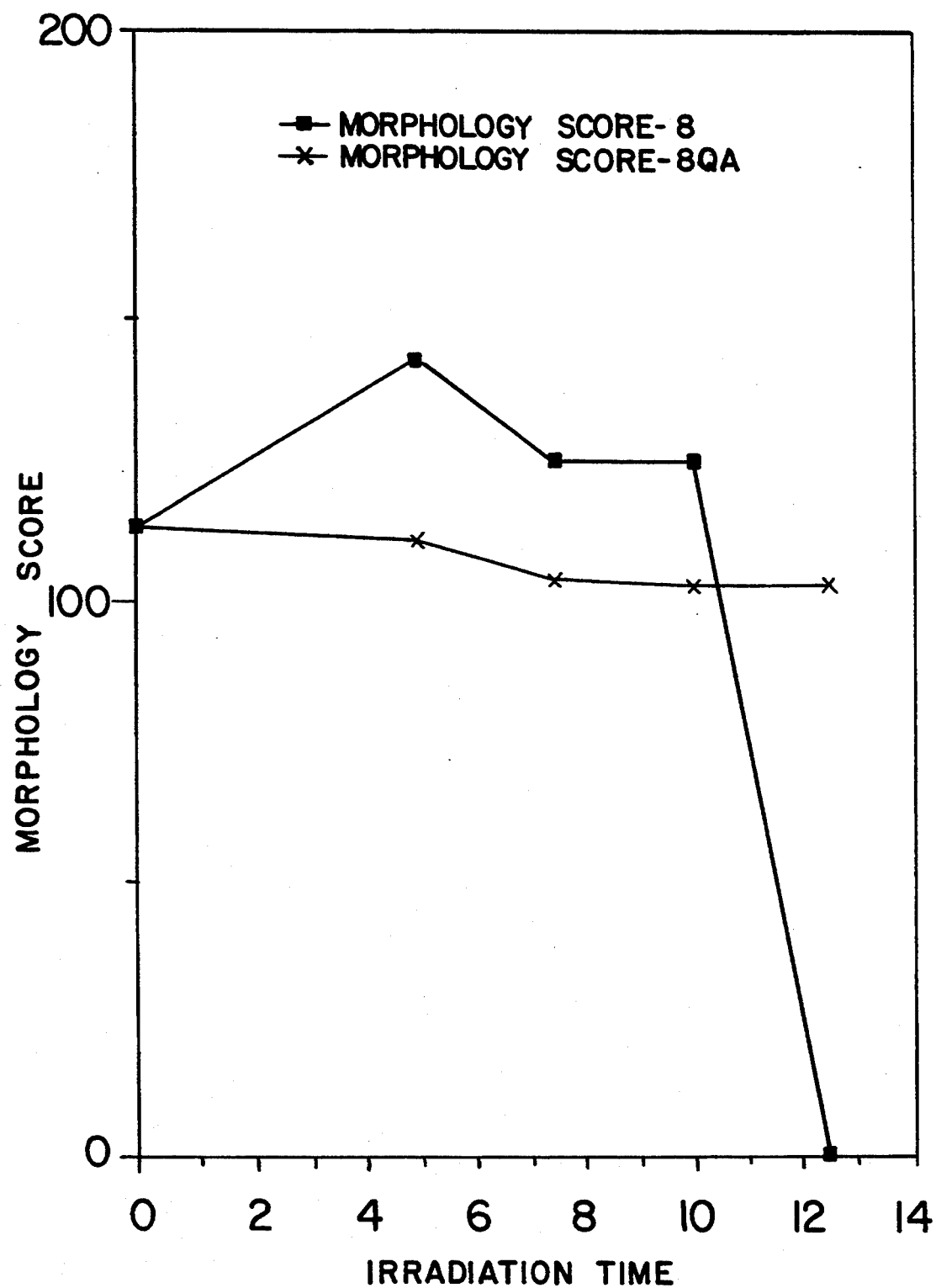
Figure 19:
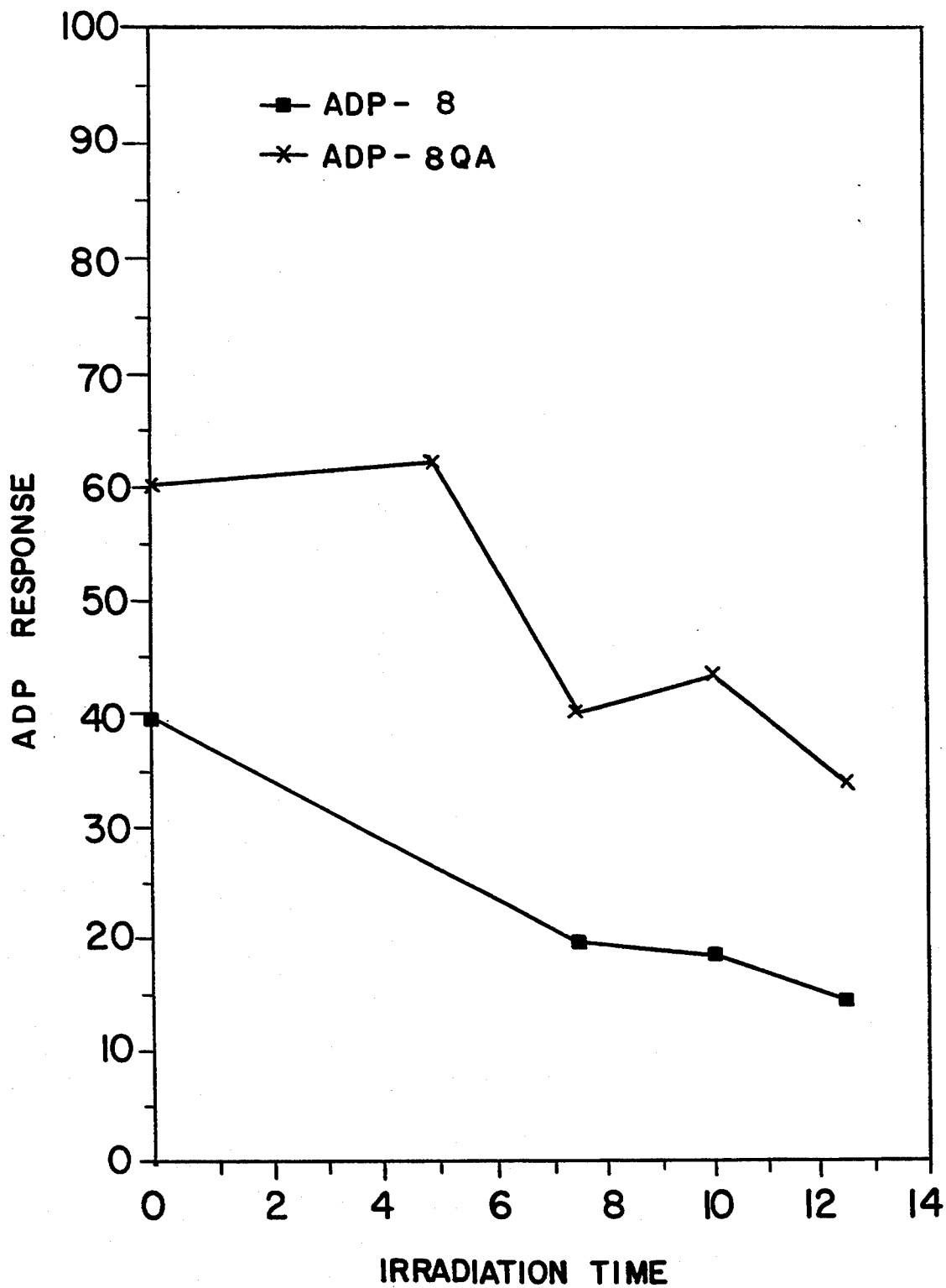
Figure 20:
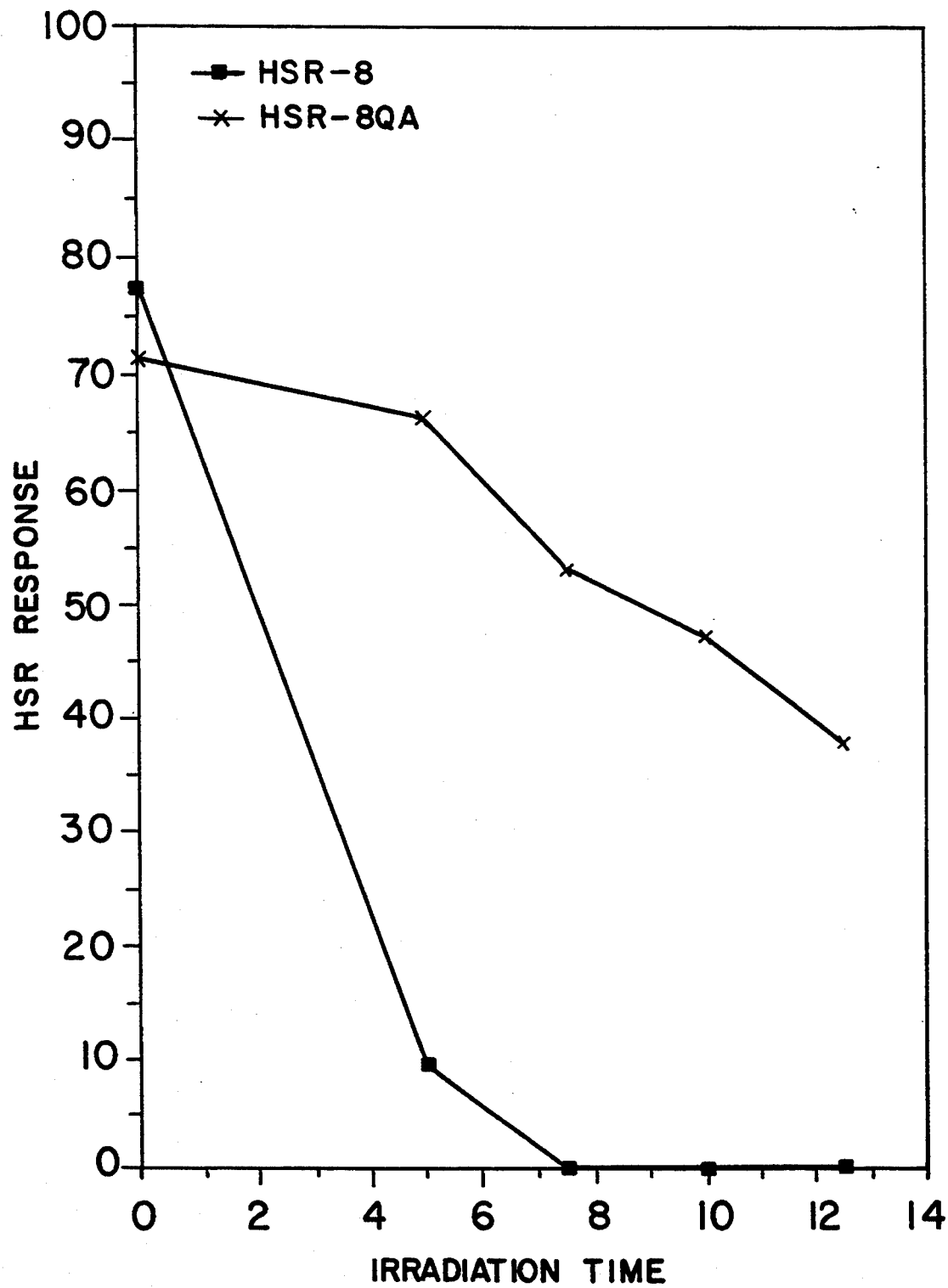
Figure 21:
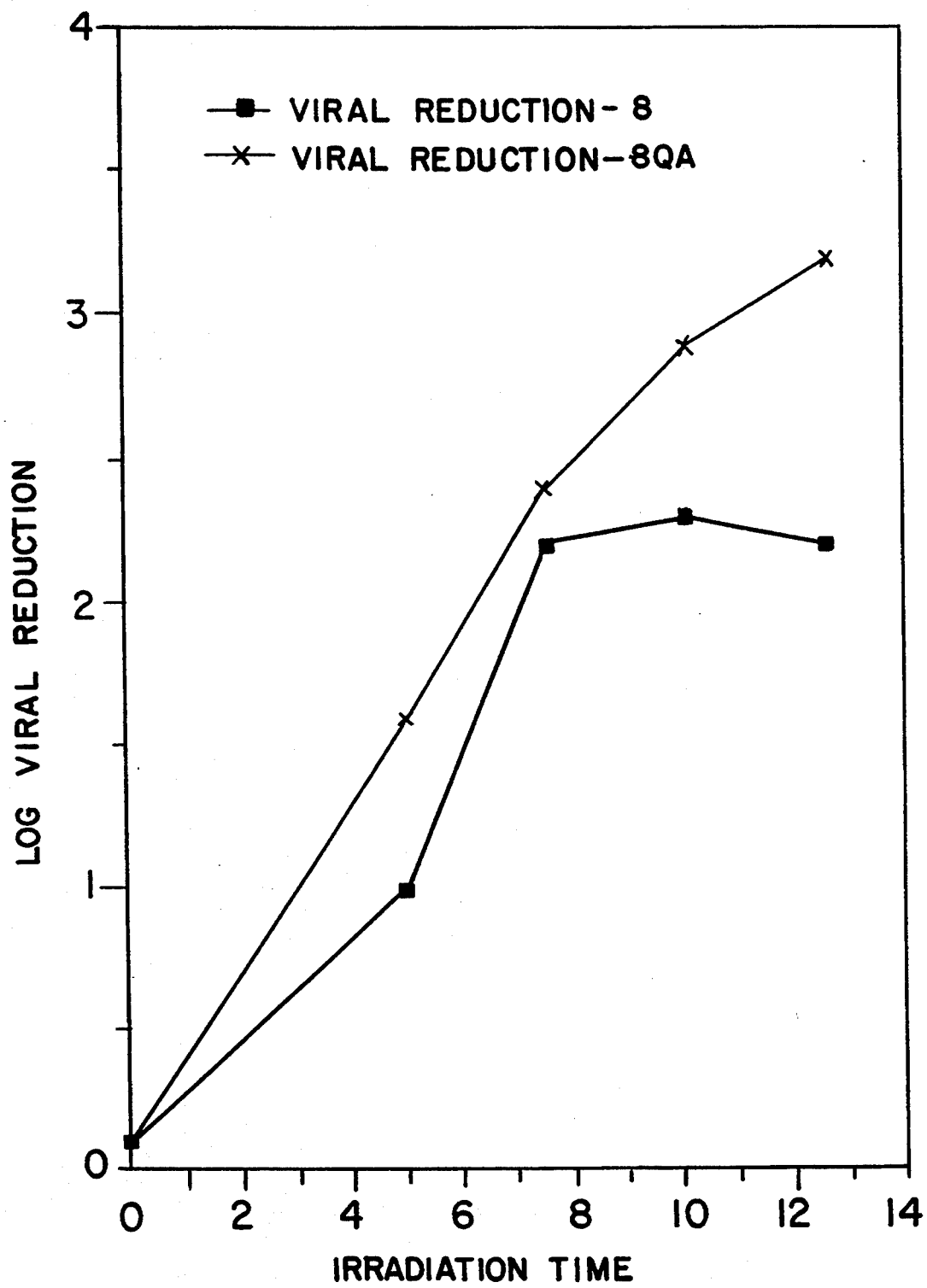
Figure 22:
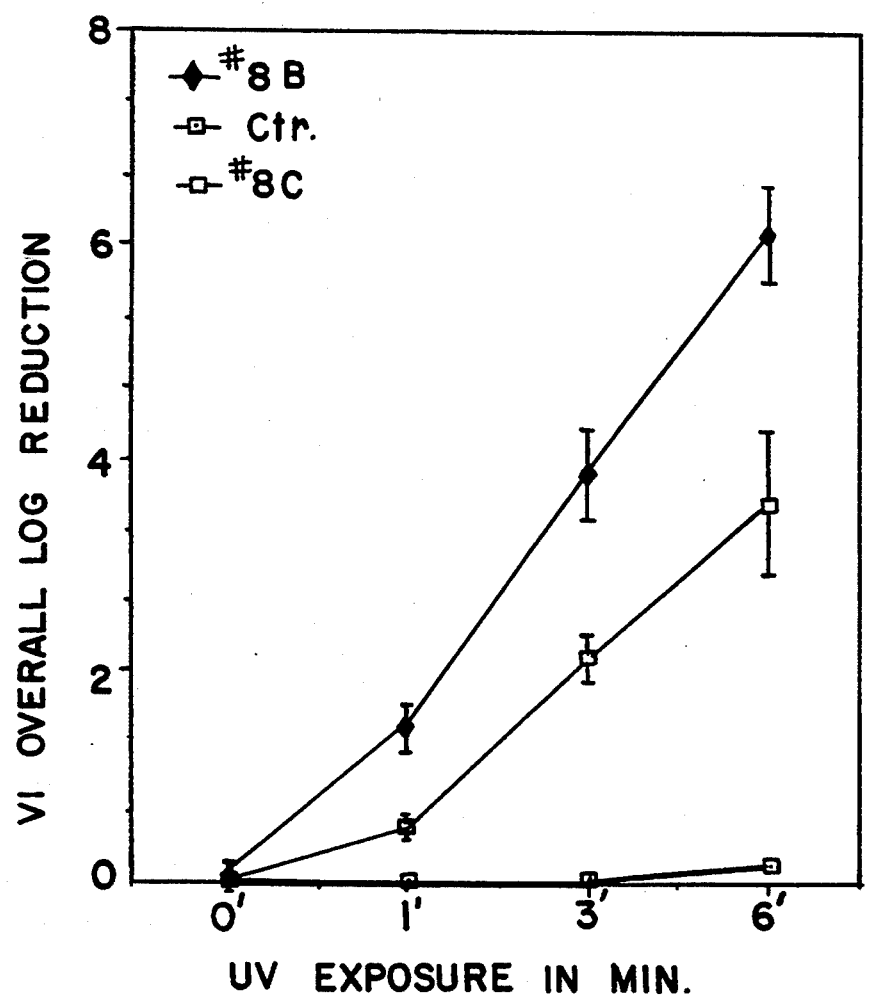
Figure 23:
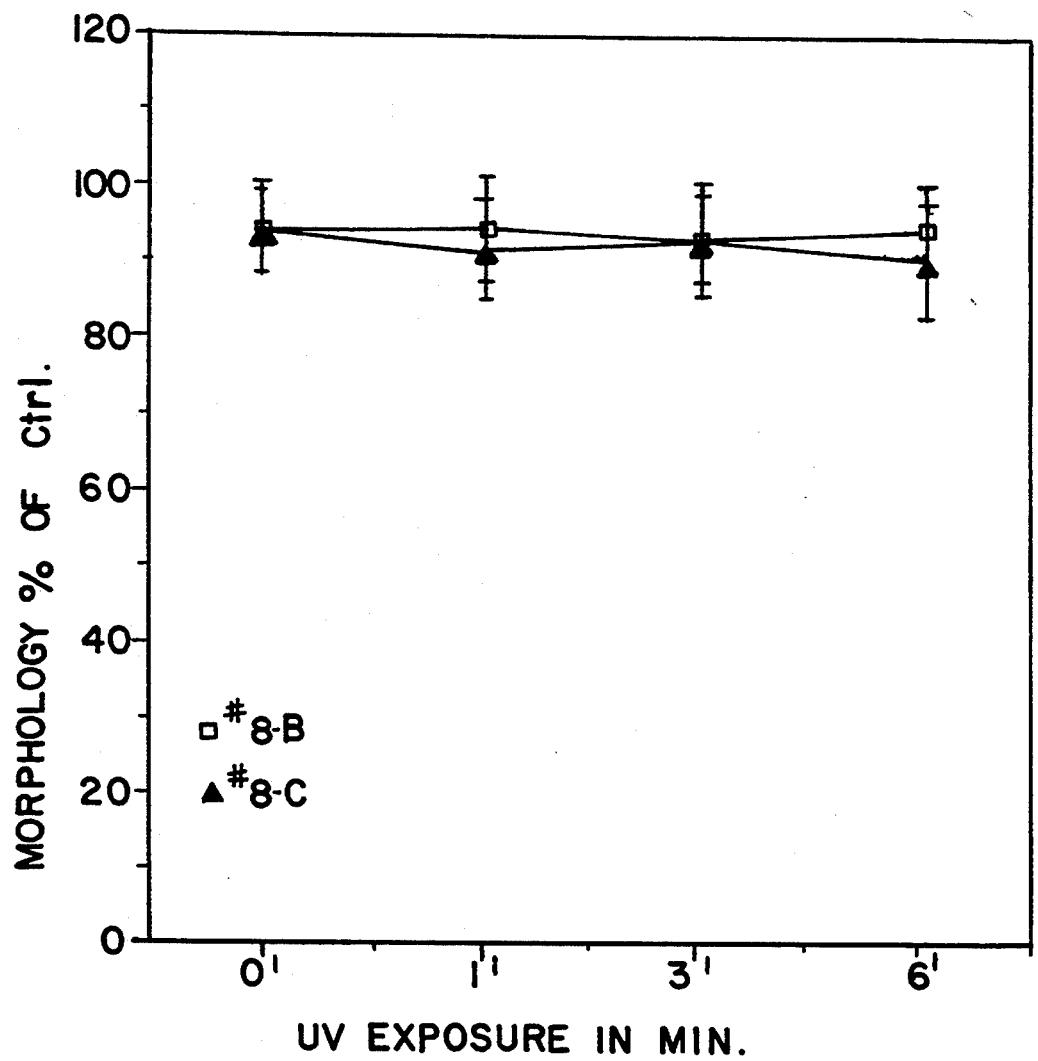
Figure 24:
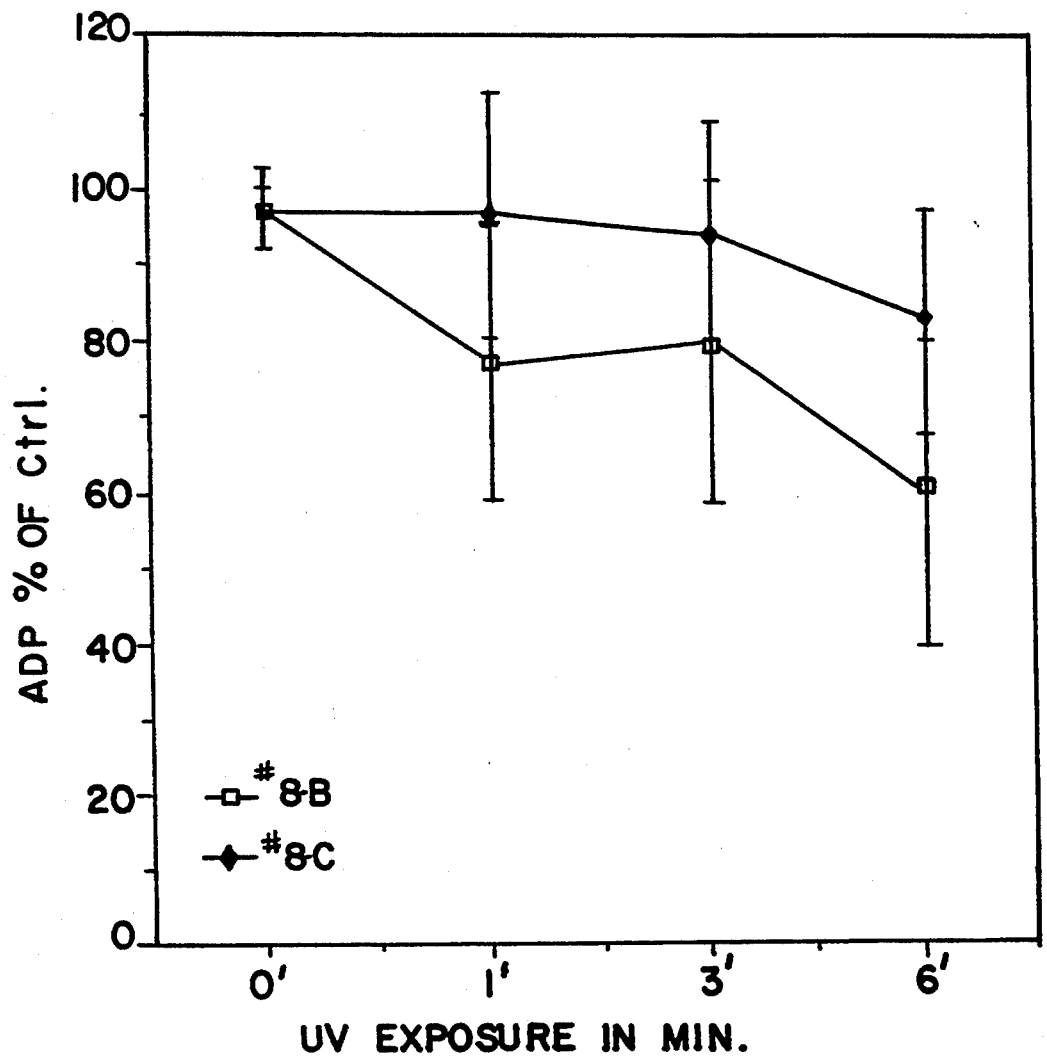
Figure 25:
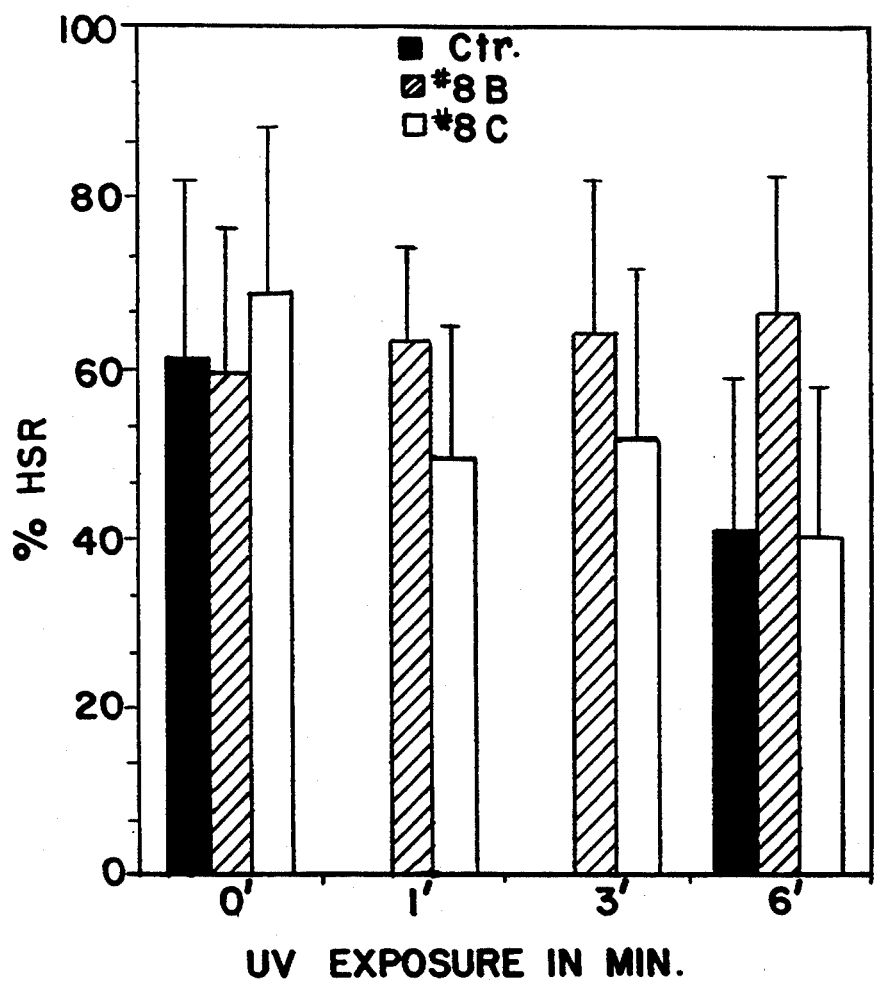

The starting $\phi 6$ virus titre was $2.0 \times 10^6$ PFU/ml. The compound No. 20 was added at a concentration of 0.3 mg/ml and the sample (2 ml) was transferred to a polyolifin bag and frozen. The frozen bag was treated with 26.3 kr radiation dose. The sample bag temperature was maintained at $-80°$ C. using liquid nitrogen during the irradiation treatment. After irradiation the sample was thawed at 37° C. and diluted with PBS slowly to 10 ml. The washed platelets were resuspended in plasma and analyzed for morphological evaluation, cell recovery and aggregation response to collagen (200 mg/ml). The final virus titre after irradiation was determined by thawed samples by the plaque method. Results were shown in FIGS. 15 and 16. These results suggest that the addition of sensitizer increases the viral inactivation by 1 to 2 logs. The irradiation damage to platelets is not significant (70% to 90% control of viability assays) as determined by the morphological score, cell recovery and aggregation response to collagen agonist.

EXAMPLE 12

Human platelet concentrates are mixed with phi 6 bacteriophage, with or without sensitizer, then exposed to U.V. light. Cell quality assays after treatment include morphology score conducted by visual inspection using a light microscope (using a Kunicki scoring system), hypotonic shock response (HSR), aggregation response induced by addition of ADP measured in an aggregometer, and cell number count.

PROCEDURE FOR IRRADIATION OF PLATELETS

1. Soft spin platelet unit at 1000 rpm for 5 min to remove RBC.
2. Dilute concentrated platelets with spun autologous plasma to obtain a conc. of $500 \times 10^6$ cells/ml.
3. Add $5 \times 10^6$ of $\phi 6$ to the platelet suspension and mix gently.
4. Add sensitizer to the platelet suspension and incubate for 15 min while protecting from light. Control samples have PBS added.
5. Pipet 2 ml aliquots into small plastic petri dishes and irradiate with UV while rotating samples at 100 rpm on a shaker. Irradiate samples without cover.
6. Transfer irradiated samples to 15 ml plastic centrifuge tubes.
7. Determine morphology, HSR, ADP, Viral inactivation, cell count.

PLT#137,139,140/S#8, 8-QA (UV):
  Sensitizer conc.: 0.050 mg/ml or 50 mg/ml
  Sensitizer stock: 2.00 mg/ml in PBS
  Irradiation times: 5', 7.5', 10', 12.5'
  Controls: 0', 12.5' no Sensitizer 0' Sensitizer 8, 8-QA.

| TABLE OF TESTED COMPOUNDS OF FORMULA (A) ($R_6$ = H in all cases) | | | | | |
|---|---|---|---|---|---|
| No. | $R_1$ | $R_2$ | $R_3$ | $R_4$ | $R_5$ |
| AMT | —Me | —CH$_2$NH$_3^{\oplus}$ | —H | —Me | —Me |
| 8 | —H | —H | —Br | —O(CH$_2$)$_3$N$^{\oplus}$H(Et)$_2$ | —H |
| 8QA | —H | —H | —Br | —O(CH$_2$)$_3$N$^{\oplus}$Me$_3$ | —H |
| 8A | —H | —H | —H | —O(CH$_2$)$_3$N$^{\oplus}$Me$_3$ | —H |
| 8B | —H | —H | —Br | —O(CH$_2$)$_3$N$^{\oplus}$Et$_3$ | —H |
| 8C | —H | —H | —H | —O(CH$_2$)$_3$N$^{\oplus}$Et$_3$ | —H |
| 8D | —H | —H | —Br | —O(CH$_2$)$_6$N$^{\oplus}$Me$_3$ | —H |

| COMPARISON OF PSORALEN SENSITIZER WITH DIFFERENT SIDE CHAINS Note: Concentration of all sensitizers is 50 µg/ml | | | |
|---|---|---|---|
| | n = 3 Sensitizer #8 | n = 3 Sensitizer #8QA | n = 3 Untreated Platelets (1 day old) |
| Morphology | | | |
| 0 min. | 113 ± 9 | 113 ± 6 | 124 ± 8.7 |
| 5 min. | *143 ± 4 | 111 ± 9 | |
| 7.5 min. | *125 ± 17 | 104 ± 3 | |
| 10 min. | *125 ± 7 | 103 ± 3 | |
| 12.5 min. | **0 ± 0 | 103 ± 8 | |
| ADP Response | | | |
| 0 min. | 39.7 ± 17.2 | 60.2 ± 5.8 | 62 ± 6.6 |
| 5 min. | Not Done | 62.5 ± 2.6 | |
| 7.5 min. | 19.5 ± 4.4 | 40.1 ± 10.5 | |
| 10 min. | 18.6 ± 1.5 | 43.5 ± 20.3 | |
| 12.5 min. | 14.2 ± 4.6 | 33.9 ± 13.9 | |
| HSR Response | | | |
| 0 min. | 77.3 ± 10.9 | 71.3 ± 13.9 | 64 ± 9.9 |
| 5 min. | 9.3 ± 13.2 | 66.3 ± 8.2 | |
| 7.5 min. | 0 ± 0 | 53.3 ± 6.6 | |
| 10 min. | 0 ± 0 | 47.3 ± 1.9 | |
| 12.5 min. | 0 ± 0 | 37.9 ± 8.4 | |
| Viral Reduction | | | |
| 0 min. | 0.06 ± 0.06 | 0.09 ± 0.08 | N/A |
| 5 min. | 1.0 ± 0.7 | 1.6 ± 0.6 | |
| 7.5 min. | 2.2 ± 0.7 | 2.4 ± 0.6 | |
| 10 min. | 2.3 ± 0.5 | 2.9 ± 0.7 | |
| 12.5 min. | 2.2 ± 0.6 | 3.2 ± 0.7 | |

*Although morphology score values are high, the cells appeared to be swollen under the microscope into a spherical form. This cell form is consistent with cells that have been found to be "fixed" and inactive in responses. This is also consistent with values observed in other assays.
**These samples were completely aggregated after treatment.

FIGS. 18–25 are graphs of the experimental data on platelet quality as a function of U.V irradiation time.

EXAMPLE 13

THE COMPARISON OF VIRAL INACTIVATION EFFICIENCIES OF BROMINATED AND NON-BROMINATED SENSITIZERS

To test the viral inactivation efficiency of brominated sensitizers, platelet preparations (2 mL, PRP) were spiked with φ6 phage and brominated psoralen (8B) and non-brominated psoralen(8C) were added to obtain final sensitizer concentration of 0.1 mg/mL. The samples were exposed to UVA light in a home made reactor consisting of 4 UvA lamps for the indicated time periods. The petri dishes containing samples were mixed on an orbital shaker during UVA exposure. The UVA light intensity at the sample position was measured at 3.3 mW/cm$^2$. The residual viral titer after each time point was measured by plaque method The vital reduction values are illustrated in FIG. 26. These results clearly indicate the enhancement in the level of vital inactivation observed with brominated compound when compared with non-brominated derivative under identical conditions. These results demonstrate that as much as a 400 fold improvement in the level of viral inactivation observed when the psoralen molecule is brominated.

EXAMPLE 14

THE INFLUENCE OF SENSITIZER SIDE CHAIN ON PLATELET IN VITRO PROPERTIES

The viral inactivation values and in vitro properties of platelets subjected to viral inactivation treatment using various derivatives of psoralen are summarized in Table 1. The psoralen derivative with acidic hydrogens (AMT) produced substantial reduction in hypotonic shock response (HSR) and ADP aggregation response relative to the control sample. These results indicate that the presence of acidic hydrogens on the side chain nitrogen is detrimental to blood cells because of the hydrogen bonding with cell membrane phospholipid head groups, whereas quaternary ammonium derivatives produced significantly lower damage to platelets due to a charge screening effect.

EXAMPLE 15

VIRAL INACTIVATION IN SINGLE UNIT PLATELET CONCENTRATES

Single unit platelet concentrates were obtained 24 hours after collection from certified blood banks. The platelet were subjected to soft spin to remove residual RBC and about 6 logs of φ6 phage and sensitizer 8B were added in PBS solution to obtain 0.03 mg/mL final sensitizer concentration. The samples were transferred to Stericonpolyolefin bag (which transmits 60% of UVA light) and irradiated from top (3.6 mW/cm$^2$)and bottom (3.4 mW/cm$^2$) in a home made reactor for 10 min. The bags were continuously mixed on extended glass platform attached to orbital shaker. The viral inactivation values and in vitro properties of platelet concentrates were monitored for 2 days after the treatment. The results are summarized in Table 2. The data indicates that >5.3 logs of viral reduction was obtained with excellent retention of platelet in vitro properties.

EXAMPLE 16

VIRAL INACTIVATION RED BLOOD CELLS

Units of packed red cells were transferred to Stericon red cell freezing bags and the hematocrits were adjusted to 60% with PBS. The samples were spiked with 5×10$^6$ PFUlmL φ6 phage and 0.3 mg/mL sensitizer 8B. The contents of the bag was exposed to UVA light from top (3.6 mW/cm$^2$) and bottom (3.4 mW/cm$^2$) for 6 hours (151.2 J/cm$^2$). The samples were mixed continuously during UVA exposure on an orbital shaker. The final viral titer in the sample was determined by the plaque method. In vitro biochemical and biophysical properties of treated red cells were monitored for 7 day following the treatment. The results are summarized in Table 3. The data indicates that >6.6 logs (complete inactivation of added virus) of viral reduction was obtained without any significant alterations in in vitro biochemical and biophysical properties.

EXAMPLE 17

EFFECT OF UVA LIGHT INTENSITY ON VIRAL INACTIVATION IN RED CELLS

The viral inactivation kinetics in red cells is dependent on the intensity of the UVA light source. The data in Table 4 indicate that the time required to achieve 6 logs of viral reduction varies with the intensity of the UVA light source used. The time required to achieve 6 logs viral reduction in red cells is substantially reduced to 90 min. using a very high intensity UVA light source (40 mW/cm$^2$ (top) and 40 mW/cm$^2$ from bottom).

EXAMPLE 18

INACTIVATION OF VIRUSES IN HUMAN PLASMA AND BOVINE SERUM WITH UV ACTIVATION

Vital inactivation in FBS was carried out in 100 mL serum samples in 225 cm² tissue culture flask in the presence of sensitizer 8B (0.03 mg/mL). The sample was exposed to UVA light from top (3.6 mW/cm²) and bottom (3.4 mW/cm²) while continuously mixing on an orbital shaker for 30 min. (8.4 J/cm²). Human plasma was irradiated in a Pyrex glass photolysis cell in the presence of sensitizer 8 (0.1 mg/mL) for 5 min. Inactivation of various bacteriophages were carried out using brominated psoralens in combination with UVA light. The results in Table 5 clearly indicate that 5-7 logs of viral reduction was obtained with various phage (enveloped and non-enveloped) in human plasma fractions and fetal bovine serum products.

EXAMPLE 19

INACTIVATION OF BACTERIA (E. COLI) IN FETAL BOVINE SERUM (FBS)

FBS (5 mL) sample was spiked with E. coli bacteria and sensitizer 8 (0.03 mg/mL) and irradiated for 15 min. (3.3 mW/cm²). The residual bacterial titer was determined by colony forming assay using agar plates. The results (FIG. 27) indicate that brominated psoralens effectively inactivate bacteria as well as viral contaminants.

EXAMPLE 20

DETERMINATION OF AMES MUTAGENICITY (IN VITRO) OF BROMINATED PSORALENS

The standard Ames mutagensity test using salmonella mutants was performed on brominated sensitizer 8B at 0.6 mg(mL. The results are summarized in Table 6. The data indicates that the compound at 0.6 mg/mL concentration is non-mutagenic.

EXAMPLE 21

SELECTION OF X-RAY TARGET SOURCE

The X-ray cross-section ratios of bromine to carbon, iodine to carbon and platinum to carbon were calculated for their cross-sections in for various X-ray target tubes (ref.: W. H. McMaster, et al., UCRL-50174 section 11, Section III, Section W, and CRC Handbook of Chemistry and Physics, pp. E147, 1979. The calculated values (FIG. 28) suggest that Mo, Rh, Pd and Ag X-ray target tubes will produce suitable wave length radiation and selectivity in X-ray cross-sections for sensitizer atoms over carbon.

EXAMPLE 22

VIRUS INACTIVATION IN DRY/WET PLASMA

Stock solution of $\phi 6$ phage was added to plasma to obtain the final virus concentration of $1.2 \times 10^6$ PFU/mL. Compounds RB (rose bengal), EY (eosin Y) FL (fluoroscein) were added to the mixture to give the sensitizer concentration of 0.5 mg/mL. After addition of the sensitizer, the solution was mixed on a mechanical shaker for 1 hour at room temperature. The sample was transferred to a plastic petri dish (35×10 mm) and irradiated in a Pantak HP 160 X-ray unit equipped with a Mo target tube operating at 28 MA and 40 KV settings. Approximate radiation dose delivered was 353 Kr. Mter irradiation the residual viral titer was measured (FIG. 29) by the standard double agar plaque method.

Figure 4:
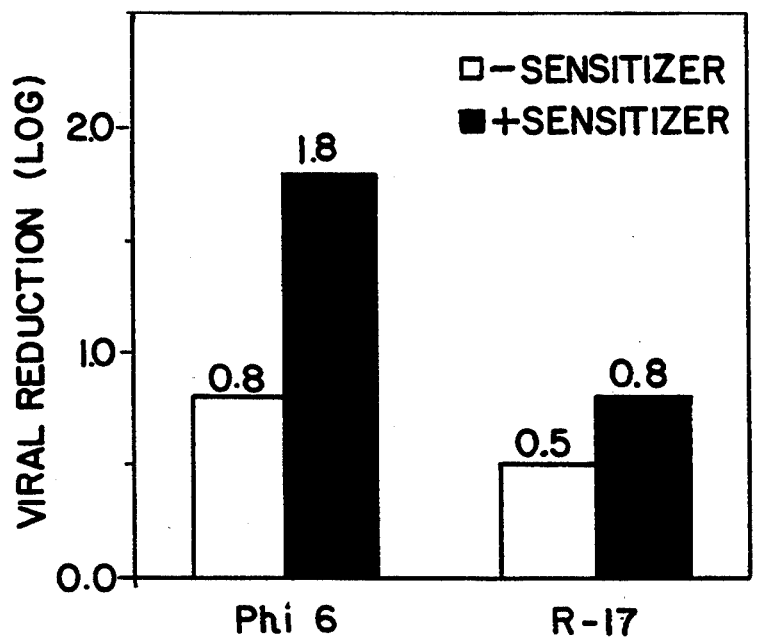
FIG. 4 is a plot viral reduction in plasma according to the procedure of Example 6.

For lyophilized state irradiation, the samples were prepared as described above and transferred to 50 mL round bottom flasks, lyophilized on a bench freeze dryer for 16 hours. The dry powder was placed in petri dishes and X-ray irradiated to 353 Kr. The residual vital titer was determined in reconstituted plasma by the plaque method. The results in FIG. 4 clearly demonstrate that sensitizer compound containing bromine substitutients (EY) produced significantly higher vital reduction in combination with a Mo X-ray source. Higher viral reduction was obtained in the lyophilized state where the interference of water in selective activation of brominated sensitizer was reduced to minimal.

EXAMPLE 23

VIRAL INACTIVATION IN LYOPHILIZED PLASMA IN THE PRESENCE OF A SENSITIZER WITH MOLYBDENUM X-RAY RADIATION

The samples spiked with $\phi 6$ phage had starting titer of $8.1 \times 10^8$ PFU/mL and compound 20 at 0.5 mg/mL was subjected to 420 Kr radiation treatment in lyophilized state. For $R_{17}$ phage samples the initial titer, $3.7 \times 10^8$ PFU, compound $8B_5$ at 0.2 mg/mL and 353 Kr radiation dose were employed. The samples not irradiated with X-ray radiation showed very small or no change in starting vital titer value. Table 7 shows about 3.6 log vital reduction with $\phi 6$ phage and 4.6 log reduction in vital titer of R-17 using the pentabromo psoralen derivative. The damage to factor VIII activity in vital inactivation treated samples is negligible. Greater than 95% recovery of the factor Viii activity was retained after the treatment as measured by APTT times.

EXAMPLE 24

VIRAL INACTIVATION IN RED CELLS USING MOLYBDENUM X-RAY RADIATION

Packed red cells (2.5 mL) were spiked with $\phi 6$ phage to obtain final titer of $5 \times 10^6$ PFU/mL and suspended in 7.5 mL of lyophilization solution containing radiation sensitizer (eosin, 0.6 mg/mL). The samples were frozen ($-25°$ C.) or lyophilized in T-75 tissue culture flasks. Except liquid samples frozen and lyophilized samples were x-ray irradiated while maintaining the sample temperature at $-40°$ C. using dry ice/ethanol bath. Liquid samples were irradiated in the presence of radiation sensitizer (eosin, 0.6 mg/mL) in saline solution. The residual viral titer in each samples was measured after processing the sample with appropriate reconstitution buffers. The viral reduction values and in vitro properties of treated red cells are summarized in Table 8. Respectable levels of viral reductions were obtained in frozen and lyophilized state without significant alterations in red cell properties. The liquid samples produced lower viral reductions and abnormal red cell properties were observed due to the treatment.

EXAMPLE 25

SYNTHESIS OF 5-BROMO-8 ($\gamma$-TRIETHYLAMINOPROPYLOXY) PSORALEN HYDROCHLORIDE (#8B)

5-bromo-8-methoxypsoralen:
8-methoxypsoralen (8-MOP, Aldrich, Milwaukee, Wis., 0.75 g, 3.5 m mol) was dissolved in tetrahydrofuran (THF, 75 mL), Bromine (1.5 mL, 3.5 mmol) in THF (5 mL) was added dropwise. The resulting mixture was stirred at room temperature for overnight. 10% Sodium thiosulfate (5 mL) was added and the solution was basified using conc. aqueous NH4OH, and then extracted twice with chloroform. The organic layer was recrystallized from chloroform to give the product 5-bromo-8-methoxypsoralen (0.75 g, 73.5% yield).

5-bromo-8-hydroxypsoralen:

5-bromo-8-methoxypsoralen (0.75 g, 2.4 mmol) was dissolved in dry methylene chloride (50 mL) and added to a three-neck round bottom flask fitted with a reflux condenser under nitrogen. Boron tribromide in hexane (5.1 mL, 5 mmol) was then added in one portion to the flask via syringe. The resulting reaction mixture was stirred at room temperature for 7 hours after which some yellow solid precipitated. Water (125 mL) was added slowly and cautiously. The resulting heterogeneous mixture was stirred at room temperature for overnight. The crude product was collected by vacuum filtration and air dried. The crude product was recrystallized from acetonitrile (45 mL) to give the product 5-bromo-8-hydroxypsoralen (0.40 g, 58% yield).

5-bromo-8-(7-bromopropyloxy) psoralen:

5-bromo-8-hydroxypsoralen (0.35 g, 1.22 mmol) was dissolved in anhydrous acetone (100 mL). 1,3-dibromopropane (1.5 mL) and anhydrous K2CO3 (3.0 g) were added. The resulting mixture was refluxed for 48 hours. After cooling, the acetone solution was filtered and the solid residue was washed twice with acetone solution was filtered and the solid residue was washed twice with acetone (950 mL). The combined acetone solutions were concentrated to yield an oil which was dissolved in benzene (150 mL). This was chromatographed through a silica plate column containing water (5%). The product eluted with benzene and was concentrated to give the product 5-bromo-8-(γ-bromopropyloxy) psoralen (0.3 g, 60% yield).

5-bromo-8(7-triethylaminopropyloxy)psoralen hydrochloride:

5-bromo-8-(γ-bromopropyloxy)psoralen (0.3 g, 0.73 mmol) was dissolved in anhydrous ethanol (10 mL). Triethylamine (( was added and heated at 60° C. for 5 hours. After cooling, the brown solution was poured into water (100 mL) and extracted twice with chloroform (200 mL). The organic layer was dried with MgSO4 and concentrated to give an oil. The hydrochloride salt of the product was precipitated by adding anhydrous ethanol (2 mL), conc. aqueous HCl (0.5 mL) and ether (2 mL). The resulting mixture was collected in the freezer overnight and the precipitate was vacuum filtered to give a white solid which was recrystallized from anhydrous ethanol: hexane (1:5, v/v) to give the product 5-bromo-8(γ-triethylaminopropyloxy)psoralen hydrochloride (0.15 g, 48% yield). Melting Point 196°-198° C. The product was characterized by $^1$H NMR, $^{13}$C NMR and FAB mass spectrometry.

EXAMPLE 26

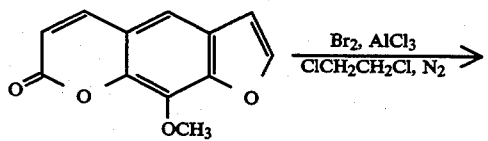

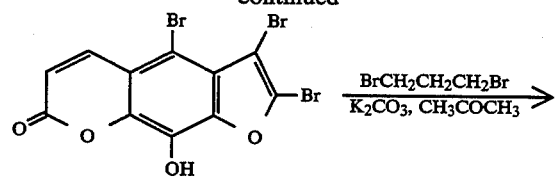

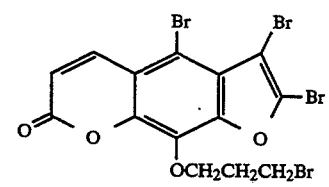

8-Hydroxyl-2,3,9-tribromopsoralen

The mixture of aluminum chloride (13.4 g, 100 mmol) and 40 mL of 1,2-dichloroethane was purged with nitrogen, cooled with ice-salt bath, and stirred as the solution of 4.32 g (20.0 mmol) of 8-methoxypsoralen in 60 mL of 1,2-dichloroethane was added dropwise over 30 min. Then followed was the addition of bromine (9.6 g, 60 mmol) over 1 h. After stirred at 0° C. for 2 h, the reaction was then allowed to stand still overnight at room temperature. The reaction mixture was poured into the mixture of ice (200 g) and concentrated hydrochloric acid (30 mL0, and stirred over 3 h. The solid was collected by vacuum filtration, washed with acetone, and then transferred into 500 mL of acetone, which consequently was refluxed over 2 h. After cooled, the gray solid was collected, weighted 8.74 g (100%), mp 305°-10° C., $^1$HNMR(DMSO-d6, ppm): 11.40 (Br, 1H), 8.12 (d, J=9.2 Hz, 1H), 6.55 (d, J=9.2 Hz, 1 H). $^{13}$CNMR: the spectrum was taken due to the lack of suitable solvent, HRMS mass cald for $C_{11}H_3{}^{79}Br_3O_4$ 436.1441, found 435.7561, major fragments m/e (relative intensity %): 442(0.93, M$^+$+6), 440(2.98, M$^+$+4), 438(3.14, M$^+$+2), 436(0.95, M+), 396(20.76), 394(27.69), 317(11.70), 315(45.52), 313(34.56), 271(23.45), 269(35.28), 82(98.56), 80(100), 79(41.99).

8-(3-Bromopropan)oxy-2,3,9-tribromopsoralen

To the mixture of 4.39 g (10.0 mmol) of 8-Hydroxyl-2,3,9-tribromopsoralen and 10.1 g (50 mmol) of 1,3-dibromopropane in 8omL of DMSO, was added 7.0 g of K2CO3. After stirred at 60° C. for 2 days, the reaction mixture then was poured into 250 mL of ethyl acetate, which was followed by 3 times of washing with 150 mL of water, dried over Na2SO4 and concentrated by rotatory evaporation to about 50 mL. About the same amount of petroleum ether was added to the residue to get precipitate, which was collected by filtration to give out 3.70 g (66%) of yellow solid. mp 116°-8° C. $^1$HNMR(DMSO-d6, ppm): 8.13 (d.d., J$_1$=10Hz, J$_2$=2Hz, 1H) , 6.59 (d, J=10Hz, 1H) , 4.43 (t., J=5.9 Hz, 2 H) , 3.74 (t., J=6.5 Hz, 2 H) , 2.27 (m. 2H). $^{13}$CNMR: HRMS mass cald for $C_{14}H_8{}^{79}Br_4O_4$ 556.2197, found 555.7178, major fragments m/e (relative intensity %): 564 (0.43, M$^+$+8), 562 (1.56, M$^+$+6) , 560 (3.02, M$^{+'}$4) , 558 (1.34, M$^+$+2), 556 (0.36, M+), 518 (14.90), 516 (23.75), 514 (18.28), 474 (11.00), 472 (34.13), 470 (36.94), 468 (13.86), 396 (44.12), 394 (60.20), 352 (47.04), 349 (100), 348 (60.91), 271 (33.81), 269 (54.70).

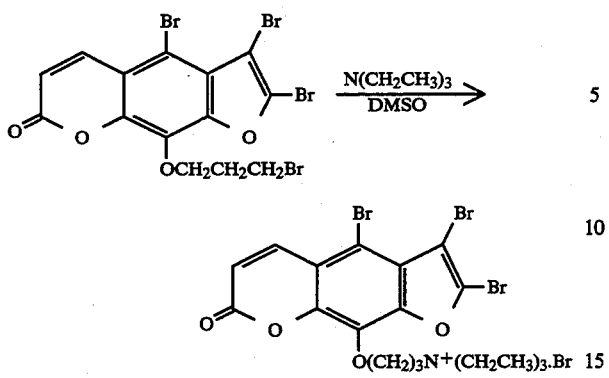

3-[8-(2,3,9-Tribromopsoralen)oxy]propyltriethyl ammonium bromide 2.0 mL of triethylamine was added to the mixture of 0.561 g (1.00 mmol) of 8-(3-Bromopropan)oxyl-2,3,9-tribromopsoralen and 8 mL of dimethyl sulfone. After stirred at 50°–60° C. for 2 days, the reaction mixture was poured into about 30 mL of water, the produced precipitate was then collected by filtration, recrystallized from ethanol and ethyl acetate to give 0.435 g (66%) yellow solid. mp 224°–6° C. (dec.). $^1$HNMR(DMSO$_{d-6}$, ppm): 8.21 (d d, $J_1$=10.0 Hz, $J_2$=2.0 Hz, 1 H) , 6.64 (d, J=10.0 Hz, 1 H), 4.46 (t, J=4.8 Hz, 2 H), 3.47–3.26 (m, 8H), 2.15 (m, 2 H), 1.23 (t, J=7.0 Hz, 2H).

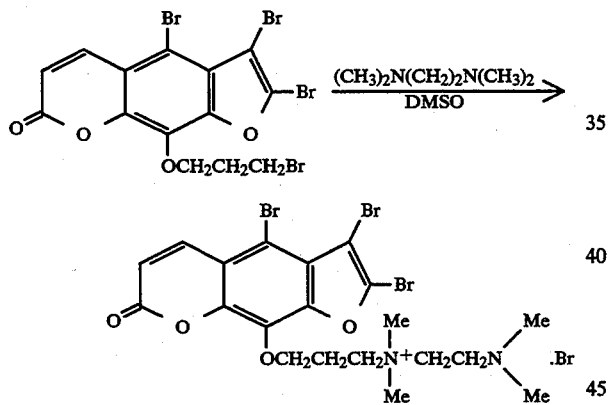

3-[8-(2,3,9-Tribromopsoralen)oxy]propyldimethyl-2-dimethylamminoethyl ammonium bromide 2.0 mL of N,N,N',N'-tetramethylethylenediamine was added to the mixture of 1.12 g (2.00 mmol) of 8-(3-Bromopropan) oxyl-2,3,9-tribromopsoralen and 20 mL of dimethyl sulfone. After stirred at 50°–60° C. for 2 days, the reaction mixture was poured into about 100 mL of water, the produced precipitate was then collected by filtration, recrystallized from ethanol and ethlyl acetate to give 0.700 g yellow solid. mp 189°–92° C. (dec.) $^1$HNMR(CDCl$_3$, ppm): 8.18, 8.12 (d d, J=10.0 Hz, 1 H), 6.45 (d, J=10.0 Hz, 1H), 4.49 (t, J=6.2 Hz, 2H), 4.12 (t, J=8.4 Hz, 2H), 3.88 (t, J=5.7 Hz, 2 H), 3.55 (s, 6 H), 2.89 (t, J=5.4 Hz, 2 H), 2.53–2.41 (M, J,=6.3 Hz, 2 H) , $^{13}$CNMR(CDCl$_3$, ppm): 159.7, 147.1, 146.9, 144.1, 142.5, 131.5, 127.8, 115.7, 115.6, 107.4, 105.6, 72.7, 72.6, 71.3, 70.6, 70.3, 61.6, 49.1, 46.9, 42.7, 27.7, 11.6. HRMS mass cald for $C_{24}H_{33}{}^{35}ClNO_7$ 556.2197, found 555.7178, major fragments m/e (relative intensity %): 564(0.43, m+ +8), 562(1.56, M+ +6) , 560(3.02, M+ +4) , 558(1.34, M+ +2), 556(0.36, M+), 518(14.90), 516(23.75), 514(18.28), 474(11.00), 472(34.13), 470(36.94), 468(13.86), 396(44.12), 394(60.20), 352(47.04), 349(100), 348(60.91), 271(33.81), 269(54.70).

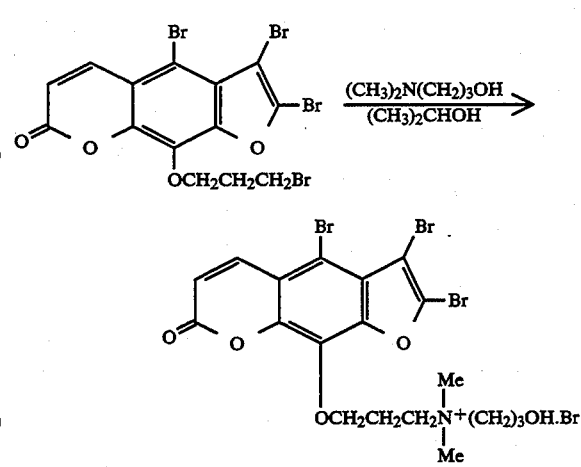

3-[8-(2,3,9-Tribromopsoralen)oxy]propyl-(2-hydroxyl)ethyldimethylammonium bromide The mixture of 0.261 mg (0.500 mmol) of 8-(3-Bromopropan)oxyl-2,3,9-tribromopsoralen and 0.5 mL of the required amine in 5 mL of isopropanol was refluxed for 24 hrs. After cooled, the mixture was poured in 10 mL of water. The yellow solid was collected by filtration and recrystallized from ethanol-ethyl acetate. Yield 0.221 g (67%). mp 225–8° C. (dec.) $^1$HNMR(DMSO$_{d-6}$, ppm): 8.27 (d d, $J_1$=10.0 Hz, $J_2$=2.0 Hz, 1 H) , 6.67 (d, $J_1$=10.0 Hz, $J_2$=1.3 Hz, 1 H), 4.44 (t, J=5.4 Hz, 2 H), 3.62–3.35 (m, 6 H), 3.10 (s, 6 H), 2.28–2.19 (m, 2 H), 1.92–1.83 (m, 2 H).

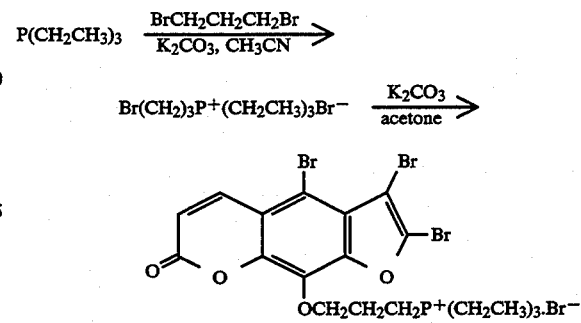

(3-Bromo)propyltriethylphosphonium bromide

The solution of 0,591 mL (0,473 g, 4.00 mmol) of triethlphosphine in 5 mL of acetonitrile was added to the refluxing solution of 4.04 g (20.0 mmol) of 1,3-dibromopropane in 15 mL of acetronitrile over 1 hr. under argon atmosphere. After the addition completed, the reaction mixture was refluxed for another 6 hrs. After cooled, acetonitrile was evaporated, 15 mL of ethyl acetate was then introduced into the residue. After stored in refrigerator for a couple of hours, the highly hygroscopic white solid was collected by filtration. Yield 1.09 g (85%) . $^1$HNMR(DMSO$_{d-6}$, ppm): 3.64 (t, J=6.7 Hz, 2 H) , 2.36–2.17 (m, 8 H) 2.08–2.02 (m, 2 H), 1.13 (d t, $J_1$=18.2 Hz, $J_2$=7.7 Hz, 1 H).

3-[8-(2,3,9-Tribromopsoralen)oxy]propyltriethylphosphonium bromide

The mixture of 0.439 g (1.00 mmol) of 8-Hydroxyl-2,3,9-tribromopsoralen, 0.351 g (1.10 mmol) of (3-

Bromo)propyltriethylphosphonium bromide, and 0.4 g of potassium carbonate in 3 omL of acetone was refluxed under argon for 5 days. After acetone was evaporated, 30 mL of water was poured into the residue, and the water solution was then saturated with potassium bromide. The dark yellow crude product was collected by filtration and recrystallized with ethanol-ethyl acetate. Yield 0.439 g (65%). mp 225°–8° C. (dec.). $^1$HNMR(CDCl$_3$, ppm): 8.20 (d d, J,=10.0 Hz, J$_2$=2.6 Hz, 1 H), 6.46 (d, J=10.0 Hz, 1 H), 4.52 (t, J=4.9 Hz, 2 H), 3.04–2.90 (m, 2 H) , 2.60 (d q, J$_1$=13.1 Hz, J$_2$=7.7 Hz, 6 H), 2.33–2.27 (m, 2 H), 1.36 (d t, J,=18.1 Hz, J$_2$=7.7 Hz, 9 H).

TABLE 1

Influence of Sensitizer Side Chain on The Viral Inactivation Treatment

| Compounds | HSR | ADP Aggregation | Morphology |
|---|---|---|---|
| No Sensitizer | | | |
| −light | 64.2 ± 9.9 | 61.7 ± 6.6 | 285 ± 9 |
| +light | 44.2 ± 3.9 | 64.5 ± 8.9 | 248 ± 4 |
| AMT | 26.0 ± 2.9 | 0.4 ± 0.6 | 301 ± 9 |
| 8QA | 37.0 ± 13.8 | 45.2 ± 13.2 | 239 ± 4 |
| 8C | 44.9 ± 7.2 | 49.6 ± 14.3 | 251 ± 8 |

2 mL PRP samples (plastic disposable petri dishes) containing 0.1 mg/mL sensitizer were irradiated with UVA for 6 min. (1.19 J/cm$^2$). The intensity of UVA radiation at sample position was measured at 3.3 mW/cm$^2$. The data was obtained from three separate experiments using different platelet concentrates. Values are mean ± SD.

TABLE 4

UVA Exposure Times for Red Cell Viral Inactivation

| UV Reactor # | Irradiation (direction) | UVA Intensity (mW/cm$^2$) | Time Required for 6.0 lo V.I. Hours |
|---|---|---|---|
| 1. | Top | 3.3 | 16.4 (n = 1) |
| 2. | Top + Bottom | 3.6 3.4 | 7.0 ± 1.2 (n = 9) |
| 3. | Top ± Bottom | 40 40 | 1.3 ± 0.4 (n = 3) |

UVA exposure time required to achieve 6.0 logs of viral reduction in full units of red cells (60% hematocrit) using 0.1 mg/ml #8B sensitizer.

TABLE 5

Viral Inactivation in Human Plasma And Fetal Bovine Serum

| | Viral Reduction (log) | | |
|---|---|---|---|
| Sample | φ6 | λ | R-17 |
| Plasma | 6.5 | 6.5 | 5.5 |
| Fetal bovine serum | 6.5 | 6.6 | N/A |

Experimental details are described in example 18.

TABLE 2

Viral Inactivation in Single Unit Platelet Concentrates

| | Platelet In Vitro Properties | | | | | |
|---|---|---|---|---|---|---|
| | 0 Hour | | 24 Hours | | 48 Hours | |
| Assays | Control* | Treated | Control | Treated | Control | Treated |
| ADP Agg. | 49 ± 19 | 43 ± 12 | 43 ± 21 | 34 ± 19 | 32 ± 22 | 26 ± 10 |
| Collagen | 70 ± 5 | 72 ± 3 | 63 ± 3 | 65 ± 3 | 64 ± 8 | 60 ± 4 |
| HSR | 74 ± 9 | 65 ± 8 | 75 ± 4 | 65 ± 6 | 73 ± 2 | 70 ± 6 |
| pH | 7.3 ± 0.1 | 7.2 ± 0.1 | 7.5 ± 0.1 | 7.1 ± 0.2 | 7.5 ± 0.1 | 6.8 ± 0.1 |
| Morphology | 286 ± 32 | 233 ± 17 | 263 ± 16 | 230 ± 9 | 229 ± 7 | 217 ± 11 |
| Cell count | 442 ± 31 | 474 ± 20 | 450 ± 60 | 499 ± 50 | 453 ± 42 | 506 ± 10 |
| V.I (log$_{10}$) | 0 | 5.3 ± 0.2$ | | | | |

Single units of platelet concentrates in Cyrocyte ™ bag containing 0.03 mg/mL #8B sensitizer (Appendix I) were irradiated from top (3.6 mW/cm$^2$) and bottom (3.4 mW/cm$^2$) using UVA radiation in a home made reactor for 10 min (4.2 J/cm$^2$). After the treatment platelet concentrates were transferred into original platelet containers and stored in a platelet incubator for indicated period of time. Platelet viability assays were carried out immediately after treatment and following 24 & 48 hours storage in a platelet incubator. The viral reduction in treated samples was determined by the plaque assay. The values are mean ± S.D (n = 3)
Treated control exposed for 10 min. to UVA produced 0.4 logs of viral infection.
*Data represents n = 6
$Values are in log (n = 4)
Note: Cyrocyte ™ is a trademark of Baxter's Fenwal product line

TABLE 3

Properties of Red Cells Following Viral Inactivation Treatment (Full Units)

| | Red Cell in Vitro Properties | | | | | |
|---|---|---|---|---|---|---|
| | Day 1 | | Day 2 | | Day 7 | |
| Assays | Control | Treated | Control | Treated | Control | Treated |
| MCV | 91.0 ± 4.5 | 88.8 ± 2.5 | 88.6 ± 1.3 | 89.8 ± 1.7 | 89.8 ± 1.7 | 89.8 ± 1.7 |
| MCH | 29.6 ± 0.9 | 30.9 ± 0.1 | 30.5 ± 0.3 | 30.3 ± 0.4 | 30.6 ± 0.6 | 30.1 ± 0.8 |
| MCHC | 33.7 ± 0.7 | 34.9 ± 0.4 | 34.4 ± 0.2 | 33.8 ± 0.9 | 34.0 ± 0.3 | 33.6 ± 1.6 |
| % Oxy Hb. | 92.3 ± 0.5 | 95.2 ± 0.1 | 99.4 ± 0.5 | 97.7 ± 1.7 | 99.1 ± 0.6 | 98.5 ± 1.0 |
| % Met Hb. | 0.5 ± 0.5 | 2.9 ± 1.5 | 0 ± 0 | 1.7 ± 1.7 | 0 ± 0 | 1.4 ± 1.2 |
| % Hemichrome | 0.3 ± 0.4 | 1.9 ± 1.5 | 0.6 ± 0.9 | 0.6 ± 0.9 | 0.9 ± 0.6 | 0.2 ± 0.2 |
| DI Max % control | 100 ± 0 | 97.4 ± 3.6 | 102 ± 3.3 | 99.6 ± 3.8 | 101 ± 5.9 | 99.0 ± 5.9 |
| Viral Reduction (log) | 0 | 6.6 ± 0.1 | | | | |

DI Max, Deformability index by ektacytometry
Viral inactivation treatment was carried out in packed red cells (full units, 60% Hct.) containing model virus (φ6 phage) and 8B sensitizer (0.3 mg/mL) in a Sericon red cells freezing bag (altered). The bags were irradiated from top (3.6 mW/cm$^2$) and bottom (3.4 mW/cm$^2$) in a home made reactor for 6 hours (151.2 J/cm$^2$). The sample was mixed continuously during UVA exposure on a orbital shaker. Data was collected from 3 separate experiments and the values are mean ± S.D with unpaired controls.

TABLE 6

PLATE INCORPORATION ASSAY
Test Article: Evaluation of Sensitizer #8B for Mutagenicity (In Vitro), Sensitizer #8B

| | Salmonella typhimurium Tester Strains | | | | |
|---|---|---|---|---|---|
| | TA98 | TA100 | TA1535 | TA1537 | TA1538 |
| | Number of Revertan Colonies (Average of Duplicate Plates) | | | | |
| DMSO (− control) | 61 | 165 | 126 | 31 | 21 |
| DMSO test artile solution undiluted | 55 | 164 | 173 | 36 | 22 |
| DMSO w/S-9 (− control) | 80 | 196 | 105 | 30 | 21 |
| DMSO w/S-9 test article solution (undiluted) | 83 | 245 | 197 | 26 | 25 |
| Dexon 1 mg/ml (+ control) | 1963 | 1767 | N/A | 1021 | N/A |
| Dexon 1 mg/ml w/S-9 (+ control) | 1649 | 1413 | N/A | 629 | N/A |
| Sodium azide 0.1 mg/ml (+ control) | N/A | N/A | 4043 | N/A | N/A |
| Sodium azide 0.1 mg/ml w/S-9 (+ control) | N/A | N/A | 4475 | N/A | N/A |
| 2-nitroflurene 1 mg/ml (+ control) | N/A | N/A | N/A | N/A | 3965 |
| 2-nitroflurene w/S-9 (+ control) | N/A | N/A | N/A | N/A | 1806 |
| 2-aminoflurene 0.1 mg/ml (+ control) | N/A | 291 | N/A | N/A | 81 |
| 2-aminoflurene w/S-9 (+ control) | N/A | 3415 | N/A | N/A | 4907 |

N/A = Not Applicable
In no case was there a two-fold or greater increase in the reversion rate of the tester strains in the presence of the test article solution.

TABLE 7

Inactivation of Viruses in Plasma Using Molybdenum X-Ray Radiation

| VIII Treatment | Viral Reduction (log) | | | Residual Factor Activity (%) |
|---|---|---|---|---|
| | φ6 | R-17 | λ | |
| X-ray radiation (Hydrated state) | 1.1 | 0.5 | N.D. | <7.0 |
| X-ray radiation (Lyophilized state) | 3.1 | 4.4 | 4.6 | >95 |

Experimental details are described in example 23.

TABLE 8

Viral Inactivation in Red Cells Using X-Ray Radiation

| Assay State | Without Viral Inactivation Treatment | | | With Viral Inactivation Treatment | | |
|---|---|---|---|---|---|---|
| | Liquid | Frozen | Lyophilized | Liquid | Frozen | Lyophilized |
| Viral Reduction | 0 | 0 | 0 | 2.3 ± 0.05 | 4.9 ± 0.3 | 5.2 ± 1.3 |
| MCV | 88.6 ± 0.1 | 94.3 ± 0.3 | 97.5 ± 0.5 | 100.4 ± 1.5 | 96.9 ± 0.2 | 100.3 ± 0.4 |
| MCH | 29.9 ± 0.3 | 32.4 ± 0.4 | 29.7 ± 0.5 | 46.3 ± 0.5** | 32.0 ± 0.8 | 31.0 ± 2.4 |
| MCHC | 33.7 ± 0.5 | 34.3 ± 0.6 | 30.4 ± 1.5 | 46.1 ± 1.1** | 33.0 ± 0.7 | 30.9 ± 2.2 |
| Osmotic stability | 88.9 ± 1.3 | 93.2 ± 1.4 | 92.2 ± 0.8 | 91.8 ± 2.8 | 95.9 ± 1.0 | 88.9 ± 6.6 |
| % Oxy Hb. | 99.8 ± 0.3 | 99.3 ± 0.6 | 96.3 ± 0.9 | 96.3 ± 1.9 | 99.0 ± 0.8 | 93.0 ± 1.6 |
| % Met Hb | 0.3 ± 0.5 | 0 | 0 | 3.2 ± 1.9 | 0 | 2.36 ± 2.33 |
| % Hemi. | 0 | 0.7 ± 0.6 | 3.72 ± 0.9 | 0.5 ± 0.9 | 1.0 ± 0.8 | 4.6 ± 1.1 |
| D.I. Max | 0.58 ± 0.01 | 0.58 ± .02 | .052 ± 0.02 | 0.56 ± 0.02 | 0.57 ± 0.01 | 0.51* |
| D.I. Max Control | 95.7 ± 2.3 | 97.3 ± 2.4 | 87.4 ± 2.4 | 92.6 ± 3.7 | 96.5 ± 1.8 | 86.5* |

The data represents average and standard deviation from 3 separate sets of samples.
Red cell indices were measured after reconstitution with saline solutions except liquid samples which were analyzed after centrifugation.
All preparations contained a sensitizer concentration of 0.6 mg/mL. The approximate delivered radiation dose was 161.3 rads as measured using liquid Frick dosimetry.
D.I., Deformability index as measured by ektacytometry, is the maximum deformability observed at 300 mOs.
*Data represents n = 2.
**Highly abnormal values for these samples are due to extensive aggregation following treatment. The aggregation inhibited the hematology analyzer cell count and produced inconsistent and highly suspect values. This occurs only for samples treated in the liquid state.

Appendix I
(Nucleic Acid Target UV/X-Ray Radiation Sensitizers)

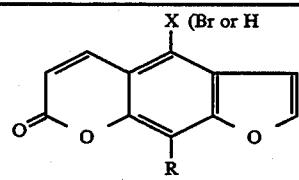

Sensitizer Designation        X =        R =

-continued

Appendix I
(Nucleic Acid Target UV/X-Ray Radiation Sensitizers)

| | | |
|---|---|---|
| 8 | Br | $-OCH_2CH_2CH_2N(C_2H_5)_2 \cdot HCl$ |
| 8QA | Br | $-OCH_2CH_2CH_2\overset{+}{N}(CH_3)_3$ |
| 8A | Br | $-OCH_2CH_2CH_2\overset{+}{N}(CH_3)_3$ |
| 8B | Br | $-OCH_2CH_2CH_2\overset{+}{N}(C_2H_5)_3$ |
| 8C | Br | $-OCH_2CH_2CH_2\overset{+}{N}(C_2H_5)_3$ |
| 8D | Br | $-O(CH_2)_6\overset{+}{N}(CH_3)_3$ |
| 8E | Br | $-O(CH_2)_5\overset{+}{N}(CH_3)_3$ |
| 8G | Br | $-O(CH_2)_7\overset{+}{N}(CH_3)_3$ |
| 8I | Br | $-O(CH_2)_4\overset{+}{N}(CH_3)_3$ |
| 8H | Br | $-O(CH_2)_5\overset{+}{N}(C_2H_5)_3$ |
| 8K | Br | $-OCH_2CH_2\overset{+}{N}(C_2H_5)_3$ |
| 8J | Br | $-OCH_2CH_2CH_2\overset{+}{N}(C_3H_9)_3$ |
| 8B5 | Br Br | $-OCH_3$ |

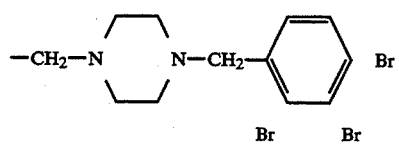

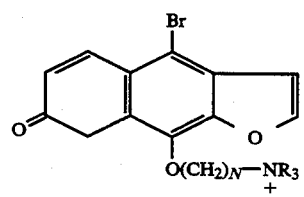

N = 2-7
R = CH$_3$, CH$_3$CH$_2$, CH$_3$CH$_2$CH$_2$, CH$_3$CH$_2$CH$_2$CH$_2$

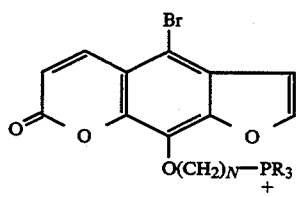

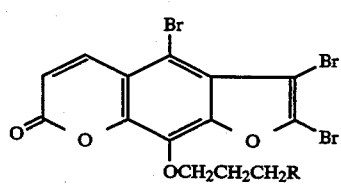

and

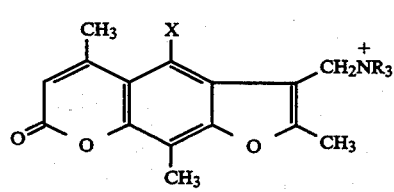

X = H or Br

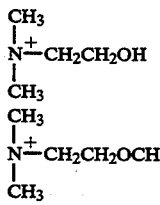

$R = \underset{CH_3}{\overset{CH_3}{\underset{|}{\overset{|}{N^{\pm}}}}}-CH_2CH_2CH_2-\underset{CH_3}{\overset{CH_3}{\underset{|}{\overset{|}{N}}}}$ $R = \overset{+}{P}(CH_3)_3$
$\overset{+}{P}(CH_2CH_3)_3$
$\overset{+}{P}(CH_2CH_2CH_3)_3$ $\underset{CH_3}{\overset{CH_3}{\underset{|}{\overset{|}{N^{\pm}}}}}-CH_2CH_2OH$ $\underset{CH_3}{\overset{CH_3}{\underset{|}{\overset{|}{N^{\pm}}}}}-CH_2CH_2OCH_2CH_2OH$

Appendix I
(Nucleic Acid Target UV/X-Ray Radiation Sensitizers)
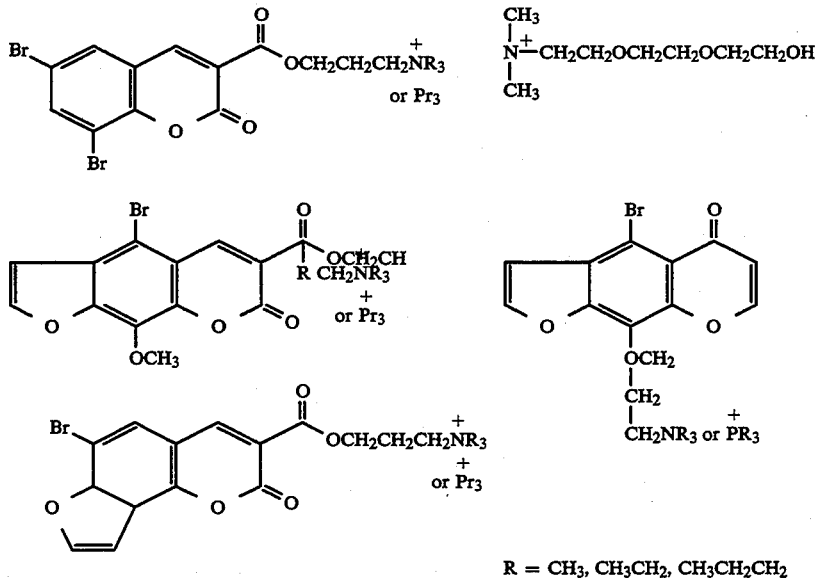
R = CH$_3$, CH$_3$CH$_2$, CH$_3$CH$_2$CH$_2$
APPENDIX II
(Nucleic Acid Target Visible/X-Ray Radiation Sensitizers)
(3) Positively Charged Porphyrins
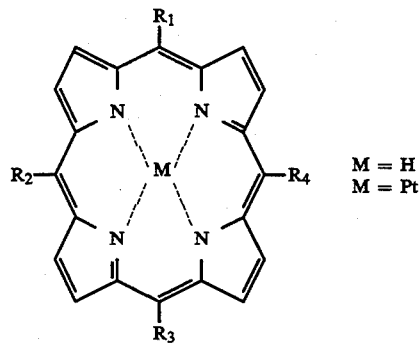
M = H
M = Pt
APPENDIX II
(Nucleic Acid Target Visible/X-Ray Radiation Sensitizers)
(3) Positively Charged Porphyrins
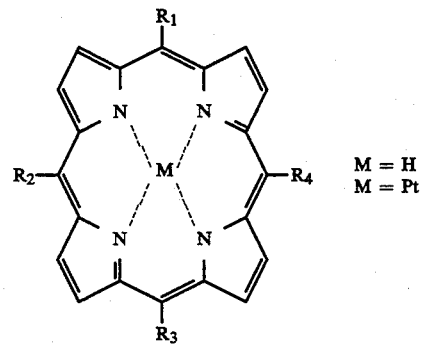
M = H
M = Pt
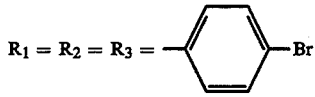
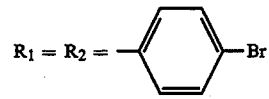
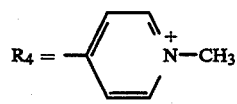
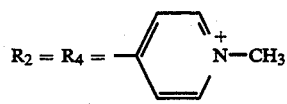
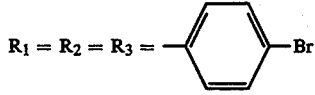
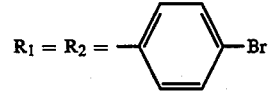
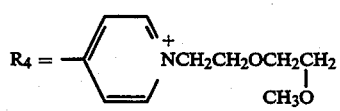
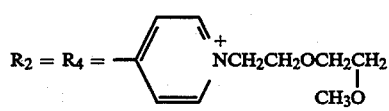

APPENDIX II
(Nucleic Acid Target Visible/X-Ray Radiation Sensitizers)
(3) Positively Charged Porphyrins

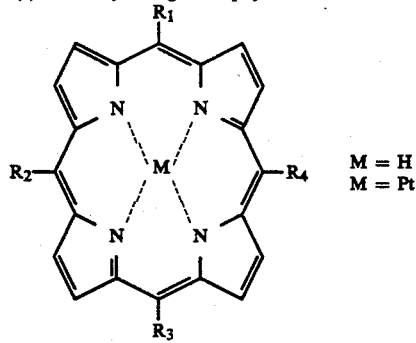

M = H
M = Pt

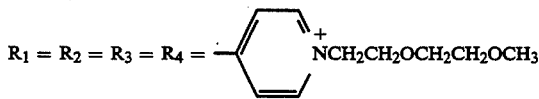

$R_1 = R_2 = R_3 = R_4 =$ —⟨phenyl⟩—$\overset{+}{N}CH_2CH_2OCH_2CH_2OCH_3$

Appendix III
(Membrane Target Visible/X-Ray Radiation Sensitizers)

| Negatively Charged Phthalocyanines | Negatively Charged Benzoporphyrins |
|---|---|

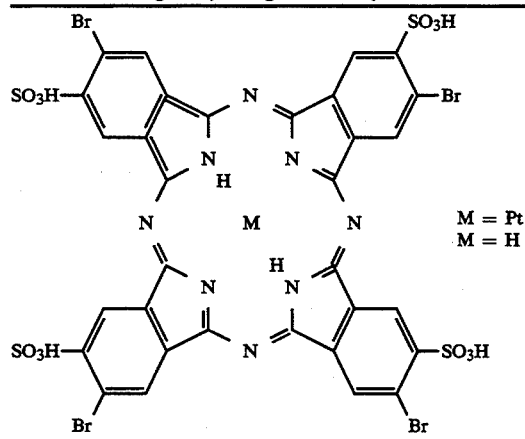

M = Pt
M = H

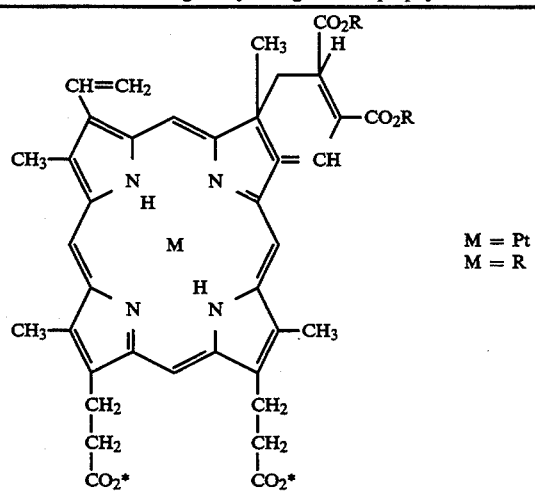

M = Pt
M = R

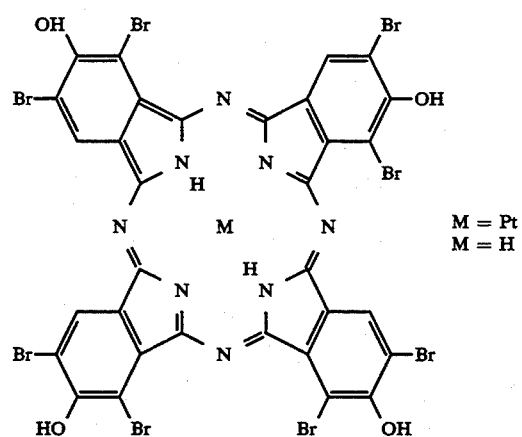

M = Pt
M = H $R = CH_2CBr_3$

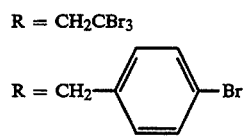

$R = CH_2$—⟨phenyl⟩—Br

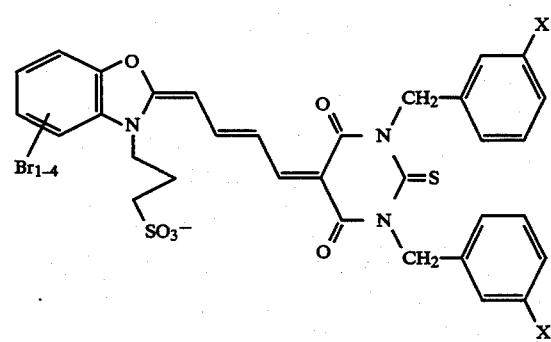

MER-H    X = H
MER-Br   X = Br

Appendix III
(Membrane Target Visible/X-Ray Radiation Sensitizers)

Negatively Charged Phthalocyanines      Negatively Charged Benzoporphyrins

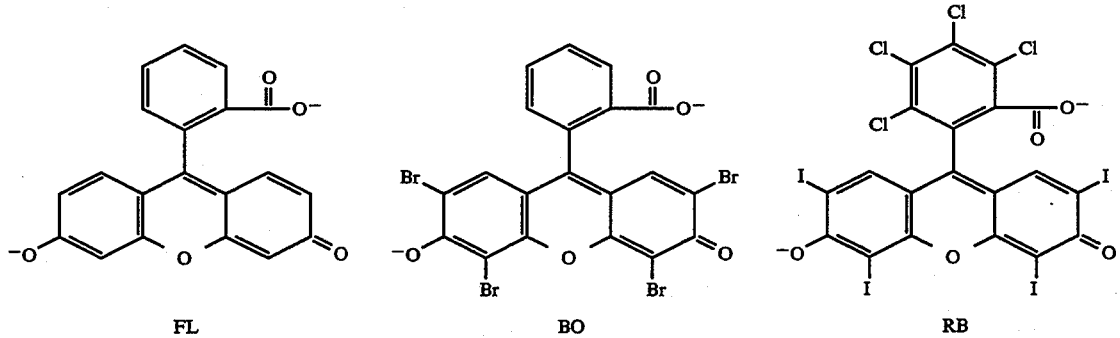

FL      BO      RB

What is claimed is:

1. A process for reducing viral, and/or bacterial contaminants in a composition comprising blood, a blood component, cell cultures or a component of a cell culture, comprising the steps:

mixing said composition in a liquid state with a chemical radiation sensitizer capable of targeting said viral, and/or bacterial contaminants, wherein said sensitizer is a compound of the formula:

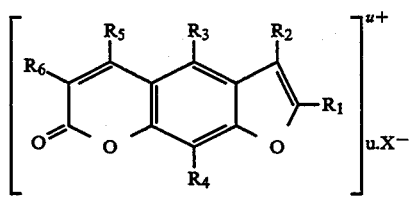

wherein u is an integer from 1 to 6; X is an anionic counterion; $R_1$, $R_2$, $R_3$, $R_4$, $R_5$, and $R_6$ are independently halo; H; linear or branched alkyl of 1–10 carbon atoms; linear or branched alkoxy of 1–10 carbon atoms; $(CH_2)_mO(CH_2)_pZ^{\oplus}R'$, $R''$, $R'''$ or $-O(CH_2)_nZ^{\oplus}R'$, $R''$, $R'''$ wherein n, m and p are independently integers from 1 to 10 and $R'$, $R''$, $R'''$ are independently H or linear or branched alkyl of 1 to 10 carbon atoms; at least one of $R_1$, $R_2$, $R_3$, $R_4$, $R_5$, and $R_6$ is halo; and at least one of $R_1$, $R_2$, $R_3$, $R_4$, $R_5$, and $R_6$ is $(CH_2)_mO(CH_2)_pZ^{\oplus}R'$, $R''$, $R'''$ or $-O(CH_2)_nZ^{\oplus}R'$, $R'''$; Z is N or P; and exposing said composition and sensitizer to electromagnetic radiation of sufficient wavelength and intensity for a period of time sufficient to activate said sensitizer whereby the activation of said sensitizer reduces said contamination in said composition.

2. A process according to claim 1 wherein said composition comprises whole blood or a cellular fraction prepared from whole blood.

3. A process according to claim 2 wherein said blood cell fraction comprises red blood cells, platelets, white blood cells, or stem cells.

4. A process according to claim 1 wherein said composition comprises whole plasma or a blood plasma fraction.

5. A process according to claim 4 wherein said blood plasma fraction comprises plasma protein fractions.

6. A process according to claim 5 wherein said plasma protein fractions comprise serum albumin, immune globulins, or a clotting factor.

7. A process according to claim 6 wherein said clotting factor comprises Factor VIII.

8. A process according to claim 1 wherein said cell culture comprises growth media containing serum supplements.

9. A process according to claim 8 wherein said serum supplements comprise whole animal serum or fractions derived from whole animal serum.

10. A process according to claim 9 wherein said animal serum comprises bovine serum.

11. A process according to claim 10 wherein said bovine serum comprises fetal calf serum.

12. A process according to claim 8 wherein said growth media comprises serum supplements used to propagate mammalian cell lines.

13. A process according to claim 12 wherein said culture comprises mammalian cell lines containing recombinant genetic material for expression of recombinant proteins.

14. A process according to claim 13 wherein said culture comprises recombinant plasma proteins.

15. A process according to claim 14 wherein said recombinant plasma proteins comprise recombinant serum albumin or recombinant clotting factors.

16. A process according to claim 15 wherein said recombinant clotting factors comprise recombinant Factor VIII.

17. A process according to claim 12 wherein said mammalian cell lines comprise hybridoma cell lines.

18. A process according to claim 17 wherein said hybridoma cell lines produce monoclonal antibodies.

19. A process according to claim 1 wherein said composition comprises pharmaceutically useful proteins.

20. A process according to claim 19 wherein said proteins comprise growth factors and hormones.

21. A process according to claim 1 wherein said electromagnetic radiation comprises ultraviolet light.

22. A process according to claim 21 wherein said ultraviolet light is characterized by wavelengths of 400 nanometers or less.

23. A process according to claim 1 wherein $R_4$ is $-O-CH_2-_nN^{\oplus}R'R''R'''$.

24. A process according to claim 23 wherein $R'$, $R''$ and $R'''$ are ethyl.

25. A process according to claim 24 wherein $R^6$, $R^5$, $R^2$ and $R^1$ are hydrogen 26. A process according to claim 25 wherein $R^3$ is H or halo.

27. A process according to claim 26 wherein $R^3$ is bromo.

28. A process according to claim 27 wherein n=3.

29. A process according to claim 23 wherein R', R" and R'" are methyl.

30. A process according to claim 29 wherein $R^1$, $R^2$, $R^5$ and $R^6$ are hydrogen and $R^3$ is halo.

31. A process according to claim 30 wherein $R^3$ is bromo.

32. A process according to claim 31 wherein n=3, 4, 5, 6 or 7.

33. A process according to claim 27 wherein n=2.

34. A process according to claim 23 wherein R', R" and R'" are n-propyl.

35. A process according to claim 34 wherein $R^1$, $R^2$, $R^5$ and $R^6$ are hydrogen and $R^3$ is halo.

36. A process according to claim 35 wherein $R^3$ is bromo.

37. A process according to claim 1 wherein $R_4$ is $-O-CH_2-_nP^+R'R''R'''$.

38. A process according to claim 37 wherein R', R" and R'" are methyl, ethyl, n-propyl or n-butyl.

39. A process according to claim 38 wherein $R^1$, $R^2$, $R^5$ and $R^6$ are hydrogen and $R^3$ is halo.

40. A process according to claim 39 wherein $R^3$ is bromo.

41. A process according to claim 1 wherein said sensitizer is a compound of the formula:

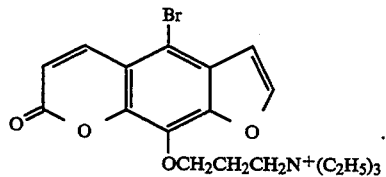

* * * * *

UNITED STATES PATENT AND TRADEMARK OFFICE
CERTIFICATE OF CORRECTION

PATENT NO. : 5,418,130
DATED : May 23, 1995
INVENTOR(S) : Matthew S. Platz, et al It is certified that error appears in the above-indentified patent and that said Letters Patent is hereby corrected as shown below:

Column 1, line 19, change "vital" to --viral--.

Signed and Sealed this

Eighth Day of August, 1995

Attest:

BRUCE LEHMAN

Attesting Officer     Commissioner of Patents and Trademarks